United States Patent [19]
Denny et al.

[11] Patent Number: 6,114,332
[45] Date of Patent: Sep. 5, 2000

[54] BIS(ACRIDINECARBOXAMIDE) AND BIS (PHENAZINECARBOXAMIDE) AS ANTITUMOR AGENTS

[75] Inventors: William Alexander Denny; Swarnalatha Akuritaya Gamage; Julie Ann Spicer; Bruce Charles Baguley; Graeme John Finlay, all of Auckland, New Zealand

[73] Assignee: Xenova Limited, Berkshire, United Kingdom

[21] Appl. No.: 09/284,623

[22] PCT Filed: Oct. 17, 1997

[86] PCT No.: PCT/GB97/02886

§ 371 Date: Jun. 18, 1999

§ 102(e) Date: Jun. 18, 1999

[87] PCT Pub. No.: WO98/17650

PCT Pub. Date: Apr. 30, 1998

[30] Foreign Application Priority Data

Oct. 18, 1996 [GB] United Kingdom .................... 9621795

[51] Int. Cl.$^7$ ........................... A01N 43/58; A01N 43/42; C07D 241/36; C07D 401/00; C07D 219/00
[52] U.S. Cl. ........................ 514/250; 514/250; 514/287; 514/297; 544/338; 544/343; 544/347; 544/348; 544/361; 546/65; 546/102; 546/104
[58] Field of Search ..................... 544/338, 347, 544/348, 343, 361; 546/102, 104; 514/250, 297, 253, 287

[56] References Cited

FOREIGN PATENT DOCUMENTS 0 098 098  1/1984  European Pat. Off. .
0 172 744  2/1986  European Pat. Off. .
WO 99/06372  2/1999  WIPO .

OTHER PUBLICATIONS

Atwell et al., "Potential antitumour agents. 50 In vivo solid–tumor activity of dericatives of N–[2–(dimethylamino)ethyl] acridine–4–carboxamide", *Journal of Medicinal Chemistry*, vol. 30, No. 4, 1987, Washington, U.S., pp. 664–669.

(List continued on next page.)

*Primary Examiner*—Richard L. Raymond
*Assistant Examiner*—Ben Schroeder
*Attorney, Agent, or Firm*—Nixon & Vanderhye

[57] ABSTRACT

A compound which is a bis(acridinecarboxamide) or bis (phenazinecarboxamide) derivative of formula (I):

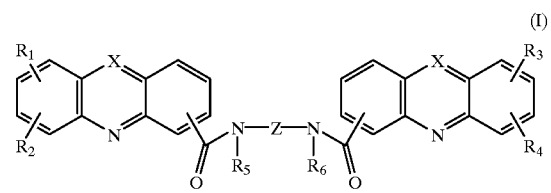

wherein each X, which may be the same or different in a given molecule, is —CH= or —N= each of $R_1$ to $R_4$ which may be the same or different, H, $C_1$–$C_4$ alkyl, OH, SH, $NH_2$, $C_1$–$C_4$ alkoxy, aryloxy, NHR, $N(R)_2$, SR, $SO_2R$ wherein R is $C_1$–$C_4$ alkyl, $CF_3$, $NO_2$ or halogen, or $R_1$ and $R_2$ together form a methylenedioxy group; each of $R_5$ and $R_6$, which may be the same or different, is H or $C_1$–$C_4$ alkyl; Z is $(CH_2)_n$, $(CH_2)_nO(CH_2)_n$, $(CH_2)_nN(R_7)(CH_2)_n$, $(CH_2)_nN(R_7)(CH_2)_mN(R_7)(CH_2)_n$ or $(CH_2)_nN(CH_2CH_2)_2N(CH_2)_n$ wherein $R_7$ is H or $C_1$–$C_4$ alkyl and n and m, which may be the same or different, are each an integer of 1 to 4; or a pharmaceutically acceptable acid addition salt or N-oxide thereof; has activity as an antitumor and antibacterial agent.

8 Claims, 1 Drawing Sheet

OTHER PUBLICATIONS

Rewcastle et al, "Potential antitumor agents. 51. Synthesis and antitumor activity of substituted phenazine–1–carboxamides", *Journal of Medicinal Chemistry*, vol. 30, No. 5, 1987, Washington, U.S., pp. 843–851.

Gamage et al, "A new synthesis of substituted acridine–4–carboxylic acids and the anticancer drug N–[2–(dimethylamino)ethyl] acridine–4–carboxamide (DACA)", *Tetrahedron Letters*, vol. 38, No. 4, Jan. 27, 1997, Oxford, GB, pp. 699–702.

Atwell et al, "Potential antitumor agents.50.In vivo solid–tumor activity of derivatives of N–[2–(dimethylamino)ethyl]acridine–4–carboxamide", *Journal of Medicinal Chemistry*, vol. 30, No.4, 1987, Washington, U.S., pp. 664–669.

BIS(ACRIDINECARBOXAMIDE) AND BIS(PHENAZINECARBOXAMIDE) AS ANTITUMOR AGENTS

This application is a 371 of PCT/GB97/0286, filed Oct. 17, 1997.

The present invention relates to compounds useful as antitumor agents, to their production and to pharmaceutical compositions containing them.

Many compounds which bind reversibly to DNA by intercalation are known to have cellular antiproliferative properties and in vivo antitumor effects, mediated principally through their inhibition of topoisomerase enzymes. For example, the acridine derivatives amsacrine [Issell, *Cancer Treat. Rev.* 1980, 7, 73], asulacrine [Harvey et al., *Eur. J. Cancer*, 1991, 27, 1617] and acridinecarboxamide [Finlay et al., *Eur. J. Cancer* 1996, 32A, 708] are clinical anticancer drugs or in clinical trial, and related 9-azaacridines (phenazines) have been reported to have in vivo antitumor properties in animal models [Rewcastle et al., *J. Med. Chem.*, 1987, 30, 843].

It has now been found that a series of bis(acridinecarboxamide) and bis(9-phenazinecarboxamide) derivatives have antitumor properties. The present invention therefore provides a compound which is a bis(acridinecarboxamide) or bis(phenazinecarboxamide) derivative of formula (I):

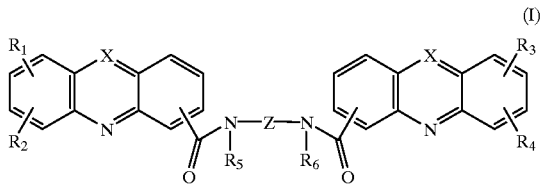

(I)

wherein each X, which may be the same or different in a given molecule, is —CH= or —N=; each of $R_1$ to $R_4$ which may be the same or different, is H, $C_1$–$C_4$ alkyl, OH, SH, $NH_2$, $C_1$–$C_4$ alkoxy, aryl, aryloxy, NHR, $N(R)_2$, SR or $SO_2R$ wherein R is $C_1$–$C_4$ alkyl, $CF_3$, $NO_2$ or halogen, or $R_1$ and $R_2$ form together with the carbon atoms to which they are attached, a methylenedioxy group; each of $R_5$ and $R_6$, which may be the same or different, is H or $C_1$–$C_4$ alkyl; Z is $(CH_2)_n$, $(CH_2)_nO(CH_2)_n$, $(CH_2)_nN(R_7)(CH_2)_n$, $(CH_2)_nN(R_7)(CH_2)_mN(R_7)(CH_2)_n$ or $(CH_2)_nN(CH_2CH_2)_2N(CH_2)_n$, $(CH_2)_nCONH(CH_2)_m$ or $(CH_2)_nCONH(CH_2)_mNHCO(CH_2)_n$ wherein $R_7$ is H or $C_1$–$C_4$ alkyl and n and m, which may be the same or different, are each an integer of 1 to 4; or a pharmaceutically acceptable acid addition salt or N-oxide thereof; with the exception of compounds wherein each X is N, each of $R_1$ to $R_6$ is H, the carboxamide moiety is attached to position 1 of each phenazine ring and Z is $(CH_2)_2NH(CH_2)_2$, $(CH_2)_3NH(CH_2)_3$, $(CH_2)_3N(CH_2CH_2)_2N(CH_2)_3$, $(CH_2)_2NH(CH_2)_2NH(CH_2)_2$ or $(CH_2)_3NH(CH_2)_2NH(CH_2)_3$.

In formula (I) the ring numbering in each tricylic chromophore differs depending on whether X is —CH= (acridine derivatives) or —N= (phenazine derivatives). The numbering used in each case, with reference to one tricyclic moiety, is as follows:

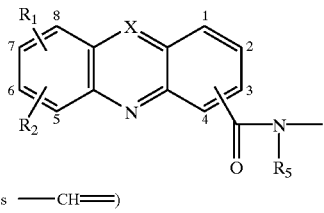

(X is —CH=)

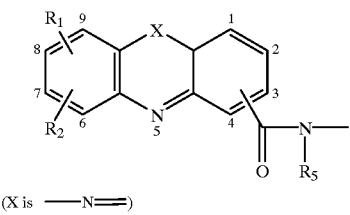

(X is —N=)

In formula (I) the substituents $R_1$ and $R_2$, and $R_3$ and $R_4$, may occupy any one of the available ring positions in their respective tricyclic chromophores. Thus when X in a tricyclic moiety is —CH= then $R_1$ and $R_2$, or $R_3$ and $R_4$ if appropriate, may each be bonded to any one of the available ring positions 1 to 8 not occupied by the carboxamide moiety —C(O)—N($R_5$)—. The carboxamide moiety in turn may be bonded to any one of ring positions 1, 2, 3 and 4, preferably 1 or 4. Typically when X in a given tricyclic chromophore is —CH= one of $R_1$ and $R_2$, or $R_3$ and $R_4$ if appropriate, is hydrogen and the other is hydrogen or is a substituent as defined above for formula (I) bonded at any one of ring positions 1 to 8, and the carboxamide moiety is bonded at position 1 or 4.

When X in a tricyclic moiety is —N= then $R_1$ and $R_2$, or $R_3$ and $R_4$ if appropriate, may each be bonded to any one of the available ring positions 1 to 4 and 6 to 9 which are not occupied by the carboxamide moiety, in particular one of positions 6 to 9. The carboxamide moiety, in turn, may be bonded to either of the ring positions 1 and 2, preferably 1. Typically, when X in a given tricyclic chromophore is —N= one of $R_1$ and $R_2$, or $R_3$ and $R_4$ if appropriate, is hydrogen and the other is hydrogen or is a substituent as defined above for formula (I) at any one of ring positions 1 to 4 or 6 to 9, especially 6, 7, 8 or 9, and the carboxamide moiety is bonded at position 1 or 4.

When the left- and right-hand tricyclic chromophores in formula (I) are identical the compounds are structurally symmetric. When the two chromophores differ in the definition of one or more substituents the compounds are structurally asymmetric. In a preferred aspect of the invention the compounds are structurally symmetric.

A $C_1$–$C_4$ alkyl group may be linear or branched, for instance methyl, ethyl, n-propyl, i-propyl, n-butyl, s-butyl or t-butyl. A $C_1$–$C_4$ alkoxy group may similarly be linear or branched, for instance methoxy, ethoxy, n-propoxy, i-propoxy, n-butoxy, s-butoxy or t-butoxy. A halogen is, for example, fluorine, chlorine, bromine or iodine.

In one aspect of the invention the compound is a bis(acridine carboxamide)derivative of the formula (Ia):

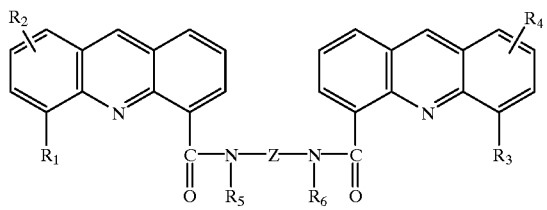

(Ia)

wherein each of $R_1$ and $R_3$, which are the same or different, is $C_1$–$C_4$ alkoxy, $C_1$–$C_4$ alkyl or halogen, each of $R_1$ and $R_4$, which are the same or different, is hydrogen, $C_1$–$C_4$ alkoxy, $C_1$–$C_4$ alkyl or halogen and each of $R_5$ and $R_6$ is H; or a pharmaceutically acceptable salt or N-oxide thereof.

In another aspect of the invention the compound is a bis(phenazinecarboxamide) derivative of formula (Ib):

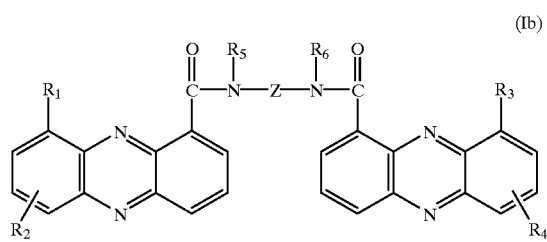

(Ib)

wherein each of $R_1$ and $R_3$, which are the same or different, is $C_1$–$C_4$ alkoxy, $C_1$–$C_4$ alkyl or halogen, each of $R_2$ and $R_4$, which are the same or different, is hydrogen, $C_1$–$C_4$ alkoxy, $C_1$–$C_4$ alkyl or halogen and each of $R_5$ and $R_6$ is H; or a pharmaceutically acceptable salt or N-oxide thereof.

Examples of specific compounds of the invention are depicted in the following Table 1 by means of their substitution patterns. The compounds are all symmetric, which is to say that the left hand tricyclic chromophore is identical to the right hand one. Thus, $R_1$=$R_3$ and $R_2$=$R_4$ in formula (I).

TABLE 1

| No. | $R_{1=R3}$ | $R_2$=$R_4$ | X | Z |
|---|---|---|---|---|
| 1 | 1-Me | H | —CH= | $(CH_2)_3NMe(CH_2)_3$ |
| 2 | 1-Cl | H | —CH= | $(CH_2)_3NMe(CH_2)_3$ |
| 3 | 2-Me | H | —CH= | $(CH_2)_3NMe(CH_2)_3$ |
| 4 | 2-Cl | H | —CH= | $(CH_2)_3NMe(CH_2)_3$ |
| 5 | 3-Me | H | —CH= | $(CH_2)_3NMe(CH_2)_3$ |
| 6 | 5-Me | H | —CH= | $(CH_2)_3NMe(CH_2)_3$ |
| 7 | 5-Et | H | —CH= | $(CH_2)_3NMe(CH_2)_3$ |
| 8 | 5-iPr | H | —CH= | $(CH_2)_3NMe(CH_2)_3$ |
| 9 | 5-Ph | H | —CH= | $(CH_2)_3NMe(CH_2)_3$ |
| 10 | 5-OMe | H | —CH= | $(CH_2)_3NMe(CH_2)_3$ |
| 11 | 5-F | H | —CH= | $(CH_2)_3NMe(CH_2)_3$ |
| 12 | 5-Cl | H | —CH= | $(CH_2)_3NMe(CH_2)_3$ |
| 13 | 5-Br | H | —CH= | $(CH_2)_3NMe(CH_2)_3$ |
| 14 | 5-$CF_3$ | H | —CH= | $(CH_2)_3NMe(CH_2)_3$ |
| 15 | 6-OMe | H | —CH= | $(CH_2)_3NMe(CH_2)_3$ |
| 16 | 6-F | H | —CH= | $(CH_2)_3NMe(CH_2)_3$ |
| 17 | 6-Cl | H | —CH= | $(CH_2)_3NMe(CH_2)_3$ |
| 18 | 6-Br | H | —CH= | $(CH_2)_3NMe(CH_2)_3$ |
| 19 | 6-$CF_3$ | H | —CH= | $(CH_2)_3NMe(CH_2)_3$ |
| 20 | 6-$NMe_2$ | H | —CH= | $(CH_2)_3NMe(CH_2)_3$ |
| 21 | 7-Me | H | —CH= | $(CH_2)_3NMe(CH_2)_3$ |
| 22 | 7-Et | H | —CH= | $(CH_2)_3NMe(CH_2)_3$ |
| 23 | 7-iPr | H | —CH= | $(CH_2)_3NMe(CH_2)_3$ |
| 24 | 7-tBu | H | —CH= | $(CH_2)_3NMe(CH_2)_3$ |
| 25 | 7-Ph | H | —CH= | $(CH_2)_3NMe(CH_2)_3$ |
| 26 | 7-OMe | H | —CH= | $(CH_2)_3NMe(CH_2)_3$ |

TABLE 1-continued

| No. | $R_{1=R3}$ | $R_2$=$R_4$ | X | Z |
|---|---|---|---|---|
| 27 | 7-F | H | —CH= | $(CH_2)_3NMe(CH_2)_3$ |
| 28 | 7-Cl | H | —CH= | $(CH_2)_3NMe(CH_2)_3$ |
| 29 | 7-Br | H | —CH= | $(CH_2)_3NMe(CH_2)_3$ |
| 30 | 8-Me | H | —CH= | $(CH_2)_3NMe(CH_2)_3$ |
| 31 | 8-Cl | H | —CH= | $(CH_2)_3NMe(CH_2)_3$ |
| 32 | 5-Me | 7-Me | —CH= | $(CH_2)_3NMe(CH_2)_3$ |
| 33 | H | H | —CH= | $(CH_2)_3NMe(CH_2)_3$ |
| 34 | H | H | —CH= | $(CH_2)_2NH(CH_2)_2$ |
| 35 | H | H | —CH= | $(CH_2)_3NH(CH_2)_3$ |
| 36 | H | H | —CH= | $(CH_2)_3NpipN(CH_2)_3$ |
| 37# | H | H | —CH= | $(CH_2)_3NMe(CH_2)_3$ |
| 38 | H | H | —N= | $(CH_2)_3NMe(CH_2)_3$ |
| 39# | H | H | —N= | $(CH_2)_3NMe(CH_2)_3$ |
| 40 | 6-Me | H | —N= | $(CH_2)_3NMe(CH_2)_3$ |
| 41 | 6-Cl | H | —N= | $(CH_2)_3NMe(CH_2)_3$ |
| 42 | 7-Me | H | —N= | $(CH_2)_3NMe(CH_2)_3$ |
| 43 | 7-OMe | | —N= | $(CH_2)_3NMe(CH_2)_3$ |
| 44 | 7-Cl | H | —N= | $(CH_2)_3NMe(CH_2)_3$ |
| 45 | 8-Me | H | —N= | $(CH_2)_3NMe(CH_2)_3$ |
| 46 | 8-OMe | H | —N= | $(CH_2)_3NMe(CH_2)_3$ |
| 47 | 9-Me | H | —N= | $(CH_2)_3NMe(CH_2)_3$ |
| 48 | 9-Me | H | —N= | $(CH_2)_3NpipN(CH_2)_3$ |
| 49 | 9-Me | H | —N= | $(CH_2)_2NH(CH_2)_2NH(CH_2)_2$ |
| 50 | 9-OMe | H | —N= | $(CH_2)_3NMe(CH_2)_3$ |
| 51 | 9-OPh | H | —N= | $(CH_2)_3NMe(CH_2)_3$ |
| 52 | 9-F | H | —N= | $(CH_2)_3NMe(CH_2)_3$ |
| 53 | 9-Cl | H | —N= | $(CH_2)_3NMe(CH_2)_3$ |
| 54 | 9-$NMe_2$ | H | —N= | $(CH_2)_3NMe(CH_2)_3$ |
| 55 | 5-$NMe_2$ | H | —CH= | $(CH_2)_3NMe(CH_2)_3$ |
| 56 | 7-$NMe_2$ | H | —CH= | $(CH_2)_3NMe(CH_2)_3$ |
| 57 | 5-Me | 8-Me | —CH= | $(CH_2)_3NMe(CH_2)_3$ |
| 56 | 1-Me | 5-Me | —CH= | $(CH_2)_3NMe(CH_2)_3$ |
| 59 | 8-Cl | 5-Me | —CH= | $(CH_2)_3NMe(CH_2)_3$ |
| 60 | 1-Cl | 5-Me | —CH= | $(CH_2)_3NMe(CH_2)_3$ |
| 61 | 3-Me | H | —N= | $(CH_2)_3NMe(CH_2)_3$ |
| 62 | 3-Cl | H | —N= | $(CH_2)_3NMe(CH_2)_3$ |
| 63 | 2-Cl | H | —N= | $(CH_2)_3NMe(CH_2)_3$ |
| 64 | 8-Cl | H | —N= | $(CH_2)_3NMe(CH_2)_3$ |
| 65 | 6-Me | 9-Me | —N= | $(CH_2)_3NMe(CH_2)_3$ |
| 66 | 6-Cl | 9-Me | —N= | $(CH_2)_3NMe(CH_2)_3$ |
| 67 | 4-Me | H | —N= | $(CH_2)_3NMe(CH_2)_3$ |
| 68 | 9-Me | H | —N= | $(CH_2)_3NH(CH_2)_2NH(CH_2)_3$ |
| 69 | 6-Me | 9-Me | —N= | $(CH_2)_3NH(CH_2)_2NH(CH_2)_2$ |
| 70 | 9-Me | H | —N= | $(CH_2)_3NH(CH_2)_4NH(CH_2)_3$ |
| 71 | 5-Me | H | —CH= | $(CH_2)_2NH(CH_2)_2NH(CH_2)_2$ |
| 72 | H | H | —CH= | $(CH_2)_2NH(CH_2)_2NH(CH_2)_2$ |
| 73 | 9-Me | H | —N= | $(CH_2)_3NH(CH_2)_3NH(CH_2)_2$ |
| 74 | 6-Cl | 9-Me | —N= | $(CH_2)_2NH(CH_2)_2NH(CH_2)_2$ |
| 74a | 9-Me | H | —N= | $(CH_2)_2NMe(CH_2)_2NMe(CH_2)_2$ |

| No. | chromophore | Z | chromophore |
|---|---|---|---|
| 75 | acridine-4-carboxamide | $(CH_2)_3NMe(CH_2)_3$ | phenazine-1-carboxamide |
| 76 | 5-methylacridine-4-carboxamide | $(CH_2)_3NMe(CH_2)_3$ | 9-methylphenazine-1-carboxamide |
| 77 | phenazine-1-carboxamide | $(CH_2)_3NMe(CH_2)_3$ | 9-methylphenazine-1-carboxamide |
| 78 | 5-methylacridine-4-carboxamide | $(CH_2)NH(CH_2)_2$—$NH(CH_2)_2$ | 9-methylphenazine-1-carboxamide |
| 79 | acridine-4-carboxamide | $(CH_2)_2NH(CH_2)_2$—$NH(CH_2)_2$ | phenazine-1-carboxamide | denotes carboxamide at 2-position of acridine or phenazine. In all other cases the carboxamide is at the 4-position in acridines (X is —CH=) and the 1-position in phenazines (X is —N=).

The compounds of formula (I) and their pharmaceutically acceptable acid addition salts and N-oxides are produced by a process which comprises reacting two moles of an acridinecarboxylic acid or 9-azaacridinecarboxylic acid (phenazinecarboxylic acid) derivative of the formula (II):

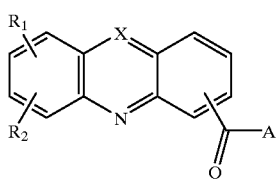

wherein $R_1$, $R_2$ and X are defined as above and A is OH, Cl, or N-imidazolyl, with one mole of a bis(amine) of formula (III):

wherein $R_5$, $R_6$ and Z are as defined as above, and, if desired, converting the resulting compound into a pharmaceutically acceptable acid addition salt or N-oxide thereof. This coupling reaction is typically performed in a non-hydroxylic solvent, preferably THF. The reaction is conveniently performed at a temperatures of from $-10°$ C. to $50°$ C.

The derivatives of formula (I) may be converted into pharmaceutically acceptable acid addition salts, and salts may be converted into the free compound, by conventional methods. For instance, the acid addition salts may be prepared by contacting the free base with an appropriate amount of the desired acid in a conventional manner. Suitable salts include salts with both organic and inorganic acids. Examples of suitable acids are hydrochloric, sulfuric, phosphoric, acetic, citric, oxalic, malonic, salicylic, malic, fumaric, succinic, ascorbic, methanesulfonic and the like.

Depending on structure, and on the conditions, the compounds may form multicationic forms.

The optional conversion of a compound of formula (I) into another compound of formula (I) may be carried out by conventional methods. For instance, a fluoro group in a compound of formula may be substitued by an amino or thiol group to give an amine or thioether, respectively; a phenol or thiol group in a compound of formula (I) may be alkylated to give an ether or thioether, respectively; an amino group may be acylated to give an N-acetate; and a nitro group may be reduced to give an amine. These are all routine conversions in organic chemistry.

Compounds of formula (I) may be converted into the corresponding N-oxide by conventional techniques, for instance by dissolving them in $CH_2Cl_2$ and treating with 2-(phenylsulphonyl)-3-phenyloxaridine for 15 mins to 24 hours, preferably for 1 hour, at a temperature of from $0°$ to $60°$, preferably $20°$ C. The free base forms can be regenerated by treating the salt form with a base. The free base forms differ from their respective salt forms in certain physical properties, but are otherwise equivalent to the respective free base forms for the purposes of the invention.

The bis(amines) of general formula (III) are known compounds, and are commercially available or preparable by methods described in the literature. Specific examples of such compounds include $NH_2(CH_2)_6NH_2$, $NH_2(CH_2)_3O(CH_2)_3NH_2$, $NH_2(CH_2)_3NH(CH_2)_3NH_2$, $NH_2(CH_2)_3NMe(CH_2)_3NH_2$, $NH_2(CH_2)_2NH(CH_2)_2NH(CH_2)_2NH_2$ and $NH_2(CH_2)_3N(CH_2CH_2)_2N(CH_2)_3NH_2$.

The substituted acridine acids of formula II wherein X is CH and A is OH can be prepared by a process described in Atwell et al., *J. Med. Chem.*, 1984, 27, 1481. This involves Al/Hg reduction of the corresponding acridone-4-carboxylic acids of formula IV followed by re-oxidation with $FeCl_3$ or other suitable mild oxidant as depicted in scheme 1 below.

Scheme 1

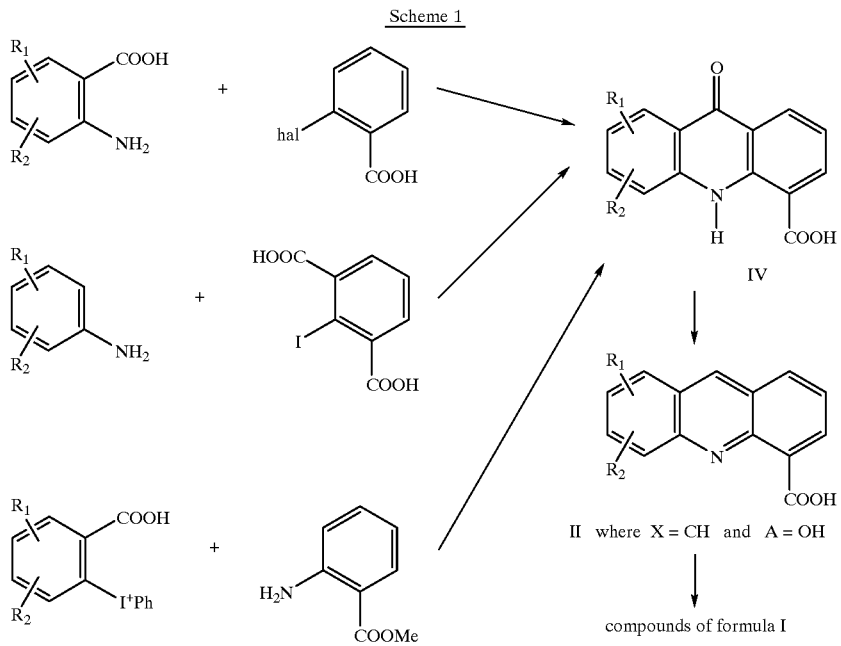

The acridone-4-carboxylic acids of formula IV can in turn be prepared by a variety of known methods, including Jourdan-Ullman coupling of substituted anthranilic acids and haloacids as described in Denny et al., *J. Med. Chem.*, 1987, 30, 658, Jourdan-Ullman coupling of iodoisophthalic acid with substituted anilines as described in Rewcastle and Denny, *Synthesis,* 1985, 217 or reaction of substituted diphenyliodonium carboxylates with substituted anilines as described in Rewcastle and Denny, *Synthesis,* 1985, 220, followed by cyclization of the diphenylamine diacids and diphenylamine monoesters so formed with PPA or PPE to give the acridones. Reaction of the acridine-4-carboxylic acids of formula II wherein A is OH with 1.1 equivalents of 1,1'-carbonyldiimidazole in DMF at 10–40° C. for 10 min to 24 h gives the corresponding imidazolide derivatives of compounds of formula II. These can be isolated by filtration and reacted with 0.5 equivalents of a bisamine of formula III to give the required compounds of formula I.

Some of the substituted acridine-4-carboxylic acids of formula (II) and derivatives thereof, useful as intermediates in the preparation of compounds of general formula (I), are novel. Accordingly, the invention further provides a compound of formula (IIa):

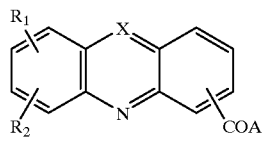

(IIa)

wherein X, $R_1$ and $R_2$ are as defined for formula (I) and A is OH, Cl, N-imidazolyl or OR wherein R is branched or unbranched, saturated or unsaturated $C_1$–$C_6$ alkyl, or aryl, with the exception of compounds wherein:

(i) X is CH, A is OH, one of $R_1$ and $R_2$ is H and the other is H, Cl, OMe or Me and the —COA moiety is at the 4-position of the tricyclic chromophore; and (ii) X is N, A is OH, one of $R_1$ and $R_2$ is H and the other is H, Cl, OMe or Me and the COA moiety is at the 1-position of the tricyclic chromophore.

These novel compounds of formula (IIa) can be prepared by the process which is depicted fully in Scheme 2 below. Accordingly, the invention further provides a process for producing a compound of formula (IIa), which process comprises cyclizing a compound of formula (X):

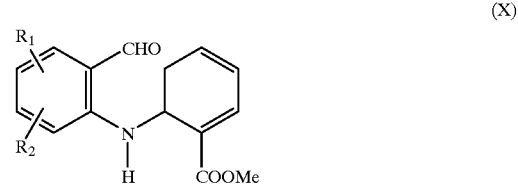

(X)

wherein $R_1$ and $R_2$ are as defined above. The cyclization is typically carried out under acid conditions, for example using neat trifluoroacetic acid for a period of 12 hours, at a temperature of from 20° to 60° C.

The compounds of formula (X) are produced as indicated in scheme 2 below.

Scheme 2

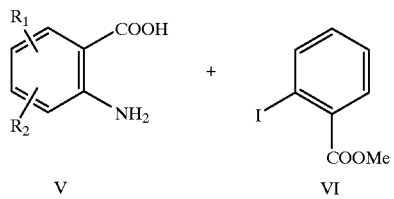

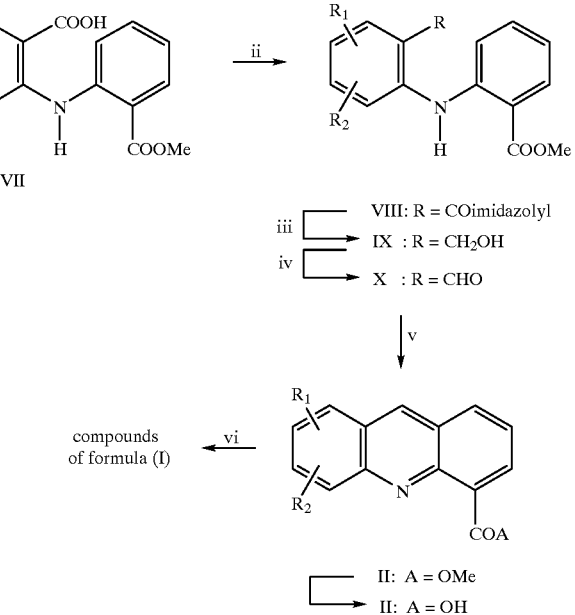

Throughout scheme 2, $R_1$ and $R_2$ are as defined above for general formula (I). The substituted diphenylamine acids (VII) are formed by coupling of substituted anthranilic acids (V) with methyl 2-halobenzoates (VI), typically the iodobenzoate and a copper catalyst in a polar solvent, typically butane-2,3-diol. This is described in Rewcastle and Denny, *Synth. Comm.*, 1987, 17, 309. Reaction of the substituted diphenylamine acids with 1,1'-carbonyldiimidazole (CDI) in a polar solvent, typically THF, gives the imidazolides of formula (VIII), which are reduced in situ by excess of a metal-based reducing agent suitably sodium borohydride to the alcohols of formula (IX).

Oxidation of the alcohols with solid $MnO_2$ in a polar solvent, typically ethyl acetate or acetone, gives the corresponding aldehydes of formula (X), which are cyclized as indicated above to form substituted acridine esters, which are compounds of formula (II) wherein A is OMe. These esters can be hydrolyzed under acidic or basic conditions to the corresponding acids, which are compounds of formula (II) wherein A is OH. These in turn can be activated by reaction with 1,1'-carbonyldiimidazole in a polar solvent (preferably dry DMF) to give the corresponding imidazolide derivative, which are compounds of formula (IIa) wherein A is N-imidazolyl, or by treatment with thionyl chloride in an inert solvent, typically dichloroethane, to give the corresponding acid chlorides which are compounds of formula (II) wherein A is Cl.

These latter intermediates can be coupled with bis (amines) of formula (III) as described above, to give the desired compounds of general formula (I). Alternatively, the substituted acridine esters of formula(II wherein A=OMe can be reacted directly with bis(amines) of general formula III in a polar solvent, preferably ethanol or isopropanol, to give the compounds of general formula (I).

The phenazine acids, namely compounds of formula II wherein X is N and A is OH, can be prepared by methods reported in the literature. Examples include *J. Med. Chem.* 1987, 30, 843; Synth. Comm. 1987, 17, 1171; EP-A-172, 744, and *Chem. Abstr.* 1986, 105, 97496p. These may then be converted to compounds of general formula I by the methods outlined above.

Further compounds of general formula (I) can also be made by the general method outlined in Scheme 3 which follows. In this approach, reaction of compounds of formula (II) (where A=imidazolide) with a mono-protected amine of formula (XI) gives an intermediate of formula (XII). Removal of the $R_8$ protecting group gives amines of formula (XIII), which can be coupled with a further equivalent of a compound of formula (II) (where A=imidazolide) to give compounds of formula (I). In Scheme 3, $R_1$–$R_5$, Z and $R_6$ are as defined above for formula (I), with the exception that $R_7$ can also be BOC, trityl, $CO_2CF_3$ or other suitable amine protecting group, and $R_8$ is defined as BOC, trityl, $CO_2CF_3$ or other suitable amine protecting group.

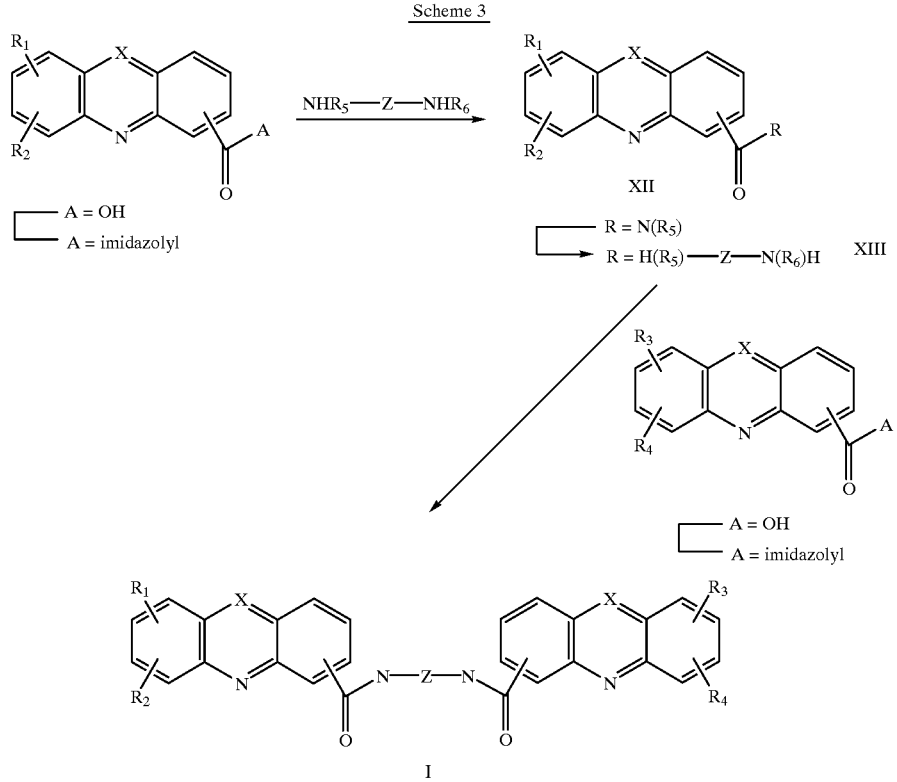

Scheme 3

The compounds of formula (I) and their salts and N-oxides have been found in biological tests to have anti-tumor activity. The results are set out in Example 78 which follows. The compounds have negligible toxicity and may therefore be used as anti-tumor agents. A human or animal patient harbouring a tumor may thus be treated by a method which comprises administering thereto a compound of formula (I) or a salt or N-oxide thereof. The condition of a patient suffering from cancer may thereby be improved. Examples of tumors which the compounds of formula (I) may be used to treat include lung and colon tumors, melanoma and central nervous system (CNS) tumors.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 50 mg/m$^2$ to 5 g/m$^2$. Such a dosage may be given, for example, from 1 to 5 times daily by bolus infusion, for instance 3 times daily, infusion over several hours, for instance 3 hours, and/or repeated administration.

The present compounds of formula (I) and their salts and N-oxides are formulated for use as a pharmaceutical or veterinary composition . The present invention therefore further provides a pharmaceutical or veterinarily composition which comprises a pharmaceutically or veterinarily acceptable carrier or diluent and, as an active ingredient, a compound of formula (I) or a salt or N-oxide thereof.. The compositions are typically prepared following conventional methods and are administered in a pharmaceutically or veterinarily suitable form.

For example, the solid oral forms may contain, together with the active compound, diluents, such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures, dye-stuffs; sweeteners; wetting agents such as lecithin, polysorbates, laurylsulphates. Such preparations may be manufactured in known manner, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular a syrup may contain as carrier, for example, saccharose or saccharose with glycerol and/or mannitol and/or sorbitol. In particular a syrup for diabetic patients can contain as carriers only products, for example sorbitol, which do not metabolize to glucose or which only metabolize a very small amount to glucose. The suspensions and the emulsions may contain as carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and if desired, a suitable amount of lidocaine hydrochloride. Typically the compounds of formula (I) are formulated as aqueous solutions of hydrochloride or other pharmaceutically acceptable salts. Solutions for intravenous injection or infusion may contain a carrier, for example, sterile water which is generally Water for Injection.

The invention will be further described in the following Examples, with reference to the accompanying Figure, in which:

EXAMPLE 1

Figure 1:
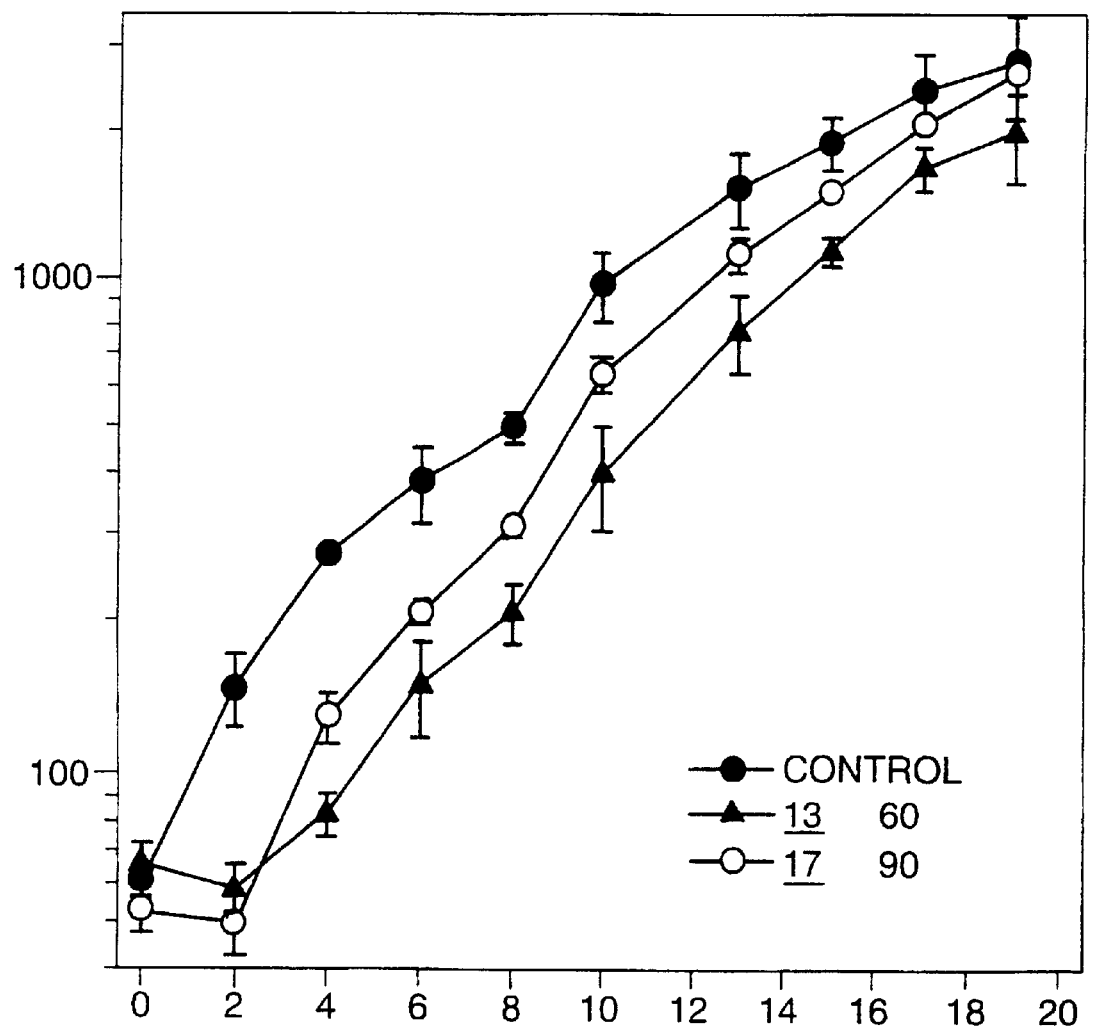
FIG. 1 is a plot of tumor volume in mm$^3$ (y axis) against time in days (x axis) for the growth delay of colon 38 tumor cells in in vivo testing in mice, as described in Example 80 which follows.

Preparation of Compound 22 of Table I by the Method of Scheme 1

A mixture of 2-iodoisophthalic acid (2.92 g, 10 mmol), 4-ethylaniline (1.82 g, 15 mmol), CuCl (1 g), 2,3-butanediol (12 mL) and benzene (10 mL) was heated and stirred with the benzene being allowed to distil off. When the internal temperature of the reaction mixture reached 100° C., N-ethylmorpholine (6 mL) was added, and the reaction mixture was stirred for an additional 4 hours at 120° C. The reaction mixture was then diluted with 0.5 M NH$_4$OH (50 mL), treated with charcoal and filtered through Celite. Acidification with 2 M HCl afforded a precipitate which was extracted into EtOAc (2×100 mL), filtered through Celite and further extracted with 0.5M NH$_3$ (100 mL). Acidification with concentrated HCl and recrystallization of the isolated product gave 2-[(4-ethyl)phenylamino]isophthalic acid (2.36 g, 83%), mp (EtOAc/pet. ether) 194.0–195.4° C. $^1$H NMR [(CD$_3$)$_2$SO] δ 1.15 (t, J=7.6, 3 H, CH$_3$), 2.51 (q, J=7.6 Hz, 2 H, CH$_2$), 6.84 (d, J=8.4 Hz, 2 H, H-2' and H-6' or H-3' and H-5'), 6.97 (t, J=7.7 Hz, 1 H, H-5), 7.04 (d, J=8.4 Hz, 2 H, H-3' and H-5' or H-2' and H-6'), 7.92 (d, J=7.6 Hz, 2 H, H-4 and H-6), 9.65 (br s, 1 H, NH) and 12.90 (br s, 2 H, 2×COOH). Anal. (C$_{16}$H$_{14}$NO$_4$) C, H, N.

Reaction of the above diacid (1.43 g, 5 mmol) with polyphosphoric acid (38 g) was achieved by heating the mixture at 120° C. for 2 h. The cooled mixture was poured into boiling water (250 mL), resulting in a suspension of yellow precipitate. The precipitate was removed by filtration and dissolved in a mixture of MeOH (100 mL) and 1M NaOH (100 mL) which was heated and then filtered whilst still hot. Acidification of this mixture using glacial acetic acid gave a yellow solid, which was recrystallized to give 7-ethyl-9-oxoacridan-4-carboxylic acid (1.14, g, 89%), mp (H$_2$O) 301° C. (dec). $^1$H NMR [(CD$_3$)$_2$SO] δ 1.26 (t, J=7.6 Hz, 3 H, CH$_3$), 2.74 (q, J=7.6 Hz, 2 H, CH$_2$), 7.33 (t, J=7.7 Hz, 1 H, H-2), 7.64 (dd, J=8.5, 2.1 Hz, 1 H, H-6), 7.71 (d, J=8.5 Hz, 1 H, H-5), 8.04 (br s, 1 H, H-8), 8.42 (dd, J=7.5, 1.7 Hz, 1 H, H-3), 8.52 (dd, J=8.0, 1.7 Hz, 1 H, H-1), 11.98 (s, 1 H, NH) and 13.85 (br s, 1 H, COOH). Anal. (C$_{16}$H$_{13}$NO$_3$) C, H, N.

A suspension of the above acridone acid (1.00 g, 3.75 mmol) in 50% aqueous EtOH was stirred and heated, then sufficient triethylamine added to obtain a clear yellow solution. Portions of aluminium foil (0.83 g) were amalgamated in a solution of HgCl$_2$ (3 g) in EtOH, then added to the above vigorously boiling solution over 30 min. After the reaction was observed to be complete by tlc, the reaction mixture was filtered and the solids collected were washed with a solution of KOH in aqueous EtOH. The filtrate was then strongly acidified with concentrated HCl and treated with FeCl$_3$ under reflux for 45 min. The reaction mixture was concentrated under reduced pressure and sufficient potassium acetate added until the pH was neutral. Crystallization of the product occurred upon cooling and filtration and recrystalisation of the resulting brown solid gave 7-ethylacridine-4-carboxylic acid (0.77 g, 82%), mp (acetone) 210–211.5° C. $^1$H NMR [(CD$_3$)$_2$SO] δ 1.35 (t, J=7.5 Hz, 3 H, CH$_3$), 2.91 (q, J=7.5 Hz, 2 H, CH$_2$), 7.83 (dd, J=8.3, 7.2 Hz, 1 H, H-2), 7.97 (dd, J=9.0. 1.9 Hz, 1 H, H-6), 8.09 (br s, 1 H, H-8), 8.26 (d, J=9.0 Hz, 1 H, H-5), 8.54 (dd, J=8.4, 1.2 Hz, 1 H, H-1), 8.71 (br d, J=7.0 Hz, 1 H, H-3), 9.43 (s, 1 H, H-9), 17.09 (br s, 1 H, COOH). Anal. (C$_{16}$H$_{13}$NO$_2$) C, H, N.

The above acridine acid (0.30 g, 1.2 mmol) was reacted with CDI (0.38 g, 2.39 mmol) in dry DMF (50 mL) for 4 h at 50° C. The DMF was removed under reduced pressure, and the resulting oil was dissolved in a mixture of petroleum ether and $CH_2Cl_2$ (20 mL, 3:1). Upon cooling, the imidazolide crystallized out and this crude material was used in the following coupling reaction. The coupling reaction was carried out by dissolving 3,3'-diamino-N-methyldipropylamine (0.09 g) in THF (50 mL), cooling to 0° C. (ice/water), and adding the crude imidazolide portionwise. The reaction mixture was allowed to stir overnight at room temperature, the THF removed, and the residue diluted with $CH_2Cl_2$ (100 mL) which was subsequently washed with 1M $Na_2CO_3$ (50 mL). The $CH_2Cl_2$ layer was dried with $Na_2SO_4$, the solvent removed under reduced pressure, and the resulting brown oil purified by chromatography on alumina (0.5% MeOH in $CH_2Cl_2$ as eluant) to give bis[(7-ethylacridine-4-carboxamido)-propyl]methylamine (22) (0.17 g, 47%) as a yellow oil. $^1H$ NMR ($CDCl_3$) δ 1.28 (t, J=7.5 Hz, 6 H, 2×$CH_3$), 2.03–2.11 (m, 4 H, 2×$CH_2CH_2CH_2$), 2.40 (s, 3 H, $NCH_3$), 2.70 (q, J=7.6 Hz, 4 H, 2×$CH_2CH_3$), 2.79 (t, J=7.4 Hz, 4 H, 2×$CH_2NCH_3$), 3.74 (q, J=6.2 Hz, 4 H, 2×$CH_2NH$), 7.46 (br s, 2 H, H-8), 7.48 (dd, J=8.9, 1.8 Hz, 2 H, H-6), 7.56 (dd, J=8.3, 7.2 Hz, 2 H, H-2), 7.89 (d, J=8.8 Hz, 2 H, H-5), 7.98 (dd, J=8.3, 1.5 Hz, 2 H, H-1), 8.51 (s, 2 H, H-9), 8.86 (dd, J=7.1, 1.5 Hz, 2 H, H-3), 11.80 (br t, J=5.0 Hz, 2 H, CONH). HRMS. (FAB$^+$) m/z calcd for $C_{39}H_{42}N_5O_2$ 612.3339 (MH$^+$), found 612.3333.

EXAMPLE 2

Preparation of Compound 1 of Table I by the Method of Scheme 1

Activation and coupling of the known [Atwell et al., *J. Med. Chem.* 1987, 30, 664] 1-methylacridine-4-carboxylic acid gave bis[(1-methylacridine-4-carboxamido)propyl] methylamine (1) as a yellow oil (91%). $^1H$ NMR ($CDCl_3$) δ 2.02–2.09 (m, 4 H, 2×$CH_2CH_2CH_2$), 2.38 (s, 3 H, $NCH_3$), 2.75 (t, J=7.5 Hz, 4 H, 2×$CH_2NCH_3$), 2.80 (d, J=0.7 Hz, 6 H, 2$CH_3$), 3.73 (q, J=6.1 Hz, 4 H, 2×$CH_2NH$), 7.36 (ddd, J=8.2, 6.7, 0.9 Hz, 2 H, H-6 or H-7), 7.43 (dd, J=7.6, 0.8 Hz, 2 H, H-2), 7.66 (ddd, J=8.7, 6.7, 1.4 Hz, 2 H, H-7 or H-6), 7.80 (d, J=8.0 Hz, 2 H, H-5 or H-8), 7.99 (dd, J=8.7, 0.8 Hz, 2 H, H-8 or H-5), 8.78 (s, 2 H, H-9), 8.80 (d, J=7.3 Hz, 2 H, H-3) and 11.77 (br t, J=5.1 Hz, 2 H, 2NH). HRMS (FAB$^+$) m/z calcd. for $C_{37}H_{38}N_5O_2$ 584.3026 (MH$^+$), found 584.3041. Anal. ($C_{37}H_{37}N_5O_2 \cdot 0.5H_2O$) C, H, N.

EXAMPLE 3

Preparation of Compound 2 of Table I by the Method of Scheme 1

Activation and coupling of the known [Atwell et al., *J. Med. Chem.* 1987, 30, 664] 1-chloroacridine-4-carboxylic acid gave bis[(1-chloroacridine-4-carboxamido)propyl] methyl-amine (2) (83%), mp ($CH_2Cl_2$/n-hexane) 94–96° C. $^1H$ NMR ($CDCl_3$) δ 2.02–2.09 (m, 4 H, 2×$CH_2CH_2CH_2$), 2.39 (s, 3 H, $NCH_3$), 2.79 (t, J=7.4 Hz, 4 H, 2×$CH_2NCH_3$), 3.72 (q, J=6.1 Hz, 4 H, 2×$CH_2NH$), 7.31 (ddd, J=8.2, 6.7, 0.8 Hz, 2 H, H-6 or H-7), 7.63 (ddd, J=8.7, 6.7, 1.3 Hz, 2 H, H-7 or H-6), 7.67 (d, J=7.9 Hz, 2 H, H-2), 7.74 (br d, J=8.0 Hz, 2 H, H-5 or H-8), 7.91 (br d, J=8.7 Hz, 2 H, H-8 or H-5), 8.75 (d, J=8.0 Hz, 2 H, H-3), 8.98 (s, 2 H, H-9), 11.45 (br t, J=4.8 Hz, 2 H, 2×CONH). HRMS(FAB$^+$) m/z calcd. for $C_{35}H_{32}{}^{35}Cl_2N_5O_2$ 624.1933 (MH$^+$), found 624.1935 Anal. ($C_{35}H_{31}Cl_2N_5O_2$) C, H, N.

EXAMPLE 4

Preparation of Compound 3 of Table I by the Method of Scheme 1

Activation and coupling of the known [Atwell et al., *J. Med. Chem.* 1987, 30, 664] 2-methylacridine-4-carboxylic acid gave bis[(2-methylacridine-4-carboxamido)propyl] methylamine (3) as a yellow oil (90%). $^1H$ NMR ($CDCl_3$) δ 2.01–2.08 (m, 4 H, 2×$CH_2CH_2CH_2$), 2.38 (s, 3 H, $NCH_3$), 2.60 (s, 3 H, 2×$CH_3$), 2.73 (t, J=7.4 Hz, 4 H, 2×$CH_2NCH_3$), 3.70–3.77 (m, 4 H, 2$CH_2NH$), 7.38 (br t, J=7.8 Hz, 2 H, H-6 or H-7) 7.64 (ddd, J=8.6, 6.9, 1.5 Hz, 2 H, H-7 or H-6), 7.76 (br s, 2 H, H-1), 7.79 (d, J=8.3 Hz, 2H, H-5 or H-8), 8.00 (d, J=8.2 Hz, 2 H, H-8 or H-5), 8.55 (s, 2 H, H-9), 8.76 (d, J=2.2 Hz, 2 H, H-3) and 11.79 (br t, J=5.0 Hz, 2 H, 2×CONH). HRMS(FAB$^+$) m/z calcd. for $C_{37}H_{38}N_5O_2$ 584.3026 (MH$^+$), found 584.3031. Anal. ($C_{37}H_{37}N_5O_2$) C, H,N.

EXAMPLE 5

Preparation of Compound 4 of Table I by the Method of Scheme 1

Activation and coupling of the known [Atwell et al, *J. Med Chem.* 1987, 30, 664] 2-chloroacridine-4-carboxylic acid gave bis[2-chloroacridine-4-carboxamido)propyl] methylamine (4) as a yellow solid (54%), mp ($CH_2Cl_2$/n-hexane) 175.5–176.5° C. $^1H$ NMR ($CDCl_3$) δ 2.00–2.07 (m, 4H,2×$CH_2CH_2CH_2$), 2.38 (s, 3H, $NCH_3$), 2.75 (t,J=7.4 Hz, 4H, 2×$CH_2NCH_3$), 3.71 (q, J=6.2 Hz, 4H, 2×$CH_2NH$), 7.42 (ddd, J=8.3, 6.6, 0.9 Hz, 2H, H-6 or H-7), 7.68 (ddd, J=8.7, 6.6, 1.3 Hz, 2H, H-7 or H-6), 7.74 (br d, J=7.9 Hz, 2H, H-5 or H-8), 7.93–7.96 (m, 4H, H-1 and H-8 or H-5), 8.49 (s, 2H, H-9), 8.74 (d, J=2.5 Hz, 2H, H-3) and 11.52 (br t, J=5.0 Hz, 2×NH). HRMS (FAB$^+$) m/z calcd. for $C_{35}H_{32}{}^{35}Cl_2N_5O_2$ 624.1993 (MH$^+$), found 624.1900. Anal ($C_{35}H_{31}Cl_2N_5O_2$) C,H,N.

EXAMPLE 6

Preparation of Compound 5 of Table I by the Method of Scheme 1

Activation and coupling of the known [Atwell et al., *J. Med. Chem.* 1987, 30, 664] 3-methylacridine-4-carboxylic acid, followed by purification on alumina followed by silica gel chromatography, gave bis[(3-methylacridine-4-carboxamido)propyl]methyl-amine (5) as a pale yellow gum (15%). $^1H$ NMR ($CDCl_3$) δ 1.78–1.84 (m, 4 H, 2×$CH_2CH_2CH_2$), 2.18 (s, 3 H, $NCH_3$), 2.48 (s, 6 H, 2×$CH_3$), 2.67 (t, J=6.5 Hz, 4 H, 2×$CH_2NCH_3$), 3.56 (q, J=6.1 Hz, 4 H, 2×$CH_2NH$), 7.19 (d, J=8.6 Hz, 2 H, H-1 or H-2), 7.33 (ddd, J=8.4, 6.6, 1.0 Hz, 2 H, H-6 or H-7), 7.39 (br t, J=5.3 Hz, 2H, 2×NH), 7.58 (ddd, J=8.8, 6.6, 1.4 Hz, 2 H, H-7 or H-6), 7.66 (d, J=8.7 Hz, H-2 or H-1), 7.70 (br d, J=7.9 Hz, 2 H, H-5 or H-8), 7.94 (d, J=8.6 Hz, 2H, H-8 or H-5) and 8.37 (s, 2H, H-9). HRMS (FAB$^+$) m/z calcd for $C_{37}H_{38}N_5O_2$ 584.3026 (MH$^+$), found 584.3016.

EXAMPLE 7

Preparation of Compound 6 of Table I by the Method of Scheme 1

Activation and coupling of the known [Atwell et al., *J. Med. Chem.* 1987, 30, 664] 5-methylacridine-4-carboxylic acid gave bis[(5-methylacridine-4-carboxamido)propyl] methylamine (6) (53%) as a yellow oil. $^1H$ NMR ($CDCl_3$) δ 1.61 (s, 6 H, 2×$CH_3$), 1.97–2.00 (m, 4 H, 2×$CH_2CH_2CH_2$), 2.30 (s, 3 H, $NCH_3$), 2.58 (t, J=7.5 Hz, 4 H, 2×$CH_2NCH_3$), 3.70 (q, J=6.5 Hz, 4 H, 2×$CH_2NH$), 7.37 (dd, J=8.5, 6.8 Hz, 2 H, H-7), 7.57 (br d, J=6.7 Hz, 2 H, H-8), 7.61 (dd, J=8.3, 7.2 Hz, 2 H, H-2), 7.74 (br d, J=8.6 Hz, 2 H, H-6), 8.03 (dd, J=8.4, 1.5 Hz, 2 H, H-1), 8.69 (s, 2 H, H-9), 8.94 (dd, J=7.1, 1.5 Hz, 2 H, H-3), 11.79 (br t, J=5.1 Hz, 2 H, 2×NH). HRMS (FAB$^+$) m/z calcd for $C_{37}H_{38}N_5O_2$ 584.3026 (MH$^+$), found 584.3044.

EXAMPLE 8

Preparation of Compound 7 of Table I by the Method of Scheme 1

Similar reduction of the known [Rewcastle and Denny, Synthesis, 1985, 217] 5-ethyl-9-oxoacridon-4-carboxylic acid as above gave 5-ethylacridine-4-carboxylic acid (79%), mp (acetone) 239–240.5° C. $^1$H NMR [(CD$_3$)$_2$SO] δ 1.43 (t, J=7.5 Hz, 3 H, CH$_3$), 3.27–3.38 (m, 2 H, CH$_2$-obscured by H$_2$O), 7.73 (br t, J=7.2 Hz, 1 H, H-2), 7.87 (br t, J=7.8 Hz, 1 H, H-7), 7.93 (br d, J=6.6 Hz, 1 H, H-1), 8.19 (br d, J=8.4 Hz, 1 H, H-6), 8.57 (br d, J=8.2 Hz, 1 H, H-8), 8.76 (br d, J=6.9 Hz, 1 H, H-3), 9.54 (s, 1 H, H-9) and 17.44 (br s, 1, COOH). Anal. (C$_{16}$H$_{13}$NO$_2$) C, H, N.

Activation and coupling of this as above gave bis[(5-ethylacridine-4-carboxamido)propyl]-methylamine (7) (57%) as a yellow oil. $^1$H NMR [CDCl$_3$] δ 1.42 (t, J=7.5 Hz, 6 H, 2×CH$_3$), 1.97–2.04 (m, 4 H, 2×CH$_2$CH$_2$CH$_2$), 2.32 (s, 3 H, NCH$_3$), 2.61 (t, J=7.4 Hz, 4 H, 2×CH$_2$NCH$_3$), 3.24 (q, J=7.5 Hz, 4 H, 2×CH$_2$CH$_3$), 3.69 (q, J=6.2 Hz, 4 H, 2×CH$_2$NH), 7.40 (dd, J=8.4, 6.8 Hz, 2 H, H-7), 7.53 (dd, J=6.7 Hz, 1.0, 2 H, H-6), 7.60 (dd, J=8.3, 7.1 Hz, 2 H, H-2), 7.74 (dd, J=8.2, 1.0 Hz, 2 H, H-8), 8.02 (dd, J=8.4, 1.5 Hz, 2 H, H-1), 8.69 (s, 2 H, H-9), 8.93 (dd, J=7.1, 1.6 Hz, 2 H, H-3) and 11.77 (br t, J=5.5 Hz, 2×CONH). HRMS (FAB$^+$) m/z calcd for C$_{39}$H$_{42}$N$_5$O$_2$ 612.3339 (MH$^+$), found 612.3343.)

EXAMPLE 9

Preparation of Compound 8 of Table I by the Method of Scheme 1

Similar reaction of 2-iodoisophthalic acid and 2-isopropylaniline gave 2-[(2-isopropyl)phenylamino]-isophthalic acid (38%), mp (EtOAc/petroleum ether) 217–219° C. $^1$H NMR [(CD$_3$)$_2$SO] δ 1.25 (d, J=6.8 Hz, 6 H, 2×CH$_3$), 3.22–3.29 (m, 1 H, CH), 6.81 (dd, J=7.4, 1.8 Hz, 1 H, H-3' or H-6'), 6.93 (t, J=7.7 Hz, 1 H, H-2), 6.92–7.02 (m, 2 H, H-4' and H-5'), 7.26 (dd, J=7.1, 2.2 Hz, 1 H, H-6' or H-3'), 7.90 (d, J=7.7 Hz, 2 H, H-4 and H-6), 9.69 (s, 1 H, NH), 12.93 (br s, 2 H, 2×COOH). Anal. (C$_{17}$H$_{17}$NO$_4$) C, H, N.

Cyclization of this as above gave 5-isopropyl-9-oxoacridan-4-carboxylic acid (91%), mp (H$_2$O) 304° C. (dec). $^1$H NMR [(CD$_3$)$_2$SO] δ 1.42 (d, J=6.8 Hz, 6 H, 2×CH$_3$), 3.29–3.41 (m, 1 H, CH), 7.31–7.40 (m, 2 H, H-2 and H-7), 7.74 (dd, J=7.4, 1.2 Hz, 1 H, H-6), 8.15 (dd, J=8.1, 1.2 Hz, 1 H, H-8), 8.47 (dd, J=7.6, 1.6 Hz, 1 H, H-3), 8.53 (dd, J=8.0, 1.6 Hz, 1 H, H-1), 12.48 (s, 1 H, NH), 14.07 (br s, 1 H, COOH). Anal. (C$_{17}$H$_{15}$NO$_3$.0.25 H$_2$O). C, H, N.

Reduction of this as above gave 5-isopropylacridine-4-carboxylic acid (70%), mp (acetone) 238° C. (dec). $^1$H NMR [(CD$_3$)$_2$SO] δ 1.45 (d, J=6.8 Hz, 6 H, 2×CH$_3$), 3.94–4.05 (m, 1 H, CH), 7.75 (dd, J=8.4, 7.1 Hz, 1 H, H-2 or H-7), 7.86 (dd, J=8.4, 7.1 Hz, 1 H, H-7 or H-2), 7.95 (br d, J=6.9 Hz, 1 H, H-6), 8.18 (dd, J=8.4, 1.0 Hz, 1 H, H-8), 8.55 (dd, J=8.4, 1.4 Hz, 1 H, H-1), 8.75 (dd, J=7.1, 1.4 Hz, 1 H, H-3), 9.52 (s, 1 H, H-9), 17.39 (br s, 1 H, COOH). Anal. (C$_{17}$H$_{15}$NO$_2$) C, H, N.

Activation and cyclization of this as above gave bis[(5-isopropylacridine-4-carboxamido)-propyl]methylamine (8) (70%) as a foam. $^1$H NMR (CDCl$_3$) δ 1.47 (d, J=7.0 Hz, 12 H, 4×CH$_3$), 1.96–2.03 (m, 4 H, 2×CH$_2$CH$_2$CH$_2$), 2.32 (s, 3 H, NCH$_3$), 2.59 (t, J=7.4 Hz, 4 H, 2×CH$_2$NCH$_3$), 3.70 (q, J=7.1, 6.3 Hz, 4 H, 2×CH$_2$NH), 4.15–4.18 (m, 2 H, 2×CH), 7.53 (dd, J=8.4, 6.9 Hz, 2 H, H-7), 7.63 (dd, J=8.3, 7.2 Hz, 2 H, H-2), 7.67 (br d, J=6.6 Hz, 2 H, H-6), 7.83 (dd, J=8.4, 1.1 Hz, 2 H, H-8), 8.07 (dd, J=8.3, 1.5 Hz, 2 H, H-1), 8.80 (s, 2 H, H-9), 8.95 (dd, J=7.1, 1.6 Hz, 2 H, H-3), 11.80 (br t, J=5.6 Hz, 2NH). HRMS (FAB$^+$) m/z calcd for C$_{41}$H$_{46}$N$_5$O$_2$ 640.3652 (MH$^+$), found 640.3657. Anal. (C$_{41}$H$_{45}$N$_5$O$_2$) C, H, N.

EXAMPLE 10

Preparation of Compound 9 of Table I by the Method of Scheme 1

Activation and coupling of the known [Atwell et al., J. Med. Chem. 1987, 30, 664] 5-phenylacridine-4-carboxylic acid gave bis[(5-phenylacridine-4-carboxamido)propyl] methylamine (9) (64%) as a yellow oil. $^1$H NMR (CDCl$_3$) δ 1.24–1.26 (m, 4 H, 2×CH$_2$CH$_2$CH$_2$), 2.04 (s, 3 H, NCH$_3$), 2.06–2.10 (br t, J=7.7 Hz, 4 H. 2×CH$_2$NCH$_3$), 3.13 (q, J=7.0, 6.7 Hz, 4 H, 2×CH$_2$NH), 7.43–7.45 (m, 2 H, H-4'), 7.49–7.53 (m, 4 H, H-3' and H-5'), 7.59–7.67 (m, 8 H, H-2, H-2', H6', H-7), 7.75 (dd, J=6.7, 1.4 Hz, 2 H, H-6), 7.99 (dd, J=8.5, 1.3 Hz, 2 H, H-8), 8.09 (dd, J=8.4, 1.5 Hz, 2 H, H-1), 8.88 (s, 2 H, H-9), 8.94 (dd, J=7.2, 1.5 Hz, 2 H, H-3), 11.06 (br t, J=6.0 Hz, 2NH). HRMS (FAB$^+$) m/z calcd for C$_{47}$H$_{42}$N$_5$O$_2$ 708.3339 (MH$^+$), found 708.3345.

EXAMPLE 11

Preparation of Compound 10 of Table I by the Method of Scheme 1

Activation and coupling of the known [Atwell et al., J. Med. Chem. 1987, 30, 664] 5-methoxyacridine-4-carboxylic acid gave bis[(5-methoxyacridine-4-carboxamido)propyl]-methylamine (10) (71%) as a yellow oil. $^1$H NMR (CDCl$_3$) δ 1.99–2.06 (m, 4 H, 2×CH$_2$CH$_2$CH$_2$), 2.38 (s, 3 H, NCH$_3$), 2.72 (t, J=7.6 Hz, 4 H, 2×CH$_2$NCH$_3$), 3.65 (q, J=7.0, 5.2 Hz, 4 H, 2×CH$_2$NH), 3.87 (s, 6 H, 2×OCH$_3$), 6.67 (dd, J=6.5, 2.0 Hz, 2 H, H-6), 7.10–7.16 (m, 4 H, H-7 and H-8), 7.54 (dd, J=8.2, 7.2 Hz, 2 H, H-2), 7.86 (dd, J=8.4, 1.3 Hz, 2 H, H-1), 8.36 (s, 2 H, H-9), 8.82 (dd, J=7.1, 1.5 Hz, 2 H, H-3), 12.04 (br t, J=4.6 Hz, 2 H, 2×CONH). HRMS (FAB$^+$) m/z calcd for C$_{37}$H$_{38}$N$_5$O$_4$ 616.2924 (MH$^+$), found 616.2943.

EXAMPLE 12

Preparation of Compound 11 of Table I by the Method of Scheme 1

Reduction of the known [Rewcastle and Denny, Synthesis, 1985, 217] 5-fluoro-9-oxoacridan-4-carboxylic acid as above gave 5-fluoroacridine-4-carboxylic acid (90%), mp (MeOH/H$_2$O) 295–298° C. (dec). $^1$H NMR [(CD$_3$)$_2$SO] δ 7.74–7.80 (m, 1 H, ArH), 7.90–7.96 (m, 2 H, ArH), 8.19 (d, J=8.6 Hz, 1 H, ArH), 8.61 (dd, J=8.6, 1.2 Hz, 1 H. ArH), 8.81 (dd, J=7.0, 1.0 Hz, 1 H, ArH), 9.65 (s, 1 H, H-9). Anal. (C$_{14}$H$_8$FNO$_2$) C, H, N, F.

Activation and coupling of this as above gave bis[(5-fluoroacridine-4-carboxamido)propyl]-methylamine (11) (96%), mp (HCl salt) 188° C. (dec). $^1$H NMR (CDCl$_3$) δ 2.06 (quin, J=7.2 Hz, 4 H, 2×CH$_2$CH$_2$CH$_2$), 2.38 (s, 3 H, CH$_3$), 2.73 (t, J=7.6 Hz, 4 H, 2×CH$_2$NCH$_3$), 3.72 (q, J=6.3 Hz, 4 H, 2×CH$_2$NH), 7.26 (m, 4 H, ArH), 7.56 (m, 2 H, ArH),7.59 (dd, J=8.4, 7.2 Hz, 2 H, H-2), 7.99 (dd, J=8.4 1.4 Hz, 2 H, H-1), 8.64 (d, J=0.6 Hz, 2 H, H-9), 8.93 (dd, J=7.1, 1.5 Hz, 2 H, H-3), 11.61 (t, J=4.57 Hz, 2 H CONH).

EXAMPLE 13

Preparation of Compound 12 of Table I by the Method of Scheme 1

Activation and coupling of the known [Atwell et al., J. Med. Chem. 1987, 30, 664] 5-chloroacridine-4-carboxylic acid gave bis[(5-chloroacridine-4-carboxamido)propyl] methylamine (12) (62%) as a yellow oil. $^1$H NMR (CDCl$_3$) δ 2.01–2.05 (m, 4 H, 2×CH$_2$CH$_2$CH$_2$), 2.33 (s, 3 H, NCH$_3$), 2.64 (t, J=7.5 Hz, 4 H, 2×CH$_2$NCH$_3$), 3.72 (q, J=6.4, Hz, 4 H, 2×CH$_2$NH), 7.33 (dd, J=8.4, 7.3 Hz, 2 H, H-7), 7.58 (dd, J=8.2, 7.2 Hz, 2 H, H-2), 7.74–7.77 (m, 4 H, H-6 and H-8), 7.96 (dd, J=8.4, 1.5 Hz, 2 H, H-1), 8.64 (s, 2 H, H-9), 8.91 (dd, J=7.1, 1.5 Hz, 2 H, H-3), 11.74 (br t, J=5.3 Hz, 2 H, 2×NH). HRMS (FAB$^+$) m/z calcd for C$_{35}$H$_{32}$$^{35}$Cl$_2$N$_5$O$_2$ 624.1933 (MH$^+$), found 624.1940.

EXAMPLE 14

Preparation of Compound 13 of Table I by the Method of Scheme 1

Reduction of the known [Rewcastle and Denny, *Synthesis*, 1985, 217] 5-bromo-9-oxoacridan-4-carboxylic acid as above gave 5-bromoacridine-4-carboxylic acid (70%), mp (MeOH/H$_2$O) 327° C. (dec). $^1$H NMR [(CD$_3$)$_2$SO] δ 7.71 (dd, J=8.3, 7.4 Hz, 1 H, H-2), 7.94 (dd, J=8.4, 7.1 Hz, 1 H, H-7), 8.40 (dd, J=8.7, 0.8 Hz, 1 H, ArH), 8.50 (dd, J=7.3, 1.0 Hz, 1 H, ArH), 8.64 (dd, J=8.3, 1.3 Hz, 1 H, ArH), 8.85 (dd, J=7.1, 1.3 Hz, 1 H, ArH), 9.66 (s, 1 H, H-9), 16.77 (br s, 1 H, COOH). Anal. (C$_{14}$H$_8$BrNO$_2$) C, H, N, Br.

Activation and coupling of this as above gave bis[(5-bromoacridine-4-carboxamido)propyl]-methylamine (13) (80%), mp (HCl salt) 212–214° C. $^1$H NMR (CDCl$_3$) δ 2.05 (quin, J=7.3 Hz, 4 H, 2×CH$_2$CH$_2$CH$_2$), 2.33 (s, 3 H, CH$_3$), 2.63 (t, J=7.6 Hz, 4 H, 2×CH$_2$NCH$_3$), 3.73 (q, J=6.7 Hz, 4 H, 2×CH$_2$NH), 7.28 (dd, J=8.2, 7.2 Hz, 2 H, H-2), 7.57 (dd, J=8.4, 7.2 Hz, 2 H, H-7), 7.81 (dd, J=8.5, 0.9 Hz, 2 H, H-1), 7.91 (m, 4 H, ArH), 8.64 (s, 2 H, H-9), 8.90 (dd, J=7.1, 1.5 Hz, 2 H, H-3), 11.72 (t, J=5.6 Hz, 2 H,).

EXAMPLE 15

Preparation of Compound 15 of Table I by the Method of Scheme 1

Activation and coupling of the known [Atwell et al., *J. Med. Chem.* 1987, 30, 664] 6-methoxyacridine-4-carboxylic acid gave bis[(6-methoxyacridine-4-carboxamido)propyl]-methylamine (15) (24%), mp (HCl salt) 204–206° C. (dec). $^1$H NMR (CD$_3$)$_2$SO] δ 2.20 (m, 4 H, 2×CH$_2$CH$_2$CH$_2$) 2.85 (d, J=4.65 Hz, 3 H, CH$_3$), 3.59–3.69 (m, 8 H, 4×CH$_2$), 3.95 (s, 6 H, 2×OCH$_3$), 7.17 (d, J=8.9 Hz, 1 H, ArH), 7.57 (br s, 1 H, ArH), 7.64 (t, J=7.7 Hz, 1 H, H-2), 7.70 (d, J=0.8 Hz, 1 H, H-5), 7.97 (d, J=8.35 Hz, 1 H, ArH), 8.25 (d, J=8.35 Hz, 1 H), 8.63 (d, J=6.55 Hz, 1 H, ArH), 9.11 (s, 1 H, H-9), 10.74 (br s, 1 H, NH), 11.21 (br s, 2 H, 2×CONH), 14.43 (br s, 1 H, NH).

EXAMPLE 16

Preparation of Compound 16 of Table I by the Method of Scheme 1

Reduction of 6-fluoro-9-oxoacridan-4-carboxylic acid as above gave 6-fluoroacridine-4-carboxylic acid (91%), mp (MeOH/H$_2$O) 268–270° C. $^1$H NMR [(CD$_3$)$_2$SO] δ 7.76 (td, J=8.9, 2.5 Hz, 1 H, H-7), 7.86 (td, J=8,9, 2.5 Hz, 1 H, H-2), 8.21 (dd, J=10.6, 2.4 Hz, 1 H, H-6), 8.45 (dd, J=9.3, 6.4 Hz, 1 H, H-1), 8.58 (dd, J=8.4 , 1.3 Hz, 1 H, ArH), 8.77 (dd, J=7.1, 1.5 Hz, 1 H, ArH), 9.60 (s, 1 H, H-9), 16.67 (br s, 1 H, COOH).

Activation and coupling of this as above gave bis[(6-fluoroacridine-4-carboxamido)propyl]-methylamine (16) (57%), mp (HCl salt) 165.5° C. (dec). $^1$H NMR (CDCl$_3$) δ 2.04 (quin, J=7.1 Hz, 4 H, 2×CH$_2$CH$_2$CH$_2$), 2.39 (s, 3 H. CH$_3$) 2.72 (t, J=7.4 Hz, 6 H, 2×CH$_2$NCH$_3$), 3.45 (q, J=6.4 Hz, 4 H. 2×CH$_2$NH), 7.28 (ddd, J=9.2, 8.0, 2.4 Hz, 2 H, H-2), 7.62 (dd, J=8.35, 7.2 Hz, 2 H, H-7), 7.69 (dd, J=7.6, 2.4 Hz, 2 H, H-3), 7.89 (dd, J=9.2, 6.1 Hz, 2 H, H-8), 8.05 (dd, J=8.3, 1.5 Hz, 2 H, H-1), 8.74 (s, 2 H, H-9), 8.95 (dd, J=7.2, 1.5 Hz, 2 H, H-5), 11.57 (t, J=4.85 Hz, 2 H, 2×CONH). Anal. (C$_{35}$H$_{31}$F$_2$N$_5$O$_2$.HCl.4H$_2$O) C, H, N,

EXAMPLE 17

Preparation of Compound 17 of Table I by the Method of Scheme 1

Activation and coupling of the known [Atwell et al., *J. Med. Chem.* 1987, 30, 664] 6-chloroacridine-4-carboxylic acid gave bis[(6-chloroacridine-4-carboxamido)propyl] methyl-amine (17) (76%), mp (HCl salt) 216–218° C. $^1$H NMR (CD$_3$)$_2$SO] δ 2.17 (quin, J=6.9 Hz, 4 H, 2×CH$_2$CH$_2$CH$_2$), 2.87 (d, J=4.7 Hz, 3 H, CH$_3$), 3.30 (m, 4 H, 2×CH$_2$), 3.63 (m, 4 H, 2×CH$_2$), 7.47 (dd, J=8.9, 2.0 Hz, 1 H, ArH), 7.69 (t, J=7.7 Hz, 1 H, ArH), 8.06 (d, J=9.0 Hz, 1 H, H-8), 8.28 (dd, J=8.3, 1.3 Hz, 1 H, ArH), 8.38 (d, J=1.7 Hz, 1 H, H-5), 8.64 (dd, J=7.1, 1.3 Hz, 1 H, ArH) 9.16 (s, 1 H, H-9), 10.17 (br s, 1 H, NH), 11.09 (t, J=5.7 Hz, 2 H, 2×NH), 11.44 (br s, 2 H, 2×CONH).

EXAMPLE 18

Preparation of Compound 21 of Table I by the Method of Scheme 1

Activation and coupling of the known [Atwell et al., *J. Med. Chem.* 1987, 30, 664] 7-methylacridine-4-carboxylic acid gave bis[(7-methylacridine-4-carboxamido)propyl] methyl-amine (21) (73%) as a yellow oil. $^1$H NMR (CDCl$_3$) δ 2.03–2.10 (m, 4 H, 2×CH$_2$CH$_2$CH$_2$), 2.34 (s, 6 H, 2×CH$_3$), 2.39 (s, 3 H, NCH$_3$), 2.80 (t, J=7.6 Hz, 4 H, 2×CH$_2$NCH$_3$), 3.73 (q, J=6.1 Hz, 4 H, 2×CH$_2$NH), 7.30 (br s, 2 H, H-8), 7.35 (dd, J=8.8, 1.9 Hz, 2 H, H-6), 7.55 (dd, J=8.4, 7.1 Hz, 2 H, H-2), 7.77 (d, J=8.9 Hz, 2 H, H-5), 7.92 (dd, J=8.4, 1.5 Hz, 2 H, H-1), 8.36 (s, 2 H, H-9), 8.84 (dd, J=7.1, 1.5 Hz, 2H, H-3), 11.74 (br t, J=5.0 Hz, 2 H, 2×CONH. HRMS (FAB$^+$) m/z calcd for C$_{37}$H$_{38}$N$_5$O$_2$ 584.3026 (MH$^+$), found 584.3043.

EXAMPLE 19

Preparation of Compound 23 of Table I by the Method of Scheme 1

Similar reaction of 2-iodoisophthalic acid and 4-isopropylaniline gave 2-[(4-isopropyl)phenylamino] isophthalic acid (62%), mp (EtOAc/petroleum ether) 208° C. (dec). $^1$H NMR [(CD$_3$)$_2$SO] δ 1.16 (d, J=6.9 Hz, 6 H, 2×CH$_3$), 2.78–2.82 (m, 1 H, CH), 6.83 (d, J=8.4 Hz, 2 H, H-2' and H-6' or H-3' and H-5'; 6.97 (t, J=7.7 Hz, 1 H, H-5), 7.07 (d, J=8.5 Hz, 2 H, H-3' and H-5' or H-2' and H-6'), 7.92 (d, J=7.7 Hz, 2 H, H-4 and H-6), 9.66 (br s, 1 H, NH), 12.89 (br s, 2 H, 2×COOH). Anal. (C$_{17}$H$_{17}$NO$_4$) C, H, N.

Cyclization of this as above gave 7-isopropyl-9-oxoacridan-4-carboxylic acid (95%) mp (H$_2$O/MeOH/TEA/AcOH) 289–291° C. $^1$H NMR [(CD$_3$)$_2$SO] δ 1.28 (d, J=6.9 Hz, 6 H, 2×CH$_3$), 3.03–3.07 (m, 1 H, CH), 7.34 (t, J=7.7 Hz, 1 H, H-2), 7.70 (dd, J=8.6, 1.6 Hz, 1 H, H-6), 7.74 (d, J=8.5 Hz, 1 H, H-5), 8.07 (d, J=1.6 Hz, H-8), 8.43 (dd, J=7.5, 1.6 Hz, 1 H, H-3), 8.54 (dd, J=7.9, 1.6 Hz, 1 H, H-1), 11.93 (s, 1 H, NH), 13.80 (br s, 1 H, COOH). Anal. (C$_{17}$H$_{15}$NO$_3$.0.25 H$_2$O) C, H, N.

Reduction of this as above gave 7-isopropylacridine-4-carboxylic acid (51%), mp (acetone) 186–187° C. $^1$H NMR [(CD$_3$)$_2$SO] δ 1.37 (d, J=6.9 Hz, 6 H, 2×CH$_3$), 3.15–3.25 (m, 1 H, CH), 7.84 (dd, J=8.3, 7.2 Hz, 1 H, H-2), 8.03 (dd, J=9.0, 1.8 Hz, 1 H, H-6), 8.11 (br s, 1 H, H-8), 8.27 (d, J=9.0 Hz, 1 H, H-5), 8.54 (dd, J=8.5, 1.0 Hz, 1 H, H-1), 8.73 (dd, J=7.0, 1.2 Hz, 1 H, H-3), 9.45 (s, 1 H, H-9), 17.10 (br s, 1 H COOH). Anal. (C$_{17}$H$_{15}$NO$_2$) C, H, N.

Activation and coupling of this as above gave bis[(7-isopropylacridine-4-carboxamido)-propyl]methylamine (23) (73%) as a yellow oil. $^1$H NMR (CDCl$_3$) δ 1.33 (d, J=6.9 Hz, 12 H, 4×CH$_3$), 2.04–2.08 (m, 4 H, 2×CH$_2$CH$_2$CH$_2$), 2.38 (s, 3 H, NCH$_3$), 2.74 (t, J=7.4 Hz, 4 H, 2×CH$_2$NCH$_3$), 3.03–3.06 (m, 2 H, 2×CH), 3.74 (q, J=6.2 Hz, 4 H, 2×CH$_2$NH), 7.58 (dd, J=8.3, 7.2 Hz, 2 H, H-2), 7.60–7.66 (m, 4 H, H-6 and H-8), 8.01 (d, J=9.5 Hz, 2 H, H-5), 8.03 (dd, J=8.3, 1.5 Hz, 2 H, H-1), 8.66 (s, 2 H, H-9), 8.88 (dd, J=7.2, 1.5 Hz, 2 H, H-3), 11.85 (br t, J=5.1 Hz, 2 H, 2×NH). HRMS (FAB$^+$) m/z calcd for C$_{41}$H$_{46}$N$_5$O$_2$ 640.3652 (MH$^+$), found 640.3657.

EXAMPLE 20

Preparation of Compound 24 of Table I by the Method of Scheme 1

Similar reaction of 2-iodoisophthalic acid and 4-tert-butylaniline gave 2-[(4-tert-butyl)phenylamino]isophthalic acid (93%), mp (EtOAc/petroleum ether) 221–222° C. $^1$H NMR [(CD$_3$)$_2$SO] δ 1.24 (s, 9 H, 3×CH$_3$), 6.84 (d, J=8.7 Hz, 2 H, H-2' and H-6' or H-3' and H-5'), 6.99 (t, J=7.7 Hz, 1 H, H-5), 7.21 (d, J=8.6 Hz, 2 H, H-3' and H-5' or H-2' and H-6'), 7.93 (d, J=7.8 Hz, 2 H, H-4 and H-6), 9.65 (br s, 1 H, NH) and 12.99 (br s, 2 H, 2×COOH Anal. (C$_{18}$H$_{13}$NO$_2$) C, H, N.

Cyclization of this as above gave 7-tert-butyl-9-oxoacridan-4-carboxylic acid (79%), mp (H$_2$O/MeOH) 326–327.5° C. $^1$H NMR [(CD$_3$)$_2$SO] δ 1.37 (s, 9 H, 3×CH$_3$), 7.34 (t, J=7.8 Hz, 1 H, H-2), 7.74 (d, J=8.8 Hz, 1 H, H-5), 7.88 (dd, J=8.8, 2.3 Hz, 1 H, H-6), 8.19 (d, J=2.4 Hz, 1 H, H-8), 8.43 (dd, J=7.6, 1.6 Hz, 1 H, H-3), 8.53 (dd, J=8.0, 1.6 Hz, 1 H, H-1), 11.96 (s, 1 H, NH) and 13.85 (br s, 1 H, COOH) ) Anal. (C$_{18}$H$_{17}$NO$_3$) C, H. N.

Reduction of this as above gave 7-tert-butylacridine-4-carboxylic acid (62%), mp (acetone) 253–253.5° C. $^1$H NMR [(CD$_3$)$_2$SO] δ 1.46 (s, 9 H, 3×CH$_3$), 7.83 (dd, J=8.4, 7.1 Hz, 1 H, H-2), 8.18 (d, J=1.7 Hz, 1 H, H-8), 8.22 (dd, J=9.2, 2.0 Hz, 1 H, H-6), 8.27 (d, J=9.2 Hz, 1 H, H-5), 8.52 (dd, J=8.4, 1.2 Hz, 1 H, H-1), 8.72 (dd, J=7.1, 1.2 Hz, 1 H, H-3), 9.46 (s, 1 H, H-9) and 17.11 (br s, 1 H, COOH)). Anal. (C$_{18}$H$_{17}$NO$_2$) C, H, N.

Activation and coupling of this as above gave bis[(7-tert-butylacridine-4-carboxamido)-propyl]methylamine (24) (82%) as a yellow oil. $^1$H NMR (CDCl$_3$) δ 1.43 (s, 18 H, 6×CH$_3$), 2.04–2.07 (m, 4 H, 2×CH$_2$CH$_2$CH$_2$), 2.38 (s, 3 H, NCH$_3$), 2.72 (t, J=7.4 Hz, 4 H, 2×CH$_2$NCH$_3$), 3.74 (q, J=6.8, 5.6 Hz, 4 H, 2×CH$_2$NH), 7.59 (dd, J=8.3, 7.2 Hz, 2 H, H-2), 7.81 (d, J=2.1 Hz, 2 H, H-8), 7.88 (dd, J=9.2, 2.1 Hz, 2 H, H-6), 8.05 (dd, J=8.3, 1.4 Hz, 2 H, H-1), 8.07 (d, J=9.3 Hz, 2 H, H-S), 8.73 (s, 2 H, H-9), 8.89 (dd, J=7.2, 1.5 Hz, 2 H, H-3) and 11.87 (br t, J=5.1 Hz, 2 H, 2×(CONH)). HRMS (FAB$^+$) m/z calcd for C$_{43}$H$_{50}$N$_5$O$_2$ 668.3965 (MH$^+$), found 668.3963.

EXAMPLE 21

Preparation of Compound 25 of Table I by the Method of Scheme 1

Reduction of the known [Denny et al., *J. Med. Chem.*, 1987, 30, 658] 7-phenyl-9-oxoacridan-4-carboxylic acid as above gave 7-phenylacridine-4-carboxylic acid (69%), mp (acetone) 239–241° C. $^1$H NMR [(CD$_3$)$_2$SO] δ 7.49 (t, J=7.3 Hz, 1 H, H-4'), 7.60 (t, J=7.3 Hz, 2 H, H-3' and H-5'), 7.86 (dd, J=8.4, 7.1 Hz, 1 H, H-2), 7.96 (d, J=7.3 Hz, 2 H, H-2' and H-6'), 8.43 (br s, 2 H, H-6 and H-8), 8.58 (dd, J=8.5, 1.2 Hz, 1 H, H-1), 8.64 (br s, 1 H, H-5), 8.74 (br d, J=7.1 Hz, 1 H, H-3), 9.56 (s, 1 H, H-9), 16.93 (br s, 1 H, COOH). Anal. (C$_{20}$H$_{13}$NO$_2$) C, H, N.

Activation and coupling of this as above gave bis[(7-phenylacridine-4-carboxamido)-propyl]methylamine (25) (90%), mp (CH$_2$Cl$_2$/MeOH) 162–163° C. $^1$H NMR (CDCl$_3$) δ 2.07–2.14 (m, 4 H, 2×CH$_2$CH$_2$CH$_2$), 2.42 (s, 3 H, NCH$_3$), 2.82 (t, J=7.4 Hz, 4 H, 2×CH$_2$NCH$_3$), 3.77 (q, J=6.5, 5.6 Hz, 4 H, 2×CH$_2$NH), 7.40–7.52 (m, 4 H, H-2 and H-4' or H-3' and H-5'), 7.48–7.52 (m, 4 H, H-3' and H-5' or H-2 and H-4'), 7.63–7.65 (m, 4 H, H-2' and H-6'), 7.82–7.84 (m, 4 H, H-6 and H-8), 7.87 (dd, J=8.4 ,1.4 Hz, 2 H, H-1), 7.97 (d, J=9.5 Hz, 2 H, H-5), 8.54 (s, 2 H, H-9), 8.80 (dd, J=7.1, 1.5 Hz, 2 H, H-3), 11.69 (br t, J=5.2 Hz, 2 H, 2NH). HRMS (FAB$^+$) m/z calcd for C$_{47}$H$_{42}$N$_5$O$_2$ 708.3339 (MH$^+$), found 708.3351.

EXAMPLE 22

Preparation of Compound 26 of Table I by the Method of Scheme 1

Activation and coupling of the known [Atwell et al., *J. Med. Chem.* 1987, 30, 664] 7-methoxyacridine-4-carboxylic acid gave bis[(7-methoxyacridine-4-carboxamido)propyl]-methylamine (26) (93%) as a yellow oil. $^1$H NMR (CDCl$_3$) δ 2.02–2.06 (m, 4 H, 2×CH$_2$CH$_2$CH$_2$), 2.37 (s, 3 H, NCH$_3$), 2.74 (t, J=7.4 Hz, 4 H, 2×CH$_2$NCH$_3$), 3.72 (q, J=6.7, 5.6 Hz, 4 H, 2×CH$_2$NH), 3.88 (s, 6 H, OCH$_3$), 6.89 (d, J=2.7 Hz, 2 H, H-8), 7.32 (dd, J=9.3, 2.7 Hz, 2 H, H-6), 7.54 (dd, J=8.2, 7.2 Hz, 2 H, H-2), 7.85 (d, J=9.3 Hz, 2 H, H-5), 7.94 (dd, J=8.4, 1.5 Hz, 2 H, H-1), 8.44 (s, 2 H, H-9), 8.82 (dd, J=7.1, 1.5 Hz, 2 H, H-3), 11.69 (br t, J=5.1 Hz, 2×CONH). HRMS (FAB$^+$) m/z calcd for C$_{37}$H$_{38}$N$_5$O$_4$ 616.2924 (MH$^+$), found 616.2927.

EXAMPLE 23

Preparation of Compound 27 of Table I by the Method of Scheme 1

Reduction of the known [Atwell et al., *J. Med. Chem.*, 1987, 30, 658] 7-fluoro-9-oxoacridan-4-carboxylic acid as above gave 7-fluoroacridine-4-carboxylic acid (95%), mp (MeOH/H$_2$O) 267–268° C. $^1$H NMR [(CD$_3$)$_2$SO] δ 7.87 (dd, J=8.4, 7.0 Hz, 1 H, H-2), 8.01 (ddd, J=9.5, 8.5, 2.3 Hz, 1 H, H-6), 8.13 (dd, J=9.3, 2.8 Hz, 1 H, H-8), 8.45 (dd, J=9.6, 5.3 Hz, 1 H, H-5), 8.54 (dd, J=8.5, 1.3 Hz, 1 H, H-1), 8.73 (dd, J=6.9, 1.4 Hz, 1 H, H-3), 9.47 (s, 1 H, H-9), 16. 53 (br s, 1 H, COOH). Anal. (C$_{14}$H$_8$FNO$_2$) C, H, N, F.

Activation and coupling of this as above gave bis[(7-fluoroacridine-4-carboxamido)propyl]-methylamine (27) (57%), mp (HCl salt) 173.5° C. (dec). $^1$H NMR (CDCl$_3$) δ 2.04 (quin, J=7.07 Hz, 4 H, 2×CH$_2$CH$_2$CH$_2$), 2.73 (t, J=7.4 Hz, 4 H, 2×CH$_2$NCH$_3$), 3.73 (q, J=6.3 Hz, 4 H, 2×CH$_2$NH), 7.32 (dd, J=8.6, 2.7 Hz, 2 H, H-8), 7.42 (ddd, J=9.4, 8.1, 2.7 Hz, 4 H, H-6), 7.63 (dd, J=7.7, 7.2 Hz, 2 H, H-2), 7.96 (dd, J=9.1, 4.9 Hz, 2 H, H-5), 7.99 (dd, J=7.7, 1.5 Hz, 2 H, H-1), 8.56 (s, 2 H, H-9), 8.89 (dd, J=7.0, 1.5 Hz, 2 H, H-3), 11.50 (t, J=4.95 Hz, 2 H, 2×CONH).

EXAMPLE 24

Preparation of Compound 28 of Table I by the Method of Scheme 1

Activation and coupling of the known [Atwell et al., *J. Med. Chem.* 1987, 30, 664] 7-chloroacridine-4-carboxylic acid gave bis[(7-chloroacridine-4-carboxamido)propyl] methyl-amine (28) (75%) as a yellow oil. $^1$H NMR (CDCl$_3$) δ 2.03–2.07 (m, 4 H, 2×CH$_2$CH$_2$CH$_2$), 2.38 (s, 3 H, NCH$_3$), 2.75 (t, J=7.4 Hz, 4 H, 2×CH$_2$NCH$_3$), 3.73 (q, J=6.1, Hz, 4 H, 2×CH$_2$NH), 7.45 (dd, J=9.2, 2.3 Hz, 2 H, H-6), 7.63–7.67 (m, 4 H, H-2 and H-8), 7.84 (d, J=9.2 Hz, 2 H, H-5), 7.99 (dd, J=8.4, 1.5 Hz, 2 H, H-1), 8.48 (s, 2 H, H-9), 8.93 (dd, J=7.2, 1.5 Hz, 2 H, H-3), 11.42 (br t, J=5.0 Hz, 2×CONH). HRMS (FAB+) m/z calcd for (MH$^+$) C$_{35}$H$_{32}$$^{35}$Cl$_2$N$_5$O$_2$ 624.1933, found 624.1923.

EXAMPLE 25

Preparation of Compound 29 of Table I by the Method of Scheme 1

Reduction of 7-bromo-9-oxoacridan-4-carboxylic acid as above gave 7-bromoacridine-4-carboxylic acid (59%), mp (MeOH/H$_2$O) 304° C. (dec). $^1$H NMR [(CD$_3$)$_2$SO] δ 7.87 (dd, J=8.4, 7.2 Hz, 1 H, H-2), 8.13 (dd, J=9.2, 2.2 Hz, 1 H, H-6), 8.32 (d, J=9.2 Hz, 1 H, H-5), 8.56 (dd, J=8.5, 1.3 Hz, 1 H, H-1), 8.66 (d, J=2.1 Hz, 1 H, H-8), 8.74 (dd, J=7.1, 1.4 Hz, 1 H, H-3), 9.48 (s, 1 H, H-9), 16.49 (s, 1 H, COOH). Anal. (C$_{14}$H$_8$BrNO$_2$) C, H, N, Br.

Activation and coupling of this as above gave bis[(7-bromoacridine-4-carboxamido)propyl]-methylamine (29) (25%), mp (HCl salt) 138–142° C. $^1$H NMR (CDCl$_3$) δ 2.04 (quin, J=7.0 Hz, 4 H, 2×CH$_2$CH$_2$CH$_2$), 2.38 (s, 3 H, CH$_3$), 2.75 (t, J=7.4 Hz, 4 H, 2×CH$_2$NCH$_3$), 3.73 (q, J=6.3 Hz, 4 H, 2×CH$_2$NH), 7.55 (dd, J=9.1, 2.1 Hz, 2 H, H-6), 7.66 (dd, J=8.3, 7.2 Hz, 2 H, H-2), 7.76 (d, J=9.2 Hz, 2 H, H-5), 7.83 (d, J=2.1 Hz, 2 H, H-8), 7.99 (dd, J=8.2, 1.4 Hz, 2 H, H-1), 8.46 (s, 2 H, H-9), 8.94 (dd, 7.0, 1.5 Hz, 2 H, H-3), 11.41 (t, J=4.9 Hz, 2 H, 2×CONH).

EXAMPLE 26

Preparation of Compound 30 of Table I by the Method of Scheme 1

Activation and coupling of the known [Atwell et al., J. Med. Chem. 1987, 30, 664] 8-methyl-9-oxoacridan-4-carboxylic acid as above gave bis[(8-methylacridine-4-carboxamido)propyl]methylamine (30) as a yellow oil (61%). $^1$H NMR (CDCl$_3$) δ 2.03–2.10 (m, 4 H, 2×CH$_2$CH$_2$CH$_2$), 2.39 (s, 3 H, NCH$_3$), 2.66 (s, 6 H, 2×CH$_3$), 2.79 (t, J=7.5 Hz, 4 H, 2×CH$_2$NCH$_3$), 3.74 (q, J=6.2 Hz, 4 H, 2×CH$_2$NH), 7.09 (d, J=6.9 Hz, 2 H, H-5 or H-7), 7.49 (dd, J=8.8, 6.8 Hz, 2 H, H-6), 7.62 (dd, J=8.4, 7.1 Hz, 2 H, H-2), 7.83 (d, J=8.7 Hz, 2 H, H-7 or H-5), 8.04 (dd, J=8.3, 1.5 Hz, 2 H, H-1), 8.74 (s, 2 H, H-9), 8.91 (dd, J=7.1, 1.5 Hz, 2 H, H-3) and 11.78 (br t, J=4.8 Hz, 2×CONH); HRMS (FAB$^+$) m/z calcd. for C$_{37}$H$_{38}$N$_5$O$_2$ 584.3026 (MH$^+$), found 584.3033. Anal. (C37H37N5O2.0.5H$_2$O) C,H,N.

EXAMPLE 27

Preparation of Compound 31 of Table 1 by the Method of Scheme 1

Activation and coupling of the know chloroacridine-4-carboxylic acid gave bis[(8-chloroacridine-4-carboxamido) propyl]methylamine (31) as a yellow oil (88%). $^1$H NMR (CDCl$_3$) δ 2.04–2.10 (m, 4 H, 2×CH$_2$CH$_2$CH$_2$), 2.40 (s, 3 H, NCH$_3$), 2.84 (t, J=7.4 Hz, 4 H, 2×CHNCH$_3$), 3.74 (q, J=6.1, Hz, 4 H, 2CH$_2$NH), 7.10 (dd, J=7.3, 0.8 Hz, 2 H, H-5 or H-7), 7.33 (dd, J=8.8, 7.3 Hz, 2 H, H-2 or H-6), 7.65 (dd, J=8.3, 7.2 Hz, 2H, H-6 or H-2), 7.73 (d, J=8.7 Hz, 2H, H-7 or H-5), 8.06 (dd, J=8.8, 1.5 Hz, 2 H, H-1), 8.86 (s, 2H, H-9), 8.90 (dd, J=7.2, 1.5 Hz, 2H, H-3) and 11.36 (br t, J=5.0 Hz, 2 H, 2×CONH); HRMS (FAB+) m/z calcd. for C$_{35}$H$_{32}$$^{35}$Cl$_2$N$_5$O$_2$ 624.1933 (MH$^+$), found 624.1939. Anal. (C$_{35}$H$_{31}$Cl$_2$N$_5$O$_2$) C, H, N.

EXAMPLE 28

Preparation of Compound 37 of Table 1 by the Method of Scheme 1

Activation and coupling of acridine-2-carboxylic acid gave bis[(acridine-2-carboxamido)propyl]methyl-amine (37) (60%), mp (CH$_2$Cl$_2$/petroleum ether) 199–200° C. $^1$H NMR (CDCl$_3$) δ 1.85–1.91 (m, 4 H, 2×CH$_2$CH$_2$CH$_2$), 2.36 (s, 3 H, NCH$_3$), 2.59 (t, J=6.2 Hz, 4 H, 2×CH$_2$NCH$_3$), 3.65 (dd, J=6.3, 5.9 Hz, 4 H, 2×CH$_2$NH), 7.41 (ddd, J=8.4, 6.6, 1.0 Hz, 2 H, H-6 or H-7), 7.64 (br t, J=5.3 Hz, 2 H, 2×NH), 7.70 (ddd, J=8.9, 6.6, 1.4 Hz, 2H, H-7 or H-6), 7.75 (d, J=8.1 Hz, 2 H, H-5 or H-8), 8.06 (dd, J=9.1, 1.9 Hz, 2 H, H-3), 8.13 (dd, J=8.9, 0.8 Hz, 2 H, H-8 or H-5), 8.20 (d, J=9.1 Hz, 2 H, H-4), 8.36 (d, J=1.9 Hz, 2 H, H-1) and 8.52 (s, 2 H, H-9). HRMS (FAB+) m/z calcd. for C$_{35}$H$_{34}$N$_5$O$_2$ 556.2713 (MH$^+$), found 556.2694. Anal. C$_{35}$H$_{33}$N$_5$O$_2$) C, H, N.

EXAMPLE 29

Preparation of Compound 33 of Table 1 by the Method of Scheme 2

A solution of methyl 2-[N-(2-carboxyphenyl)amino] benzoate [Rewcastle and Denny, Synth. Comm., 1987, 17, 309] (10 g, 36.9 mmol) in dry THF (200 mL) was treated with CDI (8.97 g, 55.4 mmol). The reaction mixture was allowed to stir at room temperature for 1 h, then added slowly to a suspension of NaBH$_4$ (7.00 g) in H$_2$O (200 mL) without isolation of the intermediate imidazolide. When the reaction was observed to be complete (tlc; ca. 30 min), the mixture was quenched with conc. HCl and partitioned between CH$_2$Cl$_2$ (200 mL) and NaHCO$_3$ (200 mL), and the organic layer was dried with Na$_2$SO$_4$. Removal of the solvent and filtration of the residue through a plug of flash-grade silica gel in petroleum ether/EtOAc (4:1) gave methyl 2-[N-(2-hydroxymethyl)phenylamino]benzoate, (7.85 g, 83%), mp (CH$_2$Cl$_2$/petroleum ether) 69.0–71.0° C. $^1$H NMR (CDCl$_3$) δ 1.93 (br s, 1 H, OH), 3.91 (s, 3 H, COOCH$_3$), 4.72 (s, 2 H, CH$_2$OH), 6.74 (ddd, J=8.0, 7.0, 1.1 Hz, 1 H, H-5), 7.08–7.44 (m, 6 H, H-3,3',4,4',5',6'), 7.97 (dd, J=8.0, 1.6 Hz, 1 H, H-6), 9.59 (br s, 1 H, NH). Anal. (C$_{15}$H$_{14}$NO$_3$) C, H, N.

A stirred solution of the above alcohol (7.74 g, 30 mmol) in acetone (200 mL) was treated with a suspension of MnO$_2$ (10 g) at room temperature for 3 days, when all the starting material had been consumed (tlc). The MnO$_2$ was filtered off (Celite) and the acetone removed under reduced pressure to yield methyl 2-[N-(2-formyl)phenylamino]benzoate as a bright yellow solid (7.70 g, 100%). A sample crystallized from (EtOAc/petroleum ether had mp 110.0–112.0° C. $^1$H NMR (CDCl$_3$) δ 3.95 (s, 3 H, COOCH$_3$), 6.95–7.03 (m, 2 H, H-4',5), 7.41–7.45 (m, 2 H, H-5',6), 7.50 (br d, J=8.5 Hz, 1 H, H-3 or H-6'), 7.61 (br d, J=8.2 Hz, 1 H, H-6' or H-3), 7.65 (dd, J=7.7, 1. 7 Hz, 1 H, H-3'), 8.01 (dd, J=7.9, 1.7 Hz, 1 H, H-6), 10.00 (s, 1 H, CHO), 11.26 (br s, 1 H, NH). Anal. (C$_{15}$H$_{13}$NO$_3$) C, H, N.

The above aldehyde (210 mg, 0.8 mmol) was placed in a two-necked flask which was then flushed with N$_2$, trifluoroacetic acid (10 mL) was added, and the solution was stirred for 15 hours at room temperature under N$_2$. The trifluoroacetic acid was then removed under reduced pressure, and the flask containing the resultant crude methyl acridine-4-carboxylate was flushed with nitrogen. A degassed 2 M solution of NaOH in aqueous EtOH (1:1) (35 mL) was then added, and the mixture was stirred for 3 h at 50° C. under $N_2$ until a clear solution was obtained, then neutralized with glacial AcOH and extracted with EtOAc (3×50 mL). Evaporation of the organic layer and chromatography of the residue on silica gel, eluting with EtOAc/petroleum ether (1:4) gave acridine-4-carboxylic acid (160 mg, 87%) mp ($Me_2CO$) 196–197° C. [Atwell et al., J. Med. Chem. 1987, 30, 664 record mp 202–204° C.

Dilution of the residue at this point with $CH_2Cl_2$ and careful neutralization of the solution with $Et_3N$, followed by removal of solvent under reduced pressure and filtration of the residue was through a short column of flash silica gel in EtOAc/petroleum ether (1.3) gave pure methyl acridine-4-carboxylate as an orange oil. $^1H$ NMR ($CDCl_3$) δ 4.12 (s, 3 H, $COOCH_3$), 7.53–7.58 (m, 2 H, H-2 and H-6 or H-7), 7.79 (ddd, J=8.8, 6.6, 1.4 Hz, 1 H, H-7 or H-6), 8.00 (dd, J=8.0, 1.0 Hz, 1 H, H-1), 8.12–8.14 (m, 2 H, H-5,8), 8.30 (dd, J=8.7, 0.9 Hz, 1 H, H-3), 8.80 (s, 1 H, H-9).

A suspension of acridine-4-carboxylic acid (4.00 g, 17.9 mmol) in DMF (25 mL) was treated with CDI (3.49 g, 21.5 mmol) and stirred at 30° C. for 2 h. After cooling, the mixture was diluted with $CH_2Cl_2$ (25 mL) followed by petroleum ether (75 mL) to complete precipitation of product, which was collected, washed with petroleum ether/$CH_2Cl_2$ (4:1) and dried to give the moisture sensitive imidazolide (3.81 g, 78%). This was reacted with N,N-bis(3-aminopropyl)methylamine following the procedure described above. The product was purified by chromatography on alumina-90, eluting with $CH_2Cl_2$/MeOH (20:1) to give bis[(acridine-4-carboxamido)propyl]methylamine (33) 83%) as a foam. $^1H$ NMR [$(CD_3)_2SO$] δ 9.06 (s, 2 H, H-9), 8.65 (d, J=7.1 Hz, 2 H, H-3), 8.24 (d, J=8.5 Hz, 2 H, ArH), 8.00 (t, J=9.5 Hz, 4 H, ArH), 7.8–7.6 (m, 4 H, ArH), 7.45 (t, J=7.5 Hz, 2 H, ArH), 3.58 (q, J=6.2 Hz, 4 H, 2×$NHCH_2$), 2.65 (t, J=7.0 Hz, 4 H, 2×$CH_2NCH_3$), 2.29 (s, 3 H, $CH_3$), 1.91 (quint, J=6.9 Hz, 4 H, 2×$CH_2CH_2CH_2$). Crystallization from MeOH/EtOAc/HCl gave the trihydrochloride salt, mp 168–170° C. Anal. ($C_{35}H_{33}N_5O_2$.3HCl) C,H,N,Cl.

EXAMPLE 30

Preparation of Compound 34 of Table 1 by the Method of Scheme 2

Reaction of acridine-4-carboxylic acid imidazolide with N,N-bis(2-aminoethyl)amine as above, followed by crystallization of the crude product from MeOH/$H_2O$, gave bis[2-(acridine-4-carboxamido)ethyl]amine (34) (84%). $^1H$ NMR [$(CD_3)_2SO$] δ 11.57 (t, J=5.0 Hz, 2 H, 2×CONH), 8.80 (s, 2 H, H-9), 8.46 (d, J=7.1 Hz, 2 H, H-3), 8.08 (d, J=8.4 Hz, 2 H, ArH), 7.92 (d, J=8.7 Hz, 2 H, ArH), 7.79 (d, J=8.1 Hz, 2 H, ArH), 7.55 (t, J=7.7 Hz, 2 H, ArH), 7.41 (t, J=7.6 Hz, 2 H, ArH), 7.27 (t, J=7.4 Hz, 2 H, ArH), 3.73 (q, J=5.5 Hz, 4 H, 2×$NHCH_2$), 3.11 (t, J=5.6 Hz, 4 H, $CH_2NHCH_2$). The trihydrochloride salt crystallized from MeOH/EtOAc/HCl, mp 182–184° C. Anal. ($C_{32}H_{27}N_5O_2$.3HCl) C, H, N, Cl.

EXAMPLE 31

Preparation of Compound 35 of Table 1 by the Method of Scheme 2

Similar reaction of acridine-4-carboxylic acid imidazolide with N,N-bis(3-aminopropyl)amine as above, followed by purification of the product by chromatography on alumina-90, eluting with $CH_2Cl_2$/MeOH (20:1), gave bis[3-(acridine-4-carboxamido)propyl]amine (35) (80%) as an oil. $^1H$ NMR [$(CD_3)_2SO$] δ 11.40 (t, J=5.4 Hz, 2 H, 2×CONH), 9.19 (s, 2 H, H-9), 8.71 (d, J=7.1 Hz, 2 H, H-3), 8.32 (d, J=8.5 Hz, 2 H, ArH), 8.18–8.00 (m, 4 H, ArH), 7.83–7.62 (m, 4 H, ArH), 7.51 (t, J=7.5 Hz, 2H, ArH), 3.64 (q, J=6.0 Hz, 4H, 2×$CONHCH_2$) 2.86 (t, J=6.7 Hz, 4H, $CH_2NHCH_2$) 1.92 (quint, J=6.5 Hz, 4 H, 2×$CH_2CH_2CH_2$). Crystallization from MeOH/EtOAc/HCl gave the trihydrochloride salt, mp 171–173° C. Anal. ($C_{34}H_{31}N_5O_2$.2HCl.2$H_2O$) C, H, N, Cl.

EXAMPLE 32

Preparation of Compound 36 of Table 1 by the Method of Scheme 2

Similar reaction of acridine-4-carboxylic acid imidazolide with 1,4-bis(3-aminopropyl)piperazine as above, and crystallization of the crude product from $CH_2Cl_2$/EtOAc/$iPr_2O$, gave $N^1$,N4-bis[(acridine-4-carboxamido)propyl]piperazine (36) (91%). $^1H$ NMR [$(CD_3)_2SO$] δ 11.39 (t, J=5.2 Hz, 2 H, 2×CONH), 9.33 (s, 2 H, H-9), 8.73 (d, J=7.0 Hz, 2 H, H-3), 8.38 (d, J=8.5 Hz, 2 H, ArH), 8.32–8.20 (m, 4 H, ArH), 7.97 (t, J=7.8 Hz, 2 H, ArH), 7.82–7.63 (m, 4 H, ArH), 3.57 (q, J=6.0 Hz, 4 H, 2×$NHCH_2$), 2.6–2.3 t (m, 12 H, H-piperazine, 2×$CH_2CH_2CH_2N$), 1.85 (quint, J=6.7 Hz, 4 H, $CH_2CH_2CH_2$). Crystallization from MeOH/EtOAc/HCl gave the tetrahydrochloride salt, mp 248–253° C. Anal. ($C_{38}H_{38}N_6O_2$.4HCl) C, H, N, Cl.

EXAMPLE 33

Preparation of Compound 18 of Table 1 by the Method of Scheme 2

Reaction of methyl 2-iodobenzoate and 4-bromoanthranilic acid by the reported method [Rewcastle and Denny, Synth. Comm, 1987, 17, 309] gave 4-bromo-2-[(2-methoxycarbonyl-phenyl)amino]benzoic acid (70%), mp (MeOH/$H_2O$) 218–219.5° C. $^1H$ NMR [$(CD_3)_2SO$] δ 3.85 (s, 3 H, $COOCH_3$), 7.08–7.12 (m, 2 H, 2×ArH), 7.50 (d, J=1.9 Hz, 1 H, H-3), 7.57 (d, J=3.8 Hz, 3 H, 2×ArH), 7.84 (d, J=8.4 Hz, 1 H, ArH), 7.93 (d, J=7.7 Hz, 1 H, ArH), 10.80 (s, 1 H, NH), 13.33 (br s, 1 H, COOH). Anal. ($C_{15}H_{12}BrNO_4$) C, H, N.

Formation of the imidazolide and reduction of this as above gave crude methyl-2-[N-(5-bromo-2'-hydroxymethyl)phenylamino]benzoate (81%). $^1H$ NMR [$(CD_3)_2SO$] δ 3.91 (s, 3 H, $COOCH_3$), 4.68 (d, J=4.8 Hz, 2 H, $CH_2$), 6.79–6.84 (m, 1 H, ArH), 7.17–7.21 (m, 2 H, 2×ArH), 7.25 (d, J=8.5 Hz, 1 H, ArH), 7.40–7.43 (m, 2 H, ArH), 7.55 (d, J=1.8 Hz, 1 H, H-6'), 9.66 (s, 1 H, NH). Oxidation of this as above gave methyl 2-[N-(5'-bromo-2'-formyl)phenylamino]-benzoate (67% over two steps), mp (MeOH/$H_2O$) −122–123° C. $^1H$ NMR [$(CD_3)_2SO$] δ 3.95 (s, 3 H, $CO_2CH_3$), 7.05–7.11 (m, 2 H, ArH), 7.41–7.52 (m, 2 H, 2×ArH), 7.58–7.62 (m, 2 H, 2×ArH), 8.03 (dd, J=7.9, 1.6 Hz, 1 H, ArH), 9.93 (s, 1 H, CH), 11.33 (br s, 1 H, NH). Anal. ($C_{15}H_{12}BrNO_3$) C, H, N.

Cyclization of this as above gave crude methyl 6-bromoacridine-4-carboxylate, which was immediately hydrolyzed as above to give 6-bromoacridine-4-carboxylic acid (100% over two steps), mp (MeOH/$H_2O$) 283–285° C. $^1H$ NMR [$(CD_3)_2SO$] δ 7.87 (dd, J=8.3, 7.15 Hz, 1 H, H-2), 7.99 (dd, J=9.0, 1.9 Hz, 1 H, H-7), 8.23 (d, J=9.1 Hz, 1 H, H-8), 8.56 (dd, J=8.4, 1.4 Hz, 1 H, H-1), 8.70 (s, 1 H, H-5), 8.73 (dd, J=7.06, 1.4 Hz, H-4), 9.57 (s, 1 H, H-9), 16.44 (br s, 1 H, COOH). Anal. ($C_{14}H_8BrNO_2$) C, H, N.

Activation and coupling of this as above gave bis[(6-bromoacridine-4-carboxamido)propyl]-methylamine (18)

(91%), mp (HCl salt) 218–221° C. $^1$H NMR (CDCl$_3$) δ 2.07(quin, J=7.0 Hz, 4 H, 2×CH$_2$CH$_2$CH$_2$), 2.41 (s, 3 H, CH$_3$), 2.76 (t, J=7.4 Hz, 4 H, 2×CH$_2$NCH$_3$), 3.75 (q, J=6.4 Hz, 4 H, 2×CH$_2$NH), 7.42 (dd, J=8.95, 1.8 Hz, 2 H, ArH), 7.65 (m, 4 H, ArH), 8.03 (dd, J=8.4, 1.5 Hz, 2 H, ArH), 8.25 (d, J=0.9 Hz, H-5), 8.67 (s, 2 H, H-9), 8.95 (dd, J=7.15, 1.5 Hz, 2 H, ArH), 11.45 (t, J=5.0 Hz, 2 H, CONH).

EXAMPLE 34

Preparation of Compound 14 of Table 1 by the Method of Scheme 2

Similar reaction of 2-amino-3-trifluoromethylbenzoic acid and methyl-2-iodobenzoate by the reported method [Rewcastle and Denny, *Synth. Comm*, 1987, 17, 309] gave 3-trifluoromethyl-2-[(2-methoxycarbonyl)phenyl)amino]benzoic acid (51%), mp (MeOH/H$_2$O) 113–115° C. $^1$H NMR [(CD$_3$)$_2$SO] δ 3.89 (s, 3 H, CO$_2$CH$_3$), 6.35 (d, J=8.5 Hz, 1 H, ArH), 6.78 (t, J=7.5 Hz, 1 H, ArH), 7.30 (ddd, J=7.8, 7.8, 1.6 Hz, 1 H, ArH), 7.59 (t, J=7.8 Hz, 1 H, ArH), 7.88 (dd, J=8.0, 1.5 Hz, 1 H, ArH), 8.03 (d, J=7.4 Hz, 1 H, ArH), 8.07 (d, J=8.07 Hz, 1 H, ArH), 9.49 (s, 1 H, NH), 13.15 (br s, 1 H, COOH). Anal. (C$_{16}$H$_{12}$F$_3$NO$_2$) C, H, N, F.

Formation of the corresponding imidazolide and immediate reduction of this as above gave crude methyl-2-[N-(2-hydroxymethyl-6-trifluoromethyl)phenylamino]benzoate (100%) as an oil. $^1$H NMR [(CD$_3$)$_2$SO] δ 3.94 (s, 3 H, CO$_2$CH$_3$), 4.50 (d, J=14.0 Hz, 1 H, CH), 4.72 (d, J=14.0 Hz, 1 H. CH), 6.18 (dd, J=8.6, 0.7 Hz, 1 H, ArH), 6.72 (ddd, J=7.7, 7.5, 1.0 Hz, 1 H, ArH), 7.23 (ddd, J=8.5, 7.1, 1.5 Hz, 1 H, ArH), 7.46 (t, J=7.8 Hz, 1 H, ArH), 7.70 (d, J=7.1 Hz, 1 H, ArH), 7.83 (d, J=7.7 Hz, 1 H, ArH), 7.98 (dd, J=8.0, 1.6 Hz , 1 H, ArH), 9.25 (s, 1 H, NH).

A solution of the above crude ester was oxidized as above to give methyl 2-[N-(6-trifluoromethyl-2-formyl)phenylamino]benzoate (100%), mp (MeOH/H$_2$O) 122–123° C. $^1$H NMR (CDCl$_3$) δ 3.96 (s, 3 H, CO$_2$CH$_3$), 6.49 (dd, J=8.3, 0.8 Hz, 1 H, ArH), 6.79 (td, J=7.5, 1.0 Hz, 1 H, ArH), 7.25 (ddd, J=8.3, 6.5, 1,6 Hz, 1 H, ArH), 7.50 (t, J=7.8 Hz, 1 H, ArH), 7.9–8.01 (m, 2 H, 2×ArH), 8.14 (dd, J=7.8, 1.4 Hz, 1 H, ArH), 9.71 (br s, 1 H, CHO), 10.09 (s, 1 H, NH). Anal. (C$_{16}$H$_{12}$F$_3$NO$_3$) C, H. N).

Cyclization of this, followed by hydrolysis as above, gave 5-trifluoromethylacridine-4-carboxylic acid (76%), mp (MeOH/H$_2$O) 287–288.5° C. $^1$H NMR δ 7.89–7.98 (m, 2 H, 2×ArH), 8.55 (d, J=7.0 Hz, 1 H, ArH), 8.65 (td, J=8.7, 1.3 Hz, 2 H, 2×ArH), 8.86 (dd, J=6.9, 1.4 Hz, 1 H, ArH), 9.74 (s, 1 H, H-9), 16.13 (br s, 1 H, COOH). Anal. (C$_{18}$H$_8$F$_3$NO$_4$) C, H, N.

Activation and coupling of this as above gave bis[(5-trifluoromethylacridine-4-carboxamido)propyl]methylamine (14) (52%), mp (EtOAc/MeOH) 231–233° C. $^1$H NMR [(CD$_3$)$_2$SO] δ 1.81 (quin, J=7.1 Hz, 4 H, CH$_2$CH$_2$CH$_2$), 2.42 (s, 3 H, NCH$_3$), 2.44 (t, J=7.1 Hz, 4 H, CH$_2$NH$_3$), 3.51 (q , J=6.8 Hz, 4 H, NHCH$_2$CH$_2$), 7.73 (q, J=7.4 Hz, 4 H,4×ArH), 8.24–8.29 (m, 4 H, 4×ArH), 8.42 (d, J=8.1 Hz, 2 H, ArH), 8.78 (dd, J=7.1, 1.5 Hz, 2 H, ArH), 9.30 (s, 2 H, H-9), 10.97 (t, J=5.8 Hz, 2 H, CONH). Anal. (C$_{37}$H$_{31}$F$_6$N$_5$O$_2$.3HCl.2H$_2$O) C, H, N).

EXAMPLE 35

Preparation of Compound 19 of Table 1 by the Method of Scheme 2

Reaction of 4-trifluoromethylanthranilic acid and methyl 2-iodobenzoate by the reported method [Rewcastle and Denny, *Synth, Comm* 1987, 17, 309 gave 4-trifluoromethyl-2-(2-methoxycarbonylphenyamino)benzoic acid (43%), mp (MeOH/H$_2$O) 206–207° C. $^1$H NMR [(CD$_3$)$_2$SO] δ 3.87 (s, 3 H, CO$_2$CH$_3$), 7.12 (ddd, J=8.0, 6.1, 2.1 Hz, 1 H., H-5'), 7.23 (dd, J=8.3, 1.0 Hz, 1 H, ArH), 7.55–7.62 (m, 3 H, 3×ArH), 7.95 (dd, J=8.0, 1.3 Hz, 1 H, ArH), 8.12 (d, J=8.2 Hz, 1 H, ArH). Formation of the corresponding imidazolide and immediate reduction of this as above gave methyl-2-[N-(5'-trifluoromethyl-2'-hydroxymethyl)phenyl-amino]benzoate (86%), mp (hexane) 86–87° C. $^1$H NMR (CDCl$_3$) δ 2.00 (t, J=5.6 Hz, 1 H, OH), 3.92 (s, 3 H, CO$_2$CH$_3$), 4.78(d, J=5.3 Hz, 2 H, CH$_2$), 6.84 (td, J=7.6, 1.1 Hz, 1 H, ArH), 7.15 (dd, J=8.6, 0.8 Hz, 1 H, ArH), 7.31–7.39 (m, 2 H, 2×ArH), 7.52 (d, J=7.7 Hz, 1 H, ArH), 7.70 (s, 1 H, H-6'), 8.76 (dd, J=8.0, 1.6 Hz, 1 H, ArH), 9.72 (s, 1 H, NH).

Oxidation of this as above gave methyl-2-[N-(5'-trifluoromethyl-2'-formyl)phenylamino]-benzoate (85%), mp (MeOH/H$_2$O) 79.5–80.5° C. $^1$H NMR [(CD$_3$)$_2$SO] δ 3.86 (s, 3 H, CO$_2$CH$_3$), 7.20 (ddd, J=8.0, 6.2, 2.0 Hz, 1 H, ArH), 7.34 (dd, J=7.5, 0.8 Hz, 1 H, ArH), 7.60–7.66 (m, 3 H, 3×ArH), 7.98 (dd, J=8.0, 1.4 Hz, 1 H, ArH), 8.09 (d, J=8.0 Hz, 1 H, ArH), 10.09 (s, 1 H, NH), 11.16 (s, 1 H, CHO).

Cyclization of this as above, followed by immediate hydrolysis of the crude methyl 6-trifluoromethylacridine-4-carboxylate, gave 6-trifluoromethylacridine-4-carboxylic acid (81%), mp (MeOH/H$_2$O) 244–246° C. $^1$H NMR [(CD$_3$)$_2$SO] δ 7.93 (t, J=7.9 Hz, 1 H, H-3), 7.98 (dd, J=8.9, 1.5 Hz, 1 H, ArH), 8.56 (d, J=8.8 Hz, 1 H, ArH), 8.60 (d, J=8.5 Hz, 1 H, ArH), 8.79 (dd, J=7.0, 1.1 Hz, 1 H, ArH), 8.86 (s, 1 H, H-5), 9.66 (s, 1 H, H-9).

Activation and coupling of this as above gave bis[(6-trifluoromethylacridine-4-carboxamido)propyl]-methylamine (19) (60%), mp (hexane) 169–171° C. $^1$H NMR [(CD$_3$)$_2$SO] δ 1.89 (quin, J=6.6 Hz, 4 H, CH$_2$CH$_2$CH$_2$), 2.28 (s, 3 H, NCH$_3$), 2.66 (t, J=6.8 Hz, 4 H, CH$_2$CH$_3$), 3.56 (q , J=6.1 Hz, 4 H. NHCH$_2$CH$_2$), 7.60 (dd, J=8.8, 1.5 Hz, 2 H, H-7), 7.68 (dd, J=8.3, 7.2 Hz, 2 H, H-2), 8.14 (d, J=8.8 Hz, 2 H, H-8), 8.23 (dd, J=8.4, 1.4 Hz, 2 H. ArH), 8.38 (s, 2 H, H-5), 8.55 (dd, J=7.2, 1.5 Hz, 2 H, ArH), 9.13 (s, 2 H, H-9), 10.78 (t, J=5.5 Hz, 2 H, CONH). Anal. (C$_{37}$H$_{31}$F$_6$N$_5$O$_2$.0.5H$_2$O) C, H, N.

EXAMPLE 36

Preparation of Compound 32 of Table 1 by the Method of Scheme 2

Reaction of 2-amino-3,5-dimethylbenzoic acid and methyl iodobenzoate as reported (Rewcastle and Denny, *Synth. Comm.*, 1987, 17, 309), and purification of the product on silica gel, eluting with EtOAc/petroleum ether (1:4), gave 3,5-dimethyl-2-[(2-methoxycarbonyl)phenylamino-benzoic acid, (73%), mp (EtOAc/petroleum ether) 210–211.5° C. $^1$H NMR (CDCl$_3$) δ 2.07 (s, 3 H, CH$_3$), 2.40 (s, 3 H, CH$_3$), 3.97 (s, 3 H, COOCH$_3$) 6.40 (dd, J=8.3, 0.9 Hz, 1 H, H-6'), 6.90–6.94 (m, 1 H, H-4'), 7.28–7.32 (m, 2 H, H-5' and H-4 or H-6), 8.00 (d, J=1.8 Hz, 1 H, H-6 or H-4), 8.03 (dd, J=8.0, 1.6 Hz, 1 H, H-3'), 9.45 (br s, 1 H, NH).

Reduction of this as above via the imidazolide gave methyl 2-[N-(4,6-dimethyl-2-hydroxymethyl)phenylamino]benzoate (86%), mp (EtOAc/petroleum ether) 105–106° C. $^1$H NMR (CDCl$_3$) δ 1.83 (br s, 1 H, OH), 2.13 (s, 3 H, CH$_3$), 2.36 (s, 3 H, CH$_3$), 3.92 (s, 3 H, COOCH$_3$), 4.51 (d, J=12.8 Hz, 1 H, CH$_2$OH), 4.63 (d, J=12.8 Hz, 1 H, CH$_2$OH), 6.22 (d, J=8.3 Hz, 1 H, H-3), 6.65 (br t, J=7.6 Hz, 1 H, H-5), 7.07

(br s, 1 H, H-3' or H-5'), 7.16 (br s, 1 H, H-5' or H-3'), 7.16–7.22 (m, 1 H, H-4), 7.95 (dd, J=8.0, 1.4 Hz, 1 H, H-6), 9.01 (br s, 1 H, NH).

Oxidation of this as above gave methyl 2-[N-(4,6-dimethyl-2-formyl)phenylamino]benzoate, (95%), mp (EtOAc/petroleum ether) 103–104° C. $^1$H NMR (CDCl$_3$) δ 2.19 (s, 3 H, CH$_3$), 2.40 (s, 3 H, CH$_3$), 3.95 (s, 3 H, COOCH$_3$), 6.31 (dd, J=8.3, 0.8 Hz, 1 H, H-3), 6.69–6.73 (m, 1 H, H-5), 7.20–7.24 (m, 1 H, H-4), 7.37 (d, J=1.6 Hz, 1 H, H-3' or H-5'), 7.60 (d, J=1.7 Hz, 1 H, H-5' or H-3'), 7.97 (dd, J=8.0, 1.6 Hz, 1 H, H-6), 9.42 (br s, 1 H, NH), 10.14 (s, 1 H, CHO).

Cyclisation of this as above gave crude methyl 5,7-dimethylacridine-4-carboxylate (99%). $^1$H NMR (CDCl$_3$) δ 2.53 (s, 3 H, CH$_3$), 2.88 (s, 3 H, CH$_3$), 4.12 (s, 3 H, COOCH$_3$), 7.49 (br s, 1 H, H-6 or H-8), 7.52 (dd, J=8.5, 7.0 Hz, 1 H, H-2), 7.57 (br s, 1 H, H-8 or H-6), 8.03 (dd, J=6.8, 1.4 Hz, 1 H, H-1 or H-3), 8.05 (dd, J=8.5, 1.4 Hz, 1 H, H-3 or H-1), 8.61 (s, 1 H, H-9). Hydrolysis of this as above gave 5,7-dimethylacridine-4-carboxylic acid (73%), mp (MeOH/TEA/AcOH) 312–315° C. $^1$H NMR [(CD$_3$)$_2$SO/NaOD] d 2.49 [s, partially obscured by DMSO, 3 H, CH$_3$), 7.39–7.45 (m, 2 H, H-1 and H-2), 7.49 (br s, 1 H, H-6 or H-8), 7.67 (br s, 1H, H-8 or H-6), 7.85 (dd, J=7.7, 2.1 Hz, 1 H, H-3) and 8.76 (s, 1 H, H-9). Anal. (C$_{16}$H$_{13}$NO$_2$) C, H, N.

Activation and coupling of this as above gave bis[(5,7-dimethylacridine-4-carboxamido)-propyl]methylamine (32) as an orange oil (56%). $^1$H NMR (CDCl$_3$) δ 1.94–2.05 (m, 4 H, 2×CH$_2$CH$_2$CH$_2$), 2.31 (s, 3 H, NCH$_3$), 2.45 (s, 6 H, 2×CH$_3$), 2.58 (t, J=7.4 Hz, 4 H, 2×CH$_2$NCH$_3$), 2.70 (s, 6 H, 2×CH$_3$), 3.68 (dd, J=7.2, 5.7 Hz, 4 H, 2×CHNH), 7.32 (br s, 2 H, H-6 or H-8) 7.41 (br s, 2 H, H-8 or H-6), 7.57 (dd, J=8.3, 7.2 Hz, 2 H, H-2), 7.96 (dd, J=8.4, 1.4 Hz, 2 H, H-1), 8.49 (s, 2 H, H-9), 8.89 (dd, J=7.2, 1.5 Hz, 2 H, H-3) and 11.75 (br t, J=5.3 Hz, 2 H, 2×CONH). HRMS (FAB$^+$) m/z calcd. for C$_{39}$H$_{42}$N$_5$O$_2$ 612.3339 (MH$^+$), found 612.3330. Anal. (C$_{39}$H$_{41}$N$_5$O$_2$.0.5H$_2$O) C,H,N.

EXAMPLE 37

Preparation of Compound 20 of Table 1

The bis(6-fluoro)trihydrochloride (16) (0.52 g, 0.7 mmol) was heated with 40 aqueous dimethylamine (10 mL) in MeOH (10 mL) in a bomb at 100° C. for one week. Solvent and excess reagent was evaporated under reduced pressure, ammonia was added, and the mixture was extracted with CH$_2$Cl$_2$. Evaporation and chromatography of the residue on alumina, eluting with a gradient of MeOH in CH$_2$Cl$_2$, gave bis[(6-(dimethylamino)acridine-4-carboxamido)propyl] methylamine (20) (84%), mp (HCl salt from MeOH/EtOAc) 100° C. (dec). $^1$H NMR (free base in CDCl$_3$) δ 2.03 (quin, J=7.0 Hz, 4 H, 2×CH$_2$CH$_2$CH$_2$), 2.37 (s, 3 H, NCH$_3$), 2.82 (t, J=7.6 Hz, 4 H, 2×CH$_2$NCH$_3$), 2.85 (s, 12 H, 2×N(CH$_3$)$_2$), 3.73 (q, J=6.1 Hz, 4 H, 2×CH$_2$NH), 6.54 (d, J=2.2 Hz, 2 H, H-5), 6.67 (dd, J=9.2, 2.4 Hz, 2 H, H-7), 7.31 (d, J=9.2 Hz, 2 H, H-8), 7.40 (t, J=7.6 Hz, 2 H, H-2), 7.86 (dd, J=8.2, 1.6 Hz, 2 H, H-1), 8.21 (s, 2 H, H-9), 8.81 (dd, J=7.2, 1.6 Hz, 2 H, H-3), 12.15 (t, J=5.0 Hz, 2 H, 2×CONH).

EXAMPLE 38

Preparation of Compound 38 of Table 1

A suspension of phenazine-1-carboxylic acid [Rewcastle and Denny, Synth. Comm., 1987, 17, 1171] (1.30 g, 5.8 mmol) in DMF (8 mL) was treated with 1,1'-carbonyldiimidazole (1.13 g, 7.0 mmol), and the mixture was stirred at 45° C. for 30 min. After cooling, the mixture was diluted with CH$_2$Cl$_2$/petroleum ether (1:1) to complete precipitation of the crude imidazolide, which was collected, washed with petroleum ether and dried. The crude imidazolide (1.33 g, 4.85 mmol) was added to an ice-cold solution of N,N-bis(3-aminopropyl)methylamine (0.35 g, 2.41 mmol) in THF (15 mL), and the mixture was stirred at 20° C. for 4 h. Volatiles were removed under reduced pressure, and the residue was partitioned between CH$_2$Cl$_2$ and aqueous Na$_2$CO$_3$.

The organic layer was washed with water, dried and evaporated, and the residue was chromatographed on alumina-90. Elution with CH$_2$Cl$_2$/MeOH (20:1), followed by crystallization from EtOAc/iPr$_2$O, gave bis[(phenazine-1-carboxamido)propyl]methylamine (38) (1.02 g, 63% from the acid), mp 153–154° C. $^1$H NMR [(CD$_3$)$_2$SO] δ 1.87 (quin, J=6.5 Hz, 4 H, 2×CH$_2$CH$_2$CH$_2$), 2.27 (s, 3 H, CH$_3$), 2.62 (t, J=6.7 Hz, 4 H, 2×CH$_2$NCH$_3$), 3.53 (q, J=5.7 Hz, 4 H, 2×CH$_2$NH), 7.5–7.8 (m, 4 H, ArH), 7.8–8.1 (m, 6 H, ArH), 8.16 (d, J=8.6 Hz, 2 H, ArH), 8.47 (d, J=6.9 Hz, 2 H, ArH), 10.14 (t, J=5.0 Hz, 2 H, 2×NH). Treatment with MeOH/EtOAc/HCl (1 equiv.) gave the monohydrochloride salt, mp (MeOH/EtOAc) 233–235° C. Anal. (C$_{33}$H$_{31}$N$_7$O$_2$.HCl.0.5H$_2$O) C,H,N,Cl.

EXAMPLE 39

Preparation of Compound 39 of Table I

Activation and coupling of phenazine-2-carboxylic acid as above gave bis[(phenazine-2-carboxamido)propyl] methylamine (39), as a yellow solid (88%) mp 196–197.5° C. $^1$H NMR (CDCl$_3$) δ 1.90–1.96 (m, 4 H, 2×CH$_2$CH$_2$CH$_2$), 2.34 (s, 3 H, NCH$_3$), 2.64 (t, J=6.2 Hz, 4 H, 2×CH$_2$NCH$_3$), 3.71 (q, J=6.0 Hz, 2 H, 2×CH$_2$NH), 7.66 (ddd, J=8.6, 6.6, 1.5 Hz, 2 H, H-7 or H-8), 7.72 (ddd, J=8.7, 6.6, 1.5 Hz, 2 H, H-8 or H-7), 7.99 (dd, J=8.7, 1.3 Hz, 2 H, H-6 or H-9), 8.12 (dd, J=8.4, 1.3 Hz, 2 H, H-9 or H-6), 8.16, (m, 4 H, H-4 and NH), 8.21 (dd, J=9.1, 1.9 Hz, 2H, H-3) and 8.44 (d, J=1.6 Hz, 2 H, H-1). Anal. (C$_{33}$H$_{31}$N$_7$O$_2$) C,H,N HRMS (FAB$^+$) M/z calcd for C$_{33}$H$_{32}$N$_7$O$_2$ 558.2617 (MH$^+$), found 558.2599.

EXAMPLE 40

Preparation of Compound 40 of Table I

Activation and coupling of the known [Rewcastle et al.,J. Med. Chem., 1987, 30, 843] 6-methylphenazine-1-carboxylic acid as above gave bis [(6-methylphenazine-1-carboxamido)propyl]methylamine (40) (47%), mp (HCl salt) 228–230° C. (MeOH/EtOAc). $^1$H NMR (CDCl$_3$) δ 2.06 (quin, J=6.9 Hz, 4 H, 2×CH$_2$CH$_2$CH$_2$), 2.39 (s, 3 H, N CH$_3$), 2.79 (s, 6 H, 2×ArCH$_3$), 2.81 (t, J=7.0 Hz, 4 H, 2×CH$_2$NCH$_3$), 3.75 (q, J=6.1 Hz, 4 H, 2×CH$_2$NH), 7.42 (t, J=7.8 Hz, 2 H, H-8), 7.61 (d, J=8.8 Hz, 2 H, 2×ArH), 7.87 (dd, J=8.5, 7.1 Hz, 4 H, H-3, 2×ArH), 8.27 (dd, J=8.7, 1.5 Hz, 2 H, H-4), 8.88 (dd, J=7.0, 1.5 Hz, 2 H, H-2), 10.93 (br s, 2 H, 2×CONH).

EXAMPLE 41

Preparation of Compound 41 of Table I

Activation and coupling of the known [Rewcastle et al.,J. Med. Chem., 1987, 30, 843] 6-chlorophenazine-1-carboxylic acid as above gave bis [(6-chlorophenazine-1-carboxamido)propyl]methylamine (41) (56%), mp (CH$_2$Cl$_2$/MeOH) 198–200° C. $^1$H NMR (CDCl$_3$) δ 2.01–2.06 (m, 4 H, 2×CH$_2$CH$_2$CH$_2$), 2.37 (s, 3 H, NCH$_3$), 2.73 (t, J=7.2 Hz, 4 H, 2×CH$_2$NCH$_3$), 3.72 (q, J=6.2 Hz, 2 H, 2×CH$_2$NH), 7.62 (dd, J=8.7, 7.2 Hz, 2 H, H-8), 7.74 (dd, J=7.2, 1.2 Hz, 2 H, H-7 or H-9), 7.91 (dd, J=8.8, 1.2 Hz, 2 H, H-9 or H-7), 7.93 (dd, J=8.7, 7.1 Hz, 2 H, H-3), 8.39 (dd, J=8.7, 1.6 Hz, 2 H, H-4), 8.88 (dd, J=7.1, 1.6 Hz, 2 H, H-2), 10.59 (br t, J=5.1 Hz, 2H, 2×CONH), HRMS (FAB$^+$) m/z calcd for C$_{33}$H$_{29}$Cl$_2$N$_7$O$_4$ 626.1838 (MH$^+$), found 618.1840. Anal. (C$_{33}$H$_{29}$Cl$_2$N$_7$O$_2$) C, H, N, Cl).

EXAMPLE 42

Preparation of Compound 42 of Table I

Activation and coupling of the known [Rewcastle et al., *J. Med. Chem.*, 1987, 30, 843] 7-methylphenazine-1-carboxylic acid as above gave bis [(7-methylphenazine-1-carboxamido)propyl]methylamine (42) (63%), mp (HCl salt) 213–215° C. (MeOH/EtOAc). $^1$H NMR (CDCl$_3$) δ 2.06 (quin, J=6.9 Hz, 4 H, 2×CH$_2$CH$_2$CH$_2$), 2.38 (s, 3 H, NCH$_3$), 2.44 (s, 6 H, 2×ArCH$_3$), 2.79 (t, J=7.4 Hz, 4 H, 2×CH$_2$NCH$_3$), 3.75 (q, J=6.2 Hz, 4 H, 2×CH$_2$NH), 7.40 (dd, J=8.9, 1.6 Hz, 2 H, H-8), 7.62 (br s, 2 H, H-6), 7.77 (d, J=8.9 Hz, 2 H, H-9), 7.86 (dd, J=8.5, 7.1 Hz, 2 H, H-3), 8.22 (dd, J=8.6, 1.5 Hz, 2 H, H-4), 8.86 (dd, J=7.2, 1.5 Hz, 2 H, H-2), 10.85 (t, J=4.9 Hz, 2 H, 2×CONH). Anal. (C$_{35}$H$_{35}$N$_7$O$_2$.HCl) C, H, N, Cl.

EXAMPLE 43

Preparation of Compound 43 of Table I

Activation and coupling of the known [Rewcastle et al., *J. Med. Chem.*, 1987, 30, 843] 7-methoxyphenazine-1-carboxylic acid as above gave bis[(7-methoxyphenazine-1-carboxamido)propyl]methylamine (43) (60%), mp (HCl salt) 225–229° C. (MeOH/EtOAc). $^1$H NMR (CDCl$_3$) δ 2.03 (quin, J=6.9 Hz, 4 H, 2×CH$_2$CH$_2$CH$_2$), 2.37 (s, 3 H, NCH$_3$), 2.74 (t, J=7.2 Hz, 4 H, 2×CH$_2$NCH$_3$), 3.73 (q, J=6.3 Hz, 4 H, 2×CH$_2$NH), 3.93 (s, 6 H, 2×ArOCH$_3$), 7.10 (d, J=2.7 Hz, 2 H, H-6), 7.28 (dd, J=9.1, 3.1 Hz, 2 H, 2×ArH), 7.78 (d, J=9.5 Hz, 2 H, H-9), 7.83 (dd, J=8.7, 1.5 Hz, 2 H, H-8), 8.17 (dd, J=8.6, 1.5 Hz, 2 H, 2×ArH), 8.81 (J=7.2, 1.5 Hz, 2 H, H-2), 10.77 (t, J=4.6 Hz, 2 H, 2×CONH). Anal. (C$_{35}$H$_{35}$N$_7$O$_4$.2HCl.3H$_2$O) C, H, N.

EXAMPLE 44

Preparation of Compound 44 of Table I

Activation and coupling of the known [Rewcastle et al., *J. Med. Chem.*, 1987, 30, 843] 7-chlorophenazine-1-carboxylic acid as above gave bis[(7-chlorophenazine-1-carboxamido)propyl]methylamine (44) (71%), mp (CH$_2$Cl$_2$/MeOH) 173–175° C. $^1$H NMR (CDCl$_3$) δ 1.99–2.06 (m, 4 H, CH$_2$CH$_2$CH$_2$), 2.37 (s, 3 H, NCH$_3$), 2.73 (t, J=7.2 Hz, 4 H, CH$_2$NCH$_3$), 3.73 (q, J=6.5, 5.8 Hz, 2 H, CH$_2$NH), 7.54 (dd, J=9.3, 2.4 Hz, 2 H, H-8), 7.84 (d, J=9.3 Hz, 2 H, H-9), 7.90 (d, J=2.5 Hz, 2 H, H-6), 7.92 (dd, J=8.7, 7.1 Hz, 2 H, H-3), 8.20 (dd, J=8.7, 1.6 Hz, 2 H, H-4), 8.88 (dd, J=7.1, 1.5 Hz, 2 H, H-2), 10.54 (br t, J=5.1 Hz, 2 H, 2×CONH). HRMS (FAB$^+$) m/z calcd for C$_{33}$H$_{29}$Cl$_2$N$_7$O$_4$ 626.1838 (MH$^+$), found 618.1844. Anal. (C$_{33}$H$_{29}$Cl$_2$N$_7$O$_2$) C, H, N, Cl.

EXAMPLE 45

Preparation of Compound 45 of Table I

Activation and coupling of the known [Rewcastle and Denny, *Synth. Comm.*, 1987, 17, 1171] 8-methylphenazine-1-carboxylic acid as above gave bis [(8-methylphenazine-1-carboxamido)propyl]methylamine (45) (76%), mp (HCl salt) 215° C. (dec) (MeOH/EtOAc). $^1$H NMR (CDCl$_3$) δ 2.16 (quin, J=6.6 Hz, 4 H, 2×CH$_2$CH$_2$CH$_2$), 2.52 (s, 9 H, NCH$_3$, 2×ArCH$_3$), 2.93 (m, 4 H, 2×CH$_2$NCH$_3$), 3.76 (q, J=6.3 Hz, 4 H, 2×CH$_2$NH), 7.41 (d, J=8.6 Hz, 2 H, H-6), 7.77 (br s, 2 H, H-9), 7.86 (dd, J=8.5, 7.1 Hz, 4 H, H-3,7), 8.26 (dd, J=8.6, 1.5 Hz, 2 H, H-4), 8.87 (dd, J=7.7, 1.5 Hz, 2 H, H-2), 11.00 (br s, 2 H, 2×CONH).

EXAMPLE 46

Preparation of Compound 46 of Table I

Activation and coupling of the known [Rewcastle and Denny, *Synth. Comm.*, 1987, 17, 1171] 8-methoxyphenazine-1-carboxylic acid as above gave bis [(8-methoxyphenazine-1-carboxamido)propyl]methylamine (46) (99%), mp 182–186° C. (dec.) (MeOH/EtOAc). $^1$H NMR (CDCl$_3$) δ 1.92 (m, 4 H, 2×CH$_2$), 2.30 (s, 3 H, NCH$_3$), 2.71 (m, 4 H, 2×CH$_2$), 3.60 (q, J=6.1 Hz, 4 H, 2×CH$_2$NH), 3.85 (s, 6 H, 2×ArOCH$_3$), 7.06 (s, 2 H, H-9), 7.19 (dd, J=9.4, 2.4 Hz, 2 H, H-7), 7.69 (d, J=9.4 Hz, 2 H, H-6), 7.80 (dd, J=8.6, 7.2 Hz, 2 H, H-3), 8.11 (dd, J=8.5, 1.4 Hz, 2 H, H-4), 8.48 (J=7.1, 1.5 Hz, 2 H, H-2), 10.39 (t, J=5.4 Hz, 2 H, 2×CONH). Anal. (C$_{35}$H$_{35}$N$_7$O$_4$) C, H, N.

EXAMPLE 47

Preparation of Compound 47 of Table I

Activation and coupling of the known [Rewcastle et al., *J. Med. Chem.*, 1987, 30, 843] 9-methylphenazine-1-carboxylic acid as above gave bis[(9-methylphenazine-1-carboxamido)propyl]methylamine (47) (82%), mp (HCl salt) 262–264° C. (MeOH/EtOAc). $^1$H NMR (CDCl$_3$) δ 1.99 (quin, J=7.3 Hz, 4 H, 2×CH$_2$CH$_2$CH$_2$), 2.32 (s, 3 H, NCH$_3$), 2.60 (t, J=7.4 Hz, 4 H, 2×CH$_2$NCH$_3$), 2.79 (s, 6 H, 2×ArCH$_3$), 3.75 (q, J=6.7 Hz, 4 H, 2×CH$_2$NH), 7.56 (d, J=6.73 Hz, 2 H, H-8), 7.65 (dd, J=8.7, 7.2 Hz, 2 H, H-7), 7.89 (dd, J=8.7, 7.2 Hz, 2 H, H-3), 7.97 (d, J=8.6 Hz, 2 H, H-6), 8.27 (dd, J=8.7, 1.5 Hz, 2 H, H-4), 8.93 (dd, J=7.2, 1.5 Hz, 2 H, H-2), 10.94 (br s, 2 H, 2×CONH). Anal. (C$_{35}$H$_{35}$N$_7$O$_2$HCl) C, H, N, Cl.

EXAMPLE 48

Preparation of Compound 48 of Table I

Activation and coupling of 9-methylphenazine-1-carboxylic acid as above, and subsequent coupling with 1,4-bis(aminopropyl)piperazine gave a crude product, which was dissolved in MeOH/AcOH, treated with charcoal/Celite and filtered, then basified with Et$_3$N to give bis[(9-methylphenazine-1-carboxamido)propyl]-1,4-piperazine (48) (45%) as the free base, mp (MeOH) 252–253° C. $^1$H NMR (hydrochloride salt in D$_2$O) δ 2.07 (quin, J=7.5 Hz, 4 H, 2×CH$_2$CH$_2$CH$_2$), 2.89 (s, 6 H, 2×CH$_3$), 3.10 (t, J=7.0 Hz, 6 H, 3×CH$_2$), 3.29 (br s, 6 H, 3×CH$_2$), 3.64 (t, J=6.7 Hz, 6 H, 3×CH$_2$), 7.92–7.98 (m, 4 H, 4×ArH), 8.11 (dd, J=9.6, 7.2 Hz, 2 H, 2×ArH), 8.15 (d, J=8.4 Hz, 2 H, 2×ArH), 8.45 (dd, J=8.7, 1.3 Hz, 2 H, 2×ArH), 8.69 (dd, J=7.1, 1.3 Hz, 2 H, H-2). Anal. (C$_{38}$H$_{40}$N$_8$O$_2$.0.5 H$_2$O) C,H,N.

EXAMPLE 49

Preparation of Compound 49 of Table I

Activation and coupling of 9-methylphenazine-1-carboxylic acid as above, and subsequent coupling with ethylenetriamine gave a crude product, which was dissolved in MeOH/AcOH, treated with charcoal/Celite and filtered, then basified with Et$_3$N to give bis[(9-methylphenazine-1-carboxamido)ethyl]-1,4-ethylenediamine (49) (33%) mp (HCl salt from MeOH/EtOAc) 281° C. (dec). $^1$H NMR (hydrochloride salt in D$_2$O) δ 2.89 (s, 6 H, 2×CH$_3$), 3.38 (m, 8 H, 4×CH$_2$), 3.90 (q, J=6.9 Hz, 4 H, 2×CH$_2$), 7.90 (m, 4 H, 4×ArH), 8.07 (dd, J=8.6, 7.2 Hz, 2H, H-3), 8.13 (d, J=8.2 Hz, 2 H, 2×ArH), 8.44 (dd, J=8.7, 1.4 Hz, 2 H, 2×ArH), 8.71 (dd, J=7.1, 1.4 Hz, 2 H, H-2). Anal. HRMS (FAB$^+$) m/z calcd for C$_{34}$H$_{34}$N$_8$O$_2$ 586.61, found 587.29.

EXAMPLE 50

Preparation of Compound 50 of Table I

Activation and coupling of the known [Rewcastle et al.,*J. Med. Chem.,* 1987, 30, 843] 9-methoxyphenazine-1-carboxylic acid as above gave bis[(9-methoxyphenazine-1-carboxamido)propyl]methylamine (50) (86%), mp (CH$_2$Cl$_2$/MeOH) 220–222° C. $^1$H NMR (CDCl$_3$) δ 1.99–2.05 (m, 4 H, 2×CH$_2$CH$_2$CH$_2$), 2.39 (s, 3 H, NCH$_3$), 2.73 (t, J=7.6 Hz, 4 H, 2×CH$_2$NCH$_3$), 3.66 (q, J=6.0 Hz, 2 H, 2×CH$_2$NH), 3.90 (s, 6 H, OCH$_3$), 6.60 (dd, J=6.7, 1.9 Hz, 2 H, H-6 or H-8), 7.32–7.38 (m, 4 H, H-7 and H-8 or H-6), 7.84 (dd, J=8.7, 7.2 Hz, 2 H, H-3), 8.11 (dd, J=8.7, 1.5 Hz, 2 H, H-4), 8.83 (dd, J=7.1, 1.5 Hz, 2 H, H-2), 11.12 (br t, J=4.7 Hz, 2 H, NH). HRMS (FAB$^+$) m/z calcd for C$_{35}$H$_{35}$N$_7$O$_4$ 618.2829 (MH$^+$), found 618.2847. Anal. (C$_{35}$H$_{35}$N$_7$O$_4$) C, H, N.

EXAMPLE 51

Preparation of Compound 51 of Table I

Activation and coupling of the known [Atwell et al., Eur. Pat. Appl. EP 172,744, February 1986; *Chem Abstr.* 1986, 105, 97496p] 9-phenoxyphenazine-1-carboxylic acid as above gave bis[(9-phenoxyphenazine-1-carboxamido) propyl]methylamine (51) as an orange oil (51%). $^1$H NMR (CDCl$_3$) δ 1.69–1.73 (m, 4 H, 2×CH$_2$CH$_2$CH$_2$), 1.97 (s, 3 H, NCH$_3$), 2.31 (t, J=7.3 Hz, 4 H, 2×CH$_2$NCH$_3$), 3.43 (q, J=6.4 Hz, 2 H, 2×CH$_2$NH), 7.11–7.14 (m, 6 H, H-2', H-6' and H-6 or H-8), 7.18 (t, J=7.5 Hz, 2 H, H-4'), 7.39 (t, J=7.5 Hz, 4 H, H-3' and H-5'), 7.69 (dd, J=8.7, 7.6 Hz, 2 H, H-7), 7.89 (dd, J=8.7, 1.0 Hz, 2 H, H-3, H-8 or H-6), 8.26 (dd, J=8.7, 1.5 Hz, 2 H, 11–4), 8.90 (dd, J=7.1, 1.5 Hz, 2 H, H-2) and 10.98 (br t, J=5.2 Hz, 2 H, 2×CONH); HRMS (FAB$^+$) m/z calcd for C$_{45}$H$_{40}$N$_7$O$_4$ 742.3142 (MH$^+$), found 742.3147.

EXAMPLE 52

Preparation of Compound 52 of Table I

Activation and coupling of the known [Rewcastle et al., *Synth. Comm.,* 1987, 17, 1171] 9-fluorophenazine-1-carboxylic acid as above gave bis[(9-fluorophenazine-1-carboxamido)propyl]methylamine (52) (87%), mp (CH$_2$Cl$_2$/MeOH) 186–187° C. $^1$H NMR (CDCl$_3$) δ 2.00–2.04 (m, 4 H, CH$_2$CH$_2$CH$_2$), 2.36 (s, 3 H, NCH$_3$), 2.72 (t, J=7.4 Hz, 4 H, CH$_2$NCH$_3$), 3.73 (q, J=6.2 Hz, 2 H, CH$_2$NH), 7.30–7.35 (m, 2 H, H-7 or H-8), 7.54–7.60 (m, 2 H, H-8 or H-7), 7.84 (d, J=9.0 Hz, 2 H, H-6), 7.94 (dd, J=8.7, 7.0 Hz, 2 H, H-3), 8.25 (dd, J=8.7, 1.5 Hz, 2 H, H-4), 8.95 (dd, J=7.0, 1.5 Hz, 2 H, H-2), 10.94 (br t, J=5.0 Hz, 2 H, 2×CONH). HRMS (FAB$^+$) m/z calcd for C$_{33}$H$_{29}$F$_2$N$_7$O$_4$ 594.2429 (MH$^+$), found 594.2403. Anal. (C$_{33}$H$_{29}$F$_2$N$_7$O$_2$·0.5H$_2$O) C, H, N.

EXAMPLE 53

Preparation of Compound 53 of Table I

Activation and coupling of the known [Rewcastle et al.,*J. Med. Chem.,* 1987, 30, 843] 9-chlorophenazine-1-carboxylic acid as above gave bis[(9-chlorophenazine-1-carboxamido)propyl]methylamine (53) (86%), mp (CH$_2$Cl$_2$/MeOH) 169–171.5° C. $^1$H NMR (CDCl$_3$) δ 1.99–2.03 (m, 4 H, 2×CH$_2$CH$_2$CH$_2$), 2.32 (s, 3 H, NCH$_3$), 2.62 (t, J=7.4 Hz, 4 H, 2×CH$_2$NCH$_3$), 3.70 (q, J=6.2 Hz, 2 H, CH$_2$NH), 7.64 (dd, J=8.8, 7.4 Hz, 2 H, H-7), 7.80 (dd, J=7.2, 1.0 Hz, 2 H, H-6 or H-8), 7.95 (dd, J=8.7, 7.2 Hz, 2 H, H-3), 8.01 (dd, J=8.7, 1.0 Hz, 2 H, H-8 or H-6), 8.27 (dd, J=8.7, 1.5 Hz, 2 H, H-4), 8.99 (dd, J=7.2, 1.5 Hz, 2 H, H-2), 10.94 (br t, J=5.0 Hz, 2 H, 2×CONH). HRMS (FAB$^+$) m/z calcd for C$_{33}$H$_{29}$Cl$_2$N$_7$O$_4$ 626.1838 (MH$^+$), found 618.1848. Anal. (C$_{33}$H$_{29}$Cl$_2$N$_7$O$_2$) C, H, N.

EXAMPLE 54

Preparation of Compound 54 of Table I

A solution of 9-fluorophenazine-1-carboxylic acid [Rewcastle et al., *J. Synth Comm,* 1987, 17, 1171] (200 mg, 0.8 mmol) in Me$_2$NH (40% aqueous, 20 mL) was heated at 100° C. in a bomb for 3 h. The resulting intensely purple solution was diluted with water and then neutralized with AcOH. The aqueous solution was then extracted with CHCl$_3$ (3×50 mL) until all color was extracted. The organic layer was further washed with water (1×150 mL), then dried over Na$_2$SO$_4$ and the solvent removed under reduced pressure. The resulting purple solid was dissolved in a minimal amount of CH$_2$Cl$_2$, and peteoleum ether was added until crystallization occurred, giving 9-(dimethylamino) phenazine-1-carboxylic acid as dark purple needles (210 g, 95%), mp 186–187.5° C. $^1$H NMR (CDCl$_3$) δ 3.16 [s, 6 H, N(CH$_3$)$_2$], 7.26 (dd, J=6.8, 1.8 Hz, 1 H, H-6 or H-8), 7.81–7.88 (m, 2 H, H-7 and H-8 or H-6), 8.01 (dd, J=8.7, 7.0 Hz, 1 H, H-3), 8.48 (dd, J=8.7, 1.2 Hz, 1 H, H-4) and 8..91 (dd, J=7.0, 1.3 Hz, 1 H, H-2). Anal. (C$_{15}$H$_{13}$N$_3$O$_2$) C, H, N. Activation and coupling of this as above gave bis[((9-dimethylamino)phenazine-1-carboxamido)propyl] methylamine (54) as a red-purple oil (78%). $^1$H NMR (CDCl$_3$) δ 1.91–2.00 (m, 4 H, 2×CH$_2$CH$_2$CH$_2$), 2.29 (s, 3 H, NCH$_3$), 2.57 (t, J=7.3 Hz, 4 H, CH$_2$NCH$_3$), 3.05 (s, 12 H, 2×N(CH$_3$)$_2$, 3.68 (q, J=6.5 Hz, 2 H, CH$_2$NH), 7.07 (dd, J t 7.2, 1.3 Hz, 2 H, H-6 or H-8), 7.65 (dd, J=8.7, 7.3 Hz, 2 H, H-7), 7.70 (dd, J=8.7, 1.3 Hz, 2 H, H-8 or H-6), 7.90 (dd, J=8.6, 7.1 Hz, 2 H, H-3), 8.27 (dd, J=8.6, 1.4 Hz, 2 H, H-4), 8.87 (dd, J=7.1, 1.4 Hz, 2 H, H-2) and 10.99 (br t, J=5.1 Hz, 2 H, 2×CONH); HRMS (FAB$^+$) m/z calcd for C$_{37}$H$_{42}$N$_9$O$_2$ 644.3461 (MH$^+$), found 644.3485.

EXAMPLE 55

Preparation of Compound 55 of Table 1

The bis(5-fluoro) analogue (11) was heated at 100° C. in excess 40% aqueous dimethylamine/MeOH for 8 weeks in a pressure vessel, the solvents were then removed by evaporation, and the residue was chromatographed on alumina to give bis[3-(5-(dimethylamino)acridine-4-carboxamido)propyl]methylamine (55) (60%) as a foam. $^1$H NMR (CDCl$_3$) δ 1.97 (quin, J=7.3 Hz, 4 H, 2×CH$_2$CH$_2$CH$_2$), 2.30 (s, 3 H, NCH$_3$), 2.59 (t, J=7.3 Hz, 4 H, CH$_2$N(CH$_3$)CH$_2$), 3.01 (s, 12 H, 2×N(CH$_3$)$_2$), 3.68 (q, J=6.7 Hz, 4 H, 2×CH$_2$NH), 7.12 (dd, J=7.2, 0.9 Hz, 2 H, H-6), 7.39 (dd, J=8.4, 7.3 Hz, 2 H, H-7), 7.51 (dd, J=8.2, 0.8 Hz, 2 H, H-8), 7.62 (dd, J=8.3, 7.2 Hz, 2 H, H-2), 8.04 (dd, J=8.4, 1.4 Hz, 2 H, H-1), 8.70 (s, 2 H, H-9), 8.91 (dd, J=7.1, 1.5 Hz, 2 H, H-3), 11.94 (br s, 2 H, 2×CONH). Anal. (C$_{39}$H$_{43}$N$_7$O$_2$·H$_2$O) C, H.

EXAMPLE 56

Preparation of Compound 56 of Table 1

The bis(7-fluoro) analogue (27) was heated at 100° C. in excess 40% aqueous dimethylamine/MeOH for 6 weeks in a pressure vessel, the solvents were then removed by evaporation, and the residue was chromatographed on alumina to give bis[3-(7-(dimethylamino)acridine-4-carboxamido)propyl]methylamine (56) (89%) as a foam. $^1$H NMR (CDCl$_3$) δ 2.08 (quin, J=7.0 Hz, 4 H, 2×CH$_2$CH$_2$CH$_2$), 2.40 (s, 3 H, NCH$_3$), 2.86 (t, J=7.6 Hz, 4 H, CH$_2$N(CH$_3$)CH$_2$), 2.99 (s, 12 H, 2×N(CH$_3$)$_2$), 3.75 (q, J=6.1 Hz, 4 H, 2×CH$_2$NH), 6.30 (d, J=2.8 Hz, 2 H, H-8), 7.18 (dd, J=9.5, 2.8 Hz, 2 H, H-6), 7.44 (dd, J=8.2, 7.2 Hz, 2 H, H-2), 7.67 (d, J=9.5 Hz, 2 H, H-5), 7.82 (dd, J=8.5, 1.4 Hz, 2 H, H-1), 8.13 (s, 2 H, H-9), 8.69 (dd, J=7.1, 1.5 Hz, 2 H, H-3), 11.84 (t, J=5.0 Hz, 2 H, 2×CONH). Anal. (C$_{39}$H$_{43}$N$_7$O$_2$.H$_2$O) C, H, N.

EXAMPLE 57

Preparation of Compound 57 of Table 1 by the Method of Scheme 1

Reaction of 2,5-dimethylaniline and 2-iodoisophthalic acid under the conditions described in Example 1 gave crude N-(2,5-dimethyphenyl)isophthalic acid. This was cyclized directly with PPA to give 5,8-dimethylacridone-4-carboxylic acid (46% overall): mp (MeOH/H$_2$O) 343–346° C.; $^1$H NMR [(CD$_3$)$_2$SO] δ 2.87 (s, 6 H, 2×CH$_3$), 6.98 (d, J=7.3 Hz, 1 H, H-6), 7.33 (t, J=7.7 Hz, 1 H, H-2), 7.51 (d, J=7.5 Hz, 1 H, H-7), 8.41 (dd, J=7.6, 1.6 Hz, 1 H, H-1), 8.46 (dd, J=7.9, 1.6 Hz, 1 H, H-3), 12.00 (br s, 1 H, NH), 13.93 (br s, 1 H, COOH). Anal. (C$_{16}$H$_{13}$NO$_3$) C, H, N.

Reduction of 5,8-dimethylacridone-4-carboxylic acid as above gave 5,8-dimethylacridine-4-carboxylic acid (82%): mp (MeOH/H$_2$O) 239–241° C.; $^1$H NMR [(CD$_3$)$_2$SO] δ 2.78 (s, 3 H, CH$_3$), 2.83 (s, 3 H, CH$_3$), 7.50 (d, J=6.7 Hz, 1 H, H-6), 7.81 (d, J=7.0 Hz, 1 H, H-7), 7.88 (dd, J=8.3, 7.2 Hz, 1 H, H-2), 8.62 (dd, J=8.4, 1.4 Hz, 1 H, H-1), 8.76 (dd, J=7.0, 1.4 Hz, 1 H, H-3), 8.61 (s, 1 H, H-9) 17.48 (s, 1 H, COOH). Anal. (C$_{16}$H$_{13}$NO$_2$) C, H, N.

Activation and coupling of 5,8-dimethylacridine-4-carboxylic acid as above gave bis-[3-(5,8-dimethylacridine-4-carboxamido)propyl]methylamine (57) (79%), mp (CH$_2$Cl$_2$/hexane) 119–124° C. $^1$H NMR (CDCl$_3$) δ 2.00 (quin, J=7.3 Hz, 4 H, 2×CH$_2$CH$_2$CH$_2$), 2.31 (s, 3 H, NCH$_3$), 2.60 (t, J=7.4 Hz, 4 H, CH$_2$N(CH$_3$)CH$_2$), 2.70 (s, 6 H, 2×CH$_3$), 2.73 (s, 6 H, 2×CH$_3$), 3.70 (q, J=6.7 Hz, 4 H, 2×CH$_2$NH), 7.16 (d, J=7.1 Hz, 2 H, H-6), 7.40 (d, J=6.8 Hz, 2 H, H-7), 7.61 (dd, J=8.1, 7.3 Hz, 2 H, H-2), 8.06 (dd, J=8.3, 1.4 Hz, 2 H, H-1), 8.81 (s, 2 H, H-9), 8.93 (dd, J=7.1, 1.5 Hz, 2 H, H-3), 11.81 (br s, 2 H, 2×CONH). Anal. (C$_{39}$H$_{41}$N$_5$O$_2$) C, H, N.

EXAMPLE 58

Preparation of Compound 58 of Table 1 by the Method of Scheme 1

Reaction of 3-methylanthranilic acid and 2-bromo-4-methylbenzoic acid under the conditions described in Example 1 gave crude N-(2-methyl-6-carboxyphenyl)-4-methylanthranilic acid. This was cyclized in PPA as above to give 1,5-dimethylacridone-4-carboxylic acid (49% overall), mp (MeOH) 317–318° C.; $^1$H NMR [(CD$_3$)$_2$SO] δ 2.51 (s, 3 H, CH$_3$), 2.91 (s, 3 H, CH$_3$), 7.07 (d, J=8.1 Hz, 1 H, H-2), 7.20 (t, J=7.0 Hz, 1 H, H-7), 7.51 (d, J=7.0 Hz, 1 H, H-6), 8.05 (d, J=7.7 Hz, 1 H, H-3), 8.26 (d, J=7.8 Hz, 1 H, H-8), 12.45 (br s, 1 H, CO$_2$H) Anal. (C$_{16}$H$_{13}$NO$_3$) C, H, N.

Reduction of 1,5-dimethylacridone-4-carboxylic acid as above gave 1,5-dimethylacridine-4-carboxylic acid (98%), mp (MeOH) 267° C. (dec.); $^1$H NMR [(CD$_3$)$_2$SO] δ 2.83 (s, 3 H, CH$_3$), 2.93 (s, 3 H, CH$_3$), 7.70 (dd, J=8.1, 7.2 Hz, 2 H, H-2,7), 7.95 (d, J=6.7 Hz, 1 H, H-6), 8.25 (d, J=8.4 Hz, 1 H, H-8), 8.67 (d, J=7.3 Hz, 1 H, H-3 ), 9.63 (s, 1 H, H-9), 17.55 (s, 1 H, CO$_2$H). Anal. (C$_{16}$H$_{13}$NO$_2$) C, H, N.

Activation and coupling of 1,5-dimethylacridine-4-carboxylic acid as above gave bis-[3-(1,5-dimethylacridine-4-carboxamido)propyl]methylamine (58) (82%), mp (CH$_2$Cl$_2$/hexane) 110–116° C. (dec.); $^1$H NMR (CDCl$_3$) δ 2.01 (quin, J=6.9 Hz, 4 H, 2×CH$_2$CH$_2$CH$_2$), 2.34 (s, 3 H, NCH$_3$), 2.64 (br t, 4 H, CH$_2$N(CH$_3$)NCH$_2$), 2.77 (s, 12 H, 4×CH$_3$), 3.69 (q, J=6.7 Hz, 4 H, 2×CH$_2$NH), 7.36 (dd, J=8.4, 6,9 Hz, 2 H, H-7), 7.42 (dd, J=7.2, 0.8 Hz, 2 H, H-6), 7.52 (d, J=6.8 Hz, 2 H, H-8), 7.75 (d, J=8.4 Hz, 2 H, H-2), 8.80 (s, 2 H, H-9), 8.8 (d, J=8.6 Hz, 2 H, H-3), 11.80 (br s, 2 H, 2×CONH). Anal. (C$_{39}$H$_{41}$N$_5$O$_2$.2H$_2$O) C, H, N.

EXAMPLE 59

Preparation of Compound 59 of Table 1 by the Method of Scheme 1

Reaction of 2-methyl-5-chloroaniline and 2-iodoisophthalic acid acid under the conditions described in Example 1 gave crude N-(2-methyl-5-chlorophenyl) isophthalic acid. This was cyclised directly with PPA to give 8-chloro-5-methylacridone-4-carboxylic acid (51% overall): mp (MeOH) 325–330° C.; $^1$H NMR [(CD$_3$)$_2$O] δ 2.50 (s, 3 H, CH$_3$; overlapped with DMSO peak), 7.81 (d, J=7.2 Hz, 1 H, H-6), 7.38 (t, J=7.8 Hz, 1 H, H-2), 7.61 (d, J=7.7 Hz, 1 H, H-7), 8.43–8.48 (m, 2 H, H-1,3), 12.18 (br s, 1 H, NH), 14.10 (s, 1 H, CO$_2$H). Anal. (C$_{15}$H$_{10}$ClNO$_3$) C, H, N.

Reduction of 8-chloro-5-methylacridone-4-carboxylic acid as above gave 8-chloro-5-methyl acridine-4-carboxylic acid (84%): mp (MeOH) 259–260° C.; $^1$H NMR [(CD$_3$)$_2$SO] δ 2.81 (s, 3 H, CH$_3$), 7.86–7.95 (m, 3 H, H-1,2,3), 8.74 (d, J=8.4 Hz, 1 H, H-6), 8.80 (d, J=7.0 Hz, 1 H, H-7), 9.70 (s, 1 H, H-9), 16.83 (s, 1 H, CO$_2$H). Anal. (C$_{15}$H$_{10}$ClNO$_2$) C, H, N.

Activation and coupling of 8-chloro-5-methyl acridine-4-carboxylic acid as above gave bis-[3-(8-chloro-5-methylacridine-4-carboxamido)propyl]methylamine (59) (81%): mp (CH$_2$Cl$_2$/hexane) 212–215° C.; $^1$H NMR (CDCl$_3$) δ 1.98 (quin, J=7.3 Hz, 4 H, 2×CH$_2$CH$_2$CH$_2$), 2.02 (s, 3 H, NCH$_3$), 2.60 (t, J=7.4 Hz, 4 H, CH$_2$N (CH$_3$)CH$_2$), 2.67 (s, 6 H, 2×CH$_3$), 3.70 (q, 4 H, 2×CH$_2$NH), 7.28 (dd, J=7.7, 0.9 Hz, 2 H, H-7), 7.32 (d, J=7.4 Hz, 2 H, H-6), 7.65 (dd, J=8.3, 7.2 Hz, 2 H, H-2), 8.07 (dd, J=8.6, 1.5 Hz, 2 H, H-1), 8.96 (dd, J=7.2, 1.5 Hz, 2 H, H-3), 9.01 (s, 2 H, H-9), 11.41 (t, J=5.3 Hz, 2 H, 2×CONH). Anal. (C$_{37}$H$_{35}$Cl$_2$N$_2$O$_5$.0.5H$_2$O) C, H, N, Cl.

EXAMPLE 60

Preparation of Compound 60 of Table 1 by the Method of Scheme 2

A mixture of 3-methylanthranilic acid (7.6 g, 50 mmol), methyl-4-chloro-2-iodo benzoate (19.2 g, 65 mmol), Cu and CuI (catalytic) in 2,3 dibutanol (20 mL) was heated with benzene (30 mL) in an oil bath. After the benzene had distilled off, N-ethylmorpholine (50 mL) was added and the stirred mixture was heated at 110° C. for 18 h, then diluted with dilute HCl, extracted into EtOAc, and filtered to remove Cu salts. The organic layer was separated and extracted into dilute NH$_4$OH, then the ammonium salt of the product precipitated. This was collected and stirred in dilute HCl, and the mixture was filtered and washed with water to give 2-[[(5-chloro-2-methoxycarbonyl)phenyl]amino]-3- methylbenzoic acid (6.6 g, 41%): mp (MeOH) 187–188.5° C.; $^1$H NMR [(CD$_3$)$_2$SO] δ 2.10 (s, 3 H, CH$_3$), 3.87 (s, 3 H, OCH$_3$), 6.12 (d, J=2.0 Hz, 1 H, H-6'), 6.79 (dd, J=8.6, 2.0 Hz, 1 H, H-4'), 7.29 (t, J=7.6 Hz, 1 H, H-5), 7.52 (d, J=7.4 Hz, 1 H, H-4), 7.74 (d, J=7.4 Hz, 1 H, H-6), 7.89 (d, J=8.5 Hz, 1 H, H-3'), 9.90 (br s, 1 H, NH). Anal. (C$_{16}$H$_{14}$ClNO$_4$) C, H, N, Cl.

A solution of 2-[[(5-chloro-2-methoxycarbonyl)phenyl]amino]-3-methylbenzoic acid (6.0 g, 18.8 mmol) in dry THF (100 mL) was treated with CDI (6.0 g, 37.6 mmol) at 20° C. for 18 h, and the solution was then added dropwise to a suspension of NaBH$_4$ (0.69 g, 5 equiv.) in H$_2$O (50 mL). When the reaction was complete (30 min, as monitored by TLC), the mixture was quenched with dilute HCl and extracted with CH$_2$Cl$_2$. The filtered CH$_2$Cl$_2$ layer was dried to give a crude product that was chromatographed on silica gel, eluting with a gradient of 1% MeOH in CH$_2$Cl$_2$ to give methyl 4-chloro-2-[N-(2-hydroxymethyl-6-methyl)phenylamino]benzoate (1.0 g, 17%), mp (CH$_2$Cl$_2$/hexane) 114–115° C. $^1$H NMR (CDCl$_3$) δ 1.78 (br s, 1 H, OH), 2.18 (s, 3 H, CH$_3$), 3.92 (s, 3 H, CO$_2$CH$_3$), 4.54 (dd, J=12.8, 4.3 Hz, 1 H, CHOH), 4.67 (dd, J=12.8, 4.3 Hz, 1 H, CHOH), 6.01 (d, J=2.0 Hz, 1 H, H-3), 6.63 (dd, J=8.3, 2.0 Hz, 1 H, H-5), 7.24–7.29 (m, 2 H, 2ArH), 7.35–7.39 (m, 1 H, ArH), 7.89 (d, J=8.6 Hz, 1 H, H-6), 9.22 (s, 1 H, NH). Anal. (C$_{16}$H$_{16}$ClNO$_3$) C, H, N.

A solution of methyl 4-chloro-2-[N-(2-hydroxymethyl-6-methyl)phenylamino]benzoate (0.72 g, 2.35 mmol) in EtOAc (100 mL) was heated under reflux for 7 h with MnO$_2$ (1 g). The mixture was filtered through celite to remove Mn residues, and the solvent was evaporated and the residue filtered through a column of silica gel in CH$_2$Cl$_2$ to give methyl-4-chloro-2-[N-(2-formyl-6-methyl)phenylamino]benzoate (0.7 g, 98%): mp (MeOH/H$_2$O) 81–82° C. $^1$H NMR (CDCl$_3$) δ 2.23 (s, 3 H, CH$_3$), 3.95 (s, 1 H, CO$_2$CH$_3$), 6.27 (d, J=2.0 Hz, 1 H, H-3), 6.70 (dd, J=8.7, 2.0 Hz, 1 H, H-5), 7.37 (t, J=7.6 Hz, 1 H, H-4'), 7.58 (d, J=7.9 Hz, 1 H, H-5'), 7.81(dd, J=7.7, 1.3 Hz, 1 H, H-3$^1$), 7.92 (d, J=8.6 Hz, 1 H, H-6), 9.68 (br s, 1 H, NH), 10.15 (s, 1 H, CHO). Analysis for methyl-4-chloro-2-[N-(2-formyl-6-methyl)phenylamino]benzoate. Anal. (C$_{16}$H$_{14}$ClNO$_3$) C, H,N.

A solution of 4-chloro-2-[N-(2-formyl-6-methyl)phenylamino]benzoate (0.65 g, 2.1 mmol) in trifluoroacetic acid (8 mL) was stirred at 40° C. for 4 h under nitrogen. Excess reagent was removed under reduced pressure at 40° C., and the residue was suspended in 2 N NaOH (25 mL) and EtOH (18 mL) and heated for 1 h until a clear solution was obtained. The cooled reaction mixture was neutralized with AcOH, and the resulting precipitate was collected, washed with water and dried to give 1-chloro-5-methylacridine-4-carboxylic acid (0.56 g, 96%), mp (MeOH/H$_2$O) 260° C. (dec.); $^1$H NMR (CDCl$_3$) δ 2.93 (s, 3 H, CH$_3$), 7.64 (dd, J=8.4, 7.9 Hz, 1 H, H-7), 7.83–7.86 (m, 2 H, H-2 & H-6 or H-8), 8.08 (d, J=8.6 Hz, 1 H, H-8 or H-6), 8.84 (d, J=7.8 Hz, 1 H, H-3), 9.4 (s, 1 H, H-9), 17.26 (s, 1 H, CO$_2$H). Anal. (C$_{15}$H$_{10}$ClNO$_2$) C, H, N.

Activation and coupling of 1-chloro-5-methylacridine-4-carboxylic acid as above gave bis[3-(1-chloro-5-methylacridine-4-carboxamido)propyl]methylamine (60) (84%), mp (CH$_2$Cl$_2$/hexane) 156–158.5° C. $^1$H NMR (CDCl$_3$) δ 8 1.85 (quin, J=7.2 Hz, 4 H, 2×CH$_2$CH$_2$CH$_2$), 2.32 (s, 3 H, NCH$_3$), 2.60 (t, 4 H, CH$_2$N(CH$_3$)CH$_2$), 2.74 (s, 6 H, 2×CH$_3$), 3.68 (q, J=6.7 Hz, 4 H, 2×CH$_2$NH), 7.38 (dd, J=8.3, 6.8 Hz, 2 H, H-7), 7.52 (d, J=6.8 Hz, 2 H, H-6), 7.65 (d, L =8.0 Hz, 2 H, H-2),7.76 (d, J=8.5 Hz, 2 H, H-8), 8.80 (d, J=8.0 Hz, 2 H, H-3), 9.04 (s, 2 H, H-9), 11.50 (br s, 2 H, 2×CONH). Analysis for bis[3-(1-chloro-5-methylacridine-4-carboxamido)propyl]methylamine (60). Anal. (C$_{37}$H$_{35}$Cl$_2$N$_5$O$_2$) C, H, N, Cl.

EXAMPLE 61

Preparation of Compound 61 of Table 1

Activation and coupling of the known [Rewcastle et al. *J. Med. Chem.* 1987, 30, 843] 3-methylphenazine-1-carboxylic acid gave bis[2-(3-methylphenazine-1-carboxamido)propyl]methylamine (61) as a yellow solid (84%), mp 75–78° C. (CH$_2$Cl$_2$/n-hexane). $^1$H NMR (CDCl$_3$) δ 2.03 (quin, J=7.0 Hz, 4 H, 2×CH$_2$CH$_2$CH$_2$), 2.37 (s, 3 H, NCH$_3$), 2.67 (d, J=0.9 Hz, 6 H, 2×CH$_3$), 2.73 (t, J=7.2 Hz, 4 H, CH$_2$N(CH$_3$)CH$_2$), 3.73 (q, J=6.3 Hz, 2 H, 2×CH$_2$NH), 7.62–7.70 (m, 4 H, H-7 and H-8), 7.98–8.03 (m, 6 H, H-6, H-9 and H-2 or H-4), 8.73 (d, J=2.1 Hz, 2 H, H-2) and 10.88 (br t, J=5.2 Hz, 2 H, 2×CONH), HRMS (FAB$^+$) m/z calcd for C$_{35}$H$_{36}$N$_7$O$_2$ 586.2930 (MH$^+$), found 586.2931. Anal. (C$_{35}$H$_{35}$N$_7$O$_2$.H$_2$O) C, H, N.

EXAMPLE 62

Preparation of Compound 62 of Table 1

Activation and coupling of the known [Rewcastle et al. *J. Med. Chem.* 1987, 30, 843] 3-chlorophenazine-1-carboxylic acid gave bis[(3-chlorophenazine-1-carboxamido)propyl]methylamine (62) as a yellow solid (76%), mp 169–170° C. (CH$_2$Cl$_2$/n-hexane). $^1$H NMR (CDCl$_3$) δ 2.02 (quin, J=6.9 Hz, 4 H, 2×CH$_2$CH$_2$CH$_2$), 2.36 (s, 3 H, NCH$_3$), 2.72 (t, J=7.3 Hz, 4 H, 2×CH$_2$NCH$_3$), 3.71 (q, J=6.3 Hz, 2 H, 2×CH$_2$NH), 7.69–7.76 (m, 4 H, H-7 and H-8), 7.94–8.00 (m, 4 H, H-6 and H-9), 8.20 (d, J=2.5 Hz, 2 H, H-4), 8.74 (d, J=2.5 Hz, 2 H, H-2) and 10.65 (br t, J=5.2 Hz, 2 H, 2×CONH), HRMS (FAB$^+$) m/z calcd for C$_{33}$H$_{29}$$^{35}$Cl$_2$N$_7$O$_2$ 626.1838 (MH$^+$), found 626.1824. Anal. C$_{33}$H$_{29}$Cl$_2$N$_7$O$_2$.H$_2$O) C, H, N.

EXAMPLE 63

Preparation of Compound 63 of Table 1

Activation and coupling of the known [Rewcastle et al. *J. Med. Chem.* 1987, 30, 843] 2-chlorophenazine-1-carboxylic acid gave bis[3-(2-chlorophenazine-1-carboxamido)propyl]methylamine (63) as a yellow solid (45%), mp 206–207° C. (CH$_2$Cl$_2$/n-hexane) $^1$H NMR (CDCl$_3$) δ 1.83 (quin, J=6.0 Hz, 4 H, 2×CH$_2$CH$_2$CH$_2$), 2.17 (s, 3 H, NCH$_3$), 2.72 (t, J=6.1 Hz, 4 H, CH$_2$N(CH$_3$)CH$_2$), 3.67 (q, J=6.0 Hz, 2 H, 2×CH$_2$NH), 7.03 (br t, J=5.9 Hz, 2 H, 2×CONH), 7.47 (d, J=9.4 Hz, 2 H, H-3 or H-4), 7.60–7.68 (m, 4 H, H-7 and H-8), 7.89 (d, J=9.3 Hz, 2 H, H-4 or H-3) 7.91–7.97 (m, 4 H, H-6 and H-9); HRMS (FAB$^+$) m/z calcd for C$_{33}$H$_{29}$$^{35}$ClN$_2$N$_7$O$_2$ 626.1838 (MH$^+$), found 626.1854. Anal. (C$_{33}$H$_{29}$Cl$_2$N$_7$O$_2$) C, H, N.

EXAMPLE 64

Preparation of Compound 64 of Table 1

Activation and coupling of the known [Rewcastle et al. *J. Med. Chem.* 1987, 30, 843] 8-chlorophenazine-1-carboxylic acid gave bis[3-(8-chlorophenazine-1-carboxamido)propyl]methylamine (64) as a pale yellow solid, (85%), mp 210–212° C. (CH$_2$Cl$_2$/n-hexane). $^1$H NMR (CDCl$_3$) δ 2.04 (quin, J=7.0 Hz, 4 H, 2×CH$_2$CH$_2$CH$_2$), 2.39 (s, 3 H, NCH$_3$), 2.73 (t, J=7.2 Hz, 4 H, CH2N(CH$_3$)CH$_2$), 3.74 (q, J=6.3 Hz, 4 H, 2×CH$_2$NH), 7.56 (dd, J=9.2, 2.4 Hz, 2 H, H-7), 7.92 (dd, J=8.7, 7.2 Hz, 2 H, H-3), 7.98 (d, J=9.2, 2 H, H-6), 8.03

(d, J=2.2 Hz, 2 H, H-9), 8.26 (dd, J=8.7, 1.5 Hz, 2 H, H-4), 8.92 (dd, J=7.2, 1.5 Hz, 2 H, H-2) and 10.64 (br t, J=5.2 Hz, 2 H, 2×CONH); HRMS (FAB$^+$) m/z calcd for $C_{33}H_{30}{}^{35}Cl_2N_7O_2$ 626.1838 (MH$^+$), found 626.1860. Anal. ($C_{33}H_{30}Cl_2N_7O_2$) C, H, N, Cl.

EXAMPLE 65

Preparation of Compound 65 of Table I

Reaction of 2-bromo-3-nitrobenzoic acid and 2,5-xylidine gave 2-(2,5-dimethyl phenylamino)-3-nitro benzoic acid (65%): mp (benzene/acetone) 215–217° C. $^1$H NMR [(CD$_3$)$_2$SO] δ 2.10 (s, 3 H, CH$_3$), 2.23 (s, 3 H, CH$_3$), 6.53 (s, 1H, H-6'), 6.79 (d, J=7.4 Hz, 1 H, H-4'), 7.02 (t, J=8.0 Hz, 1 H, H-5), 7.11 (d, J=7.7 Hz, 1 H, H-3'), 8.03 (dd, J=8.1, 1.4 Hz, 1 H, H-6), 8.22 (dd, J=7.7, 1.5 Hz, 1 H, H-4), 9.84 (br s, 1 H, NH), 13.8 (br s, 1 H, CO$_2$H). Anal. ($C_{15}H_{14}N_2O_4$) C, H, N.

Reductive ring closure of the above acid with NaOC$_2$H$_5$/NaBH$_4$ gave 6,9-dimethyl phenazine-1-carboxylic acid (64%), mp (MeOH) 246–247° C. $^1$H NMR [(CD$_3$)$_2$SO] δ 2.78 (s, 3 H, CH$_3$), 2.83 (s, 3 H, CH$_3$), 7.80 (d, J=7.0 Hz, 1 H, H-7 or H-8), 7.84 (s, d, J=7.0 Hz, 1 H, H-7 or H-8), 8.12 (dd, J=8.5, 7.2 Hz, 1 H, H-3), 8.56 (d, J=8.7 Hz, 1 H, H-4), 8.66,(d, J=7.0 Hz, 1 H, H-2), 15.24 (br s, 1H, CO$_2$H). Anal. ($C_{15}H_{12}N_2O_2$). C, H, N.

Activation and coupling of the above acid gave bis[3-(6, 9-dimethylphenazine-1-carboxamido) propyl]methylamine (65) as a bright yellow solid (53%), mp 97–101° C. (CH$_2$Cl$_2$/n-hexane). $^1$H NMR (CDCl$_3$) δ 2.02 (m, 4 H, 2×CH$_2$CH$_2$CH$_2$), 2.34 (s, 3 H, NCH$_3$), 2.60–2.68 (br m, 4 H, CH$_2$N(CH$_3$)CH$_2$), 2.68 (s, 6 H, 2×ArCH$_3$), 2.78 (s, 6 H, 2×ArCH$_3$), 3.70 (q, J=6.6 Hz, 4 H, 2×CH$_2$NH), 7.32–7.40 (m, 4 H, H-7 and H-8), 7.86 (dd, J=8.6, 7.2 Hz, 2 H, H-3), 8.28 (dd, J=8.7, 1.5 Hz, 2 H, H-4), 8.90 (dd, J=7.1, 1.5 Hz, 2 H, H-2) and 11.00 (br s, 2 H, 2×CONH); HRMS (FAB$^+$) m/z calcd for $C_{37}H_{40}N_7O_2$ 614.3243 (MH$^+$), found 614.3237. Anal. ($C_{37}H_{40}N_7O_2.0.5H_2O$) C, H, N.

EXAMPLE 66

Preparation of Compound 66 of Table 1

A mixture of 5-chloro-2-methylaniline (8.63 g, 61.0 mmol), 2-bromo-3-nitrobenzoic acid (10.0 g, 41.0 mmol), CuCl (0.5 g), copper powder (0.1 g) in butane-2,3-diol (25 mL) and N-ethylmorpholine (15 mL) was stirred and heated for 18 h. at 70° C. The reaction mixture was diluted with 0.5 M NH$_4$OH (500 mL), then filtered through Celite. The orange filtrate was then slowly added to a stirred solution of 2 N HCl and the resulting yellow precipitate was collected by filtration, dried and recrystallized to give 2-[(5-chloro-2-methyl)phenylamino]-3-benzoic acid as a bright yellow crystalline solid (70%), mp 228–230° C. (EtOAc/n-hexane). $^1$H NMR (CDCl$_3$) δ 2.35 (s, 3 H, CH$_3$), 6.79 (d, J=2.1 Hz, 1 H, H-6'), 6.96–7.00 (m, 2 H, H-4' and H-5'), 7.15 (d, J=8.0 Hz, 1 H, H-3'), 8.07 (dd, J=8.1, 1.8 Hz, 1 H, H-4 or H-6), 8.24 (dd, J=7.9, 1.7 Hz, 1 H, H-6 or H-4) and 9.51 (s, 1 H, COOH). Anal. ($C_{14}H_{11}ClN_2O_4$) C, H, N.

A solution of 2-[(5-chloro-2-methyl)phenylamino]-3-benzoic acid (3.59 g, 11.7 mmol) and NaBH$_4$ (2.62 g, 68.8 mmol) in 2 M NaOH was heated at reflux for 8 h. The reaction mixture was then cooled and acidified with AcOH to precipitate the crude phenazine acid. This solid was collected and recrystallized to give 6-chloro-9-methylphenazine-1-carboxylic acid as mustard-yellow needles (45%), mp 255–257° C. (acetone). $^1$H NMR [(CD$_3$)$_2$SO] δ 2.86 (s, 3 H, CH$_3$), 7.90 (dd, J=7.4, 1.1 Hz, 2 H, ArH), 8.11–8.18 (m, 2 H, ArH), 8.57–8.61 (m, 2 H, ArH) and 14.52 (br s, 1 H, COOH). Anal. ($C_{14}H_9ClN_2O_2$) C, H, N, Cl.

The above 6-chloro-9-methylphenazine-1-carboxylic acid was activated and coupled to give bis[(6-chloro-9-methylphenazine-1-carboxamido)propyl]methylamine (66) as a green-yellow solid (84%), mp 200–202° C. (CH$_2$Cl$_2$/n-hexane). $^1$H NMR (CDCl$_3$) δ 1.97 (quin, J=7.2 Hz, 4 H, 2×CH$_2$CH$_2$CH$_2$), 2.31 (s, 3 H, NCH$_3$), 2.59 (t, J=7.1 Hz, 4 H, CH$_2$N(CH$_3$)CH$_2$), 2.76 (s, 6 H, 2×ArCH$_3$), 3.69 (q, J=6.7 Hz, 4 H, 2×CH$_2$NH), 7.50 (dd, J=7.6, 1.0 Hz, 2 H, H-8), 7.78 (d, J=7.5 Hz, 2 H, H-7), 7.93 (dd, J=8.7, 7.2 Hz, 2 H, H-3), 8.41 (dd, J=8.7, 1.5 Hz, 2 H, H-2), 8.94 (dd, J=7.1, 1.5 Hz, 2 H, H-4), and 10.72 (br s, 2 H, 2×CONH); HRMS (FAB$^+$) m/z calcd for $C_{35}H_{34}{}^{35}Cl_2N_7O_2$ 654.2151 (MH$^+$), found 654.2159. Anal. ($C_{31}H_{34}Cl_2N_7O_2.0.5H_2O$) C, H, N.)

EXAMPLE 67

Preparation of Compound 67 of Table 1

Activation and coupling of the known [Rewcastle et al. *J. Med. Chem.* 1987, 30, 843] 4-methylphenazine-1-carboxylic acid gave bis[(4-methylphenazine-1-carboxamido)propyl] methylamine (67) as a bright yellow solid, (78%), mp 218–220° C. (CH$_2$Cl$_2$/n-hexane). $^1$H NMR (CDCl$_3$) δ 2.04 (quin, J=7.0 Hz, 2 H, 2×CH$_2$CH$_2$CH$_2$), 2.38 (s, 3 H, NCH$_3$), 2.75 (t, J=7.3 Hz, 4 H, CH$_2$N(CH$_3$)CH$_2$), 2.90 (s, 6 H, 2×CH$_3$)$_1$ 3.71 (q, J=6.3 Hz, 4 H, 2×CH$_2$NH), 7.58 (ddd, J=8.6, 6.7, 1.3 Hz, 2 H, ArH), 7.65 (ddd, J=8.6, 6.6, 1.4 Hz, 2 H, ArH), 7.70 (dd, J=7.2, 1.0 Hz, 2 H, ArH), 7.94 (dd, J=8.6, 0.9 Hz, 2 H, ArH), 8.00 (d, J=8.7 Hz, 2 H, ArH), 8.77 (d, J=7.3 Hz, 2 H, ArH) and 10.88 (br s, 2 H, 2×CONH). HRMS (FAB$^+$) m/z calcd for $C_{35}H_{36}N_7O_2$ 586.2930 (MH$^+$), found 586.2922. Anal. ($C_{35}H_{36}N_7O_2.2.5H_2O$) C, H, N.

EXAMPLE 68

Preparation of Compound 68 of Table 1

Activation of 9-methylphenazine-1-carboxylic acid and coupling with N,N'-bis(3-aminopropyl)ethylenediamine gave bis[3-(-9-methylphenazine-1-carboxamido)propyl]-1, 2-ethylenediamine (68) as a gum, which was converted to the dihydrochloride salt (10%), mp (MeOH) 276° C. $^1$H NMR (D$_2$O) δ 2.07 (quin, J=6.7 Hz, 4 H, 2×CH$_2$), 2.82 (s, 6 H, 2×ArCH$_3$), 3.17 (m, 4 H, 2×CH$_2$), 3.31 (br s, 4 H, 2×CH$_2$), 3.65 (t, J=6.6 Hz, 4 H, 2×CH$_2$), 7.87 (m, 4 H, 4×ArH), 7.96–8.00 (m, 4 H, 4×ArH), 8.27–8.30 (m, 2 H, 2×ArH), 8.60 (d, J=7.2 Hz, 2 H, 2×ArH). HRMS (FAB); Calculated for $C_{36}H_{38}N_8O_2$: 615.3196 Found: 615.3196.

EXAMPLE 69

Preparation of Compound 69 of Table 1

Activation of 6,9-dimethylphenazine-1-carboxylic acid and coupling with triethylenetetramine gave bis[2-(6-9-dimethylphenazine-1-carboxamido)ethyl]-1,2-ethylenediamine (69) (99%), mp (dihydrochloride salt from MeOH) 299° C. (dec.). $^1$H NMR (CF$_3$CO$_2$D) δ 3.06 (s, 6 H, 2×CH$_3$), 3.09 (s, 6 H, 2×CH$_3$), 3.87 (br s, 4 H, 2×CH$_2$), 3.91 (br s, 4 H, 2×CH$_2$), 4.27 (br s, 4 H, 2×CH$_2$), 8.20 (d, J=7.3 Hz, 2 H, H-7 or H-8), 8.24 (d, J=7.3 Hz, 2 H, H-7 or H-8), 8.43 (t, J=8.1 Hz, 2 H, H-3), 8.96 (d, J=8.8 Hz, 2 H, H-4), 9.02 (d, J=7.3 Hz, 2 H, H-2). Anal. ($C_{36}H_{40}Cl_2N_8O_2$) C, H, N.

EXAMPLE 70

Preparation of Compound 70 of Table 1

Activation of 9-methylphenazine-1-carboxylic acid and coupling with N,N'-bis(3-aminopropyl)butanediamine gave bis[2-(-9-methylphenazine-1-carboxamido)propyl]-1,4-butanediamine (70) (73%), mp (CH$_2$Cl$_2$/hexane) 86–90.5° C. $^1$H NMR (CDCl$_3$) δ 1.53 (quin, J=3.2 Hz, 4 H, 2×CH$_2$), 1.97 (quin, J=7.0 Hz, 4 H, CH$_2$), 2.62 (t, J=6.2 Hz, 4 H, 2×CH$_2$), 2.79 (t, J=7.0 Hz, 4 H, 2×CH$_2$), 2.88 (s, 6 H, 2×CH$_3$), 3.74 (q, J=6.6 Hz, 4 H, 2×CH$_2$), 7.71–7.78 (m, 4 H, ArH), 7.93 (dd, J=8.7, 7.2 Hz, 2 H, H-3), 8.08 (d, J=7.9, 0.8 Hz, 2 H, ArH), 8.34 (dd, J=8.7, 1.5 Hz, 2 H, H-4), 8.96 (dd, J=7.1, 1.5 Hz, 2 H, H-2), 11.05 (t, J=5.2 Hz, 2 H, 2×CONH). Anal. (C$_{38}$H$_{42}$N$_8$O$_2$·1.5H$_2$O) C, H, N.

EXAMPLE 71

Preparation of Compound 71 of Table 1

Activation of 5-methylacridine-4-carboxylic acid and coupling with triethylenetetramine gave bis[3-(5-methyl-acridine-4-carboxamido)ethyl]-1,2-ethylenediamine (71) (76%), mp (CH$_2$Cl$_2$/hexane) 167–170° C. $^1$H NMR (CDCl$_3$) δ 2.08 (s, 6 H, 2×CH$_3$), 2.85 (s, 4 H, 2×CH$_2$), 2.99 (t, J=6.2 Hz, 4 H, 2×CH$_2$), 3.74 (q, J=6.1 Hz, 4 H, 2×CH$_2$), 7.39 (dd, J=8.4, 6.8 Hz, 2 H, H-2), 7.57–7.61 (m, 4 H, H-6 & H-7), 7.75 (d, J=8.7 Hz, 2 H, H-8), 8.02 (dd, J=8.4, 1.5 Hz, 2 H, H-1), 8.68 (s, 2 H, H-9), 8.91 (dd, J=7.2, 1.5 Hz, 2 H, H-3), 11.81 (t, J=5.5 Hz, 2 H, 2×CONH). Anal. (C$_{36}$H$_{36}$N$_6$O$_2$) C, H, N.

EXAMPLE 72

Preparation of Compound 72 of Table 1

Activation of acridine-4-carboxylic acid and coupling with triethylenetetramine gave bis[3-(acridine-4-carboxamido)ethyl]-1,2-ethylenediamine (72) (72%), mp (CH$_2$Cl$_2$/hexane) 170–171° C. $^1$H NMR (CDCl$_3$) δ 2.91 (s, 8 H, 4×CH$_2$), 3.53 (q, J=5.4 Hz, 4 H, 2×CH$_2$), 7.53 (t, J=7.4 Hz, 2 H, ArH), 7.68 (dd, J=8.3, 7.1 Hz, 2 H, ArH), 7.81–7.85 (m, 2 H, ArH), 8.03 (d, J=8.3 Hz, 2 H, ArH), 8.22 (d, J=8.9 Hz, 2 H, ArH), 8.26 (dd, J=8.5, 1.4 Hz, 2 H, ArH), 8.64 (dd, J=7.1, 1.6 Hz, 2 H, H-3), 9.87 (s, 2 H, H-9), 11.56 (t, J=5.0 Hz, 2 H, 2×CONH). Anal (C$_{34}$H$_{32}$N$_6$O$_2$·2H$_2$O) C, H, N.

EXAMPLE 73

Preparation of Compound 73 of Table 1

Activation of the known [Rewcastle et al. *J. Med. Chem.* 1987, 30, 843] 9-methylphenazine-1-carboxylic acid and subsequent coupling with N,N'-bis(2-aminoethyl)-1,3-propanediamine gave bis[(9-methylphenazine-1-carboxamido)ethyl]-1,3-propanediamine (73) as a yellow solid (68%), mp 194–195° C. (CH$_2$Cl$_2$/n-hexane). $^1$H NMR (CDCl$_3$) δ 1.73 (quin, J=6.9 Hz, 2 H, CH$_2$CH$_2$CH$_2$), 2.79 (t, J=6.9 Hz, 4 H, 2×CH$_2$), 2.88 (s, 6 H, 2×ArCH$_3$), 2.97 (t, J=6.2 Hz, 4 H, 2×CH$_2$), 3.75 (q, J=6.0 Hz, 4 H, 2×CH$_2$), 7.64–7.69 (m, 2 H, ArH), 7.72 (dd, J=8.6, 6.8 Hz, 2 H, ArH), 7.93 (dd, J=8.7, 7.2 Hz, 2 H, ArH), 8.04 (dd, J=8.7, 0.9 Hz, 2 H, ArH), 8.33 (dd, J=8.7, 1.5 Hz, 2 H, ArH), 8.96 (dd, J=7.2, 1.5 Hz, 2 H, ArH) and 11.06 (br t, J=5.3 Hz, 2 H, 2×CONH); HRMS (FAB$^+$) m/z calcd for C$_{35}$H$_{37}$N$_8$O$_2$ 601.3039 (MH$^+$), found 601.3043. Anal. (C$_{35}$H$_{36}$N$_8$O$_2$·0.5H$_2$O) C, H, N.

EXAMPLE 74

Preparation of Compound 74 of Table 1

Activation of 6-chloro-9-methylphenazine-1-carboxylic acid as above, and subsequent coupling with triethylenetetramine gave bis[2-(6-chloro-9-methylphenazine-1-carboxamido)ethyl]-1,2-ethylenediamine (74) as a yellow solid, 6%, mp 301° C. (dec.) (HCl salt) (MeOH/EtOAc). $^1$H NMR (CF$_3$CO$_2$D) δ 3.87 (br s, 4 H, 2×CH$_2$NH), 4.04 (br s, 4 H, 2×CH$_2$NH), 4.09 (s, 6 H, 2×CH$_3$), 4.29 (br s, 4 H, 2×CONHCH$_2$), 8.25 (br d, J=7.9 Hz, 2 H. ArH), 8.44 (br d, J=7.7 Hz, 2 H, ArH), 8.53 (br s, 2 H, ArH), 9.03 (br d, J=8.7 Hz, 2 H, ArH) and 9.09 (br s, 2 H. ArH); HRMS (FAB$^+$) m/z calcd for C$_{34}$H$_{33}$$^{35}$Cl$_2$N$_8$O$_2$ 655.2104 (MH$^+$), found 655.2075.

EXAMPLE 74a

Preparation of Compound 74a of Table 1

N,N'-Dimethyl-N,N'-bis(cyanomethyl)ethylenediamine was synthesized by a reported method [Alcock et al., J. Chem Soc. Dalton Trans. 1987, 2643]. This compound (5.0 g, 100 mmol) was then hydrogenated over Raney nickel in absolute EtOH saturated with dry ammonia for 5 days at 20° C. (additional Raney nickel was added as required). The catalyst was removed by filtration through a pad of Celite, and evaporation of solvents gave essentially pure N,N'-dimethyl-N,N'-bis(2-aminoethyl)ethylenediamine (4.6 g, 88%). $^1$H NMR (CDCl$_3$) δ 2.24 (s, 6 H, 2×CH$_3$), 2.43 (br s, 4 H, 2×CH$_2$), 2.49 (s, 2 H, 2×CH$_2$) 2.73 (br s, 2 H, 2×CH$_2$), that was used directly. 9-Methyl phenazine-1-carboxylic acid (1.0 g, 4.2 mmol), and CDI (1.36 g, 8.4 mmol) in DMF (10 mL) was stirred at 50–60° C. for 1 h, then cooled to 20° C. Dry benzene (20 mL) and Sephadex LH-20 (2 g) was added, and the mixture was stirred at 20° C. for 1 h, then filtered through a pad of Celite to remove the Sephadex. The filtrate was evaporated to dryness under reduced pressure, and the residue was dissolved in dry THF (15 mL) and cooled in ice/salt. N,N'-Dimethyl-N,N' bis(2-aminoethyl) ethylenediamine (0.36 g, 2.1 mmol) was added, and the mixture was stirred while allowing it to warm to 20° C. Water (50 mL) was added, and and the THF was evaporated evaporated under reduced pressure. The resulting precipitate was filtered and washed with aq Na$_2$CO$_3$ (3×50 mL) and water, then dissolved in CH$_2$Cl$_2$ (100 mL) and dried (Na$_2$SO$_4$). Evaporation of solvents gave a crude product that was chromatographed on silica gel, eluting with a gradient of 1–6% MeOH in CH$_2$Cl$_2$) to give 74a as an oil (1.1 g, 78%). $^1$H NMR (CDCl$_3$) _ 2.33 (s, 6 H, 2×NCH$_3$), 2.63 (br s, 4 H, CH$_3$NCH$_2$ CH$_2$NCH$_3$), 2.74 (t, J=6.5 Hz, 4 H, CONHCH$_2$CH$_2$), 2.83 (s, 6 H, 2×ArCH$_3$), 3.73 (q, J=6.2 Hz, 4 H, 2×CONHCH$_2$), 7.61 (d, J=6.7 Hz, 2 H, H-8), 7.68 (dd, J=8.7, 6.8 Hz, 2 H, H-7), 7.89 (dd, J=8.7, 7.2 Hz, 2 H, H-3), 7.98 (d, J=8.7 Hz, 2 H, H-6), 8.26 (dd, J=8., 1.5 Hz, 2 H, H-4), 8.89 (dd, J=7.0, 1.5 Hz, 2 H, H-2), 10.85 (t, J=5.2 Hz, 2 H, 2×CONH).

EXAMPLE 75

Preparation of Compound 75 of Table 1

N-(tert-butoxycarbonyl)-3,3'-diamino-N-methyldipropylamine was prepared as reported [Huang, T. L., Dredar, S. A., Manneh, V. A., Blankenship, J. W., Fries, D. S., J. Med. Chem., 1992, 35, 2414–24181. A solution of di-tert-butyldicarbonate (2.51 g, 11.5 mmol) in THF (15 mL) was added, over the course of 1.5 h., to a solution of 3,3'-diamino-N-methyldipropylamine (5.00 g, 34.4 mmol) in THF (15 mL), which was maintained at 0° C. (ice/water). The reaction mixture was stirred for a further 18 h at room temperature, then the solvent removed under reduced pressure and the resulting residue partitioned between NaCl (sat.) (100 mL) and CH$_2$Cl$_2$ (200 mL). The CH$_2$Cl$_2$ layer was washed with a further portion of NaCl solution (100 mL), then dried (Na$_2$SO$_4$), and the solvent removed under reduced pressure to give N-(tert-butoxycarbonyl)-3,3'-diamino-N-methyldipropylamine (2.58 g, 46%) as a clear, viscous oil. $^1$H NMR (CDCl$_3$) δ 1.44 [br s, 9 H, C(CH$_3$)$_3$], 1.58–1.67 (m, 6 H, 2×CH$_2$CH$_2$CH$_2$ and NH$_2$), 2.22 (s, 3 H, NCH$_3$), 2.34–2.40 (m, 4 H, 2×CH$_2$NCH$_3$), 2.74 (t, J=6.9 Hz, 2 H, CH$_2$NH$_2$), 3.12–3.21 (br m, 2 H, CH$_2$NHBOC) and 5.37 (br s, 1 H, NHBOC).

Phenazine-1-carboxylic acid (494 mg, 2.24 mmol) was prepared according to the literature method [Rewcastle, G. W., Denny, W. A., Baguley, B. C., J. Med. Chem., 1987, 30, 843–857], and subsequently reacted with CDI (544 mg, 3.36 mmol) in dry DMF (15 mL) for 2.5 h. at 30° C. The DMF was removed under reduced pressure and the resulting yellow solid was dissolved in a mixture of petroleum ether and CH$_2$Cl$_2$ (40 mL, 3:1). Upon cooling, the imidazolide crystallized out and this crude material was used in the following coupling reaction. The crude imidazolide was suspended in THF (20 mL), cooled to 0° C. (ice/water), then a THF (20 mL) solution of the above N-(tert-butoxycarbonyl)-3,3'-diamino-N-methyldipropylamine (659 mg, 2.69 mmol) was added. The reaction mixture was allowed to stir for a further 2 h. at 0° C., then the solvent removed under reduced pressure and the resulting yellow oil partitioned between CH$_2$Cl$_2$ (200 mL) and 1 M (Na$_2$CO$_3$) (200 mL). The CH$_2$Cl$_2$ layer was dried with Na$_2$SO$_4$, the solvent removed under reduced pressure, and the resulting yellow-green oil was purified by chromatography on alumina (0.25% MeOH in CH$_2$Cl$_2$) to give N-1-(3-{N-methyl-N-[N-(tert-butoxycarbonyl)- 3-aminopropyl]}aminopropyl) phenazine-1-carboxamide (992 mg, 98%) as a yellow-green oil, which was used directly. $^1$H NMR (CDCl$_3$) δ 1.41 (br s, 9 H, C(CH$_3$)$_3$), 1.44 (br s, 2 H, CH$_2$CH$_2$CH$_2$NHBOC), 1.95–2.04 (m, 2 H, CH$_2$CH$_2$CH$_2$NHCOAr), 2.18 (s, 3 H, NCH$_3$), 2.46 (t, J=6.7 Hz, 2 H, CH$_2$CH$_2$CH$_2$NHBOC), 2.56 (t, J=7.2 Hz, 2 H, CH$_2$CH$_2$CH$_2$NHCOAr), 3.20 (m, 2 H, CH$_2$NHBOC), 3.74 (q, J=6.2 Hz, 2 H, CH$_2$NHCOAr), 5.45 (br s, 1 H, NHBOC), 7.89–8.00 (m, 3 H, ArH), 8.22–8.26 (m, 1 H, ArH), 8.28–8.32 (m, 1 H, ArH), 8.40 (dd, J=8.7, 1.5 Hz, 1 H, ArH), 9.02 (dd, J=7.1, 1.5 Hz, 1 H, ArH) and 11.03 (br s, 1 H, CONH).

To a solution of the above BOC-protected amine (545 mg, 1.21 mmol) in CH$_2$Cl$_2$ (8 mL), was added trifluoroacetic acid (8 mL). This mixture was stirred at room temperature for 2 h. at which point the reaction was complete by TLC. All solvents were removed under reduced pressure and the oily residue partitioned between CH$_2$Cl$_2$ (100 mL) and 1 M (Na$_2$CO$_3$) (100 mL). The aqueous layer was extracted with additional CH$_2$Cl$_2$ (4×100 mL) and all CH$_2$Cl$_2$ extracts were combined and dried with Na$_2$SO$_4$. The solvent was removed under reduced pressure to give N-1-{3-[N-methyl-N-(3-aminopropyl)]aminopropyl}phenazine-1-carboxamide (392 mg, 92%) as a green-yellow oil, which was used directly. $^1$H NMR (CDCl$_3$) δ 1.61–1.67 (m, 4 H, CH$_2$CH$_2$CH$_2$NH$_2$), 2.00 (quin, J=7.1 Hz, 2 H, CH$_2$CH$_2$CH$_2$NHCOAr), 2.29 (s, 3 H, NCH$_3$), 2.46 (t, J=7.2 Hz, 2 H, CH$_2$CH$_2$CH$_2$NH$_2$), 2.59 (t, J=7.2 Hz, 2 H, CH$_2$CH$_2$CH$_2$NHCOAr), 2.75 (t, J=6.8 Hz, 2 H, CH$_2$NH$_2$), 3.72 (q, J=6.5 Hz, 2 H, CH$_2$NHCOAr), 7.89–7.99 (m, 3 H, ArH), 8.22–8.25 (m, 1 H, ArH), 8.28–8.32 (m, 1 H, ArH), 8.40 (dd, J=8.6, 1.5 Hz, 1 H, ArH), 9.01 (dd, J=7.1, 1.5 Hz, 1 H, ArH) and 11.01 (br s, 1 H, CONH).

The known [Atwell, G. J., Rewcastle, G. W., Baguley, B. C., Denny, W. A., J. Med. Chem., 1987, 30, 664–669] acridine-4-carboxylic acid (274 mg, 1.23 mmol) was reacted with CDI (300 mg, 1.85 mmol) to form the imidazolide which was isolated as above. The imidazolide was suspended in THF (15 mL), the suspension cooled to 0° C. (ice/water), then a solution of the above amine (392 mg, 1.12 mmol) in THF (10 mL) slowly added. The reaction mixture was stirred for 2 h at 0° C., then 18 h. at room temperature. The solvent was removed under reduced pressure and the residue was partitioned between CH$_2$Cl$_2$ (100 mL) and 1 M (Na$_2$CO$_3$) (100 mL). The CH$_2$Cl$_2$ layer was dried with Na$_2$SO$_4$, the solvent removed under reduced pressure to give an orange solid which was purified by chromatography on alumina (0.5% MeOH in CH$_2$Cl$_2$ as eluant) and silica (1% MeOH and 0.25% triethylamine in CH$_2$Cl$_2$ as eluant) to give N-1-{3-[{3-[(acridinyl-4-carbonyl)amino]propyl}(methyl) amino]propyl}phenazine-1-carboxamide (75) (as a pale yellow solid; mp 171–173° C. (CH$_2$Cl$_2$/n-hexane), $^1$H NMR (CDCl$_3$) δ 1.88 (quin, J=5.6 Hz, 2 H, CH$_2$CH$_2$CH$_2$), 2.02 (quin, J=6.0 Hz, CH$_2$CH$_2$CH$_2$), 2.38 (s, 3 H, NCH$_3$), 2.65–2.70 (m, 4 H, 2×CH$_2$NCH$_3$), 3.62–3.68 (m, 2 H, CH$_2$NHCO), 3.76 (q, J=6.5 Hz, 2 H, CH$_2$NHCO), 7.11 (t, J=7.7 Hz, 1 H, ArH), 7.22–7.29 (m, 1 H, ArH), 7.36 (d, J=8.3 Hz, 1 H, ArH), 7.65 (ddd, J=8.3, 6.9, 1.5 Hz, 1 H, ArH), 7.85–7.93 (m, 3 H, ArH), 8.00 (dd, J=7.5, 0.9 Hz, 1 H, ArH), 8.09–8.13 (m, 1 H, ArH), 8.23–8.27 (m, 1 H, ArH), 8.36 (dd, J=8.6, 1.5 Hz, 1 H, ArH), 8.42 (d, J=8.1 Hz, 1 H, ArH), 8.53 (dd, J=8.0, 1.2 Hz, 1 H, ArH), 8.88 (dd, J=7.2, 1.5 Hz, 1 H, ArH), 9.15 (s, 1 H, H-9), 11.03 [br s, 1 H, NH (phenazine)] and 12.55 [br s, 1 H, NH (acridine)]). Anal. (C$_{34}$H$_{32}$N$_6$O$_2$.2H$_2$O) C, H, N.

EXAMPLE 76

Preparation of Compound 76 of Table 1 by the Method of Scheme 3

Activation and coupling of 9-methylphenazine-1-carboxylic acid [Rewcastle, G. W., Denny, W. A., Baguley, B. C., J. Med. Chem., 1987, 30, 843–857] with N-(tert-butoxycarbonyl)-3,3'-diamino-N-methyldipropylamine as in Example 75 gave N-1-(3-{(N-methyl-N-[N-(tert-butoxycarbonyl)-3-aminopropyl]}aminopropyl)-9-methylphenazine-1-carboxamide as a yellow-green oil (89%), which was used directly. $^1$H NMR (CDCl$_3$) δ 1.41 (br s, 9 H, C(CH$_3$)$_3$), 1.65 (quin, J=6.6 Hz, 2 H, CH$_2$CH$_2$CH$_2$NHBOC), 1.98 (quin, J=7.2 Hz, 2 H, CH$_2$CH$_2$CH$_2$NHCOAr) 2.24 (s, 3 H, NCH$_3$), 2.42 (t, J=6.7 Hz, 2 H, CH$_2$CH$_2$CH$_2$NHBOC), 2.53 (t, J=7.3 Hz, 2 H, CH$_2$CH$_2$CH$_2$NHCOAr) 2.94 (s, 3 H, ArCH$_3$), 3.12–3.23 (br s, 2 H, CH$_2$NHBOC), 3.73 (q, J=6.7 Hz, 2 H, CH$_2$NHCOAr), 5.39 (br s, 1 H, NHBOC), 7.77 (dt, J=6.5, 1.1 Hz, 1 H, ArH), 7.81 (dd, J=8.5, 6.8 Hz, 1 H, ArH), 7.97 (dd, J=8.7, 7.2 Hz, 1 H, ArH), 8.14 (d, J=8.4 Hz, 1 H, ArH), 8.39 (dd, J=8.6, 1.5 Hz, 1 H, ArH), 9.02 (dd, J=7.2, 1.5 Hz, 1 H, ArH) and 11.13 (br t, J=5.2 Hz, 1 H, CONH).

Deprotection of the above BOC-protected amine as in Example 75 gave N-{-3-[N-methyl-N-(3-aminopropyl)] aminopropyl}-9-methylphenazine-1-carboxamide as a green-yellow oil, (85%), which was used directly. $^1$H NMR (CDCl$_3$) δ 1.62 (quin, J=7.0 Hz, 2 H, CH$_2$CH$_2$CH$_2$NH$_2$), 1.98 (quin, J=7.3 Hz, 2 H, CH$_2$CH$_2$CH$_2$NHCOAr), 2.26 (s, 3 H, NCH$_3$), 2.43 (t, J=7.2 Hz, 2 H, CH$_2$CH$_2$CH$_2$NH$_2$), 2.53 (t, J=7.3 Hz, 2 H, CH$_2$CH$_2$CH$_2$NHCOAr), 2.75 (m, 2 H, CH$_2$NH$_2$), 2.93 (s, 3 H, ArCH$_3$), 3.73 (q, J=6.7 Hz, 2 H, CH$_2$NHCOAr), 7.76 (dt, J=6.7, 1.3 Hz, 1 H, ArH)N, 7.81 (dd, J=8.4, 6.9 Hz, 1 H, ArH), 7.97 (dd, J=8.6, 7.1 Hz, 1 H, ArH), 8.13 (dd, J=8.7, 1.0 Hz, 1 H, ArH), 8.38 (dd, J=8.7, 1.5 Hz, 1 H, ArH), 9.00 (dd, J=7.1, 1.5 Hz, 1 H, ArH) and 11.11 (br s, 1 H, CONH).

Activation and coupling of 5-methylacridine-4-carboxylic acid [Atwell, G. J., Rewcastle, G. W., Baguley, B.

C., Denny, W. A., J. Med. Chem., 1987, 30, 664–669] with the above deprotected amine as in Example 75 gave N-1-{3-[{3-[(5-methylacridinyl-4-carbonyl)amino]propyl}(methyl)amino]propyl}-9-methylphenazine-1-carboxamide (76) as a pale yellow solid (66%), mp 116–121° C. (CH$_2$Cl$_2$/n-hexane). $^1$H NMR (CDCl$_3$) δ 1.94–2.02 (m, 4 H, 2×CH$_2$CH$_2$CH$_2$), 2.32 (s, 3 H, NCH$_3$), 2.58–2.63 (m, 4 H, 2×CH$_2$NCH$_3$), 2.73 (s, 3 H, ArCH$_3$), 2.80 (s, 3 H, ArCH$_3$), 3.66–3.74 (m, 4 H, 2×CH$_2$NHCO), 7.31 (dd, J=8.4, 6.8 Hz, 1 H, ArH), 7.52 (m, 2 H, ArH), 7.59 (dd, J=8.2, 7.2 Hz, 1 H, ArH), 7.63–7.69 (m, 2 H, ArH), 7.90 (dd, J=8.7, 7.2 Hz, 1 H, ArH), 7.95–8.00 (m, 2 H, ArH), 8.28 (dd, J=8.7, 1.5 Hz, 1 H, ArH), 8.61 (s, 1 H, H-9), 8.90–8.95 (m, 2 H, ArH), 10.87 [br s, 1 H, NH (phenazine)] and 11.78 [br s, 1 H, NH (acridine)]. Analysis for N-1-{3-[{3-[(5-methylacridinyl-4-carbonyl)amino]propyl}(methyl)amino]propyl}-9-methylphenazine-1-carboxamide (76) Anal. (C$_{36}$H$_{36}$N$_6$O$_2$.H$_2$O) C, H, N.

EXAMPLE 77

Preparation of Compound 77 of Table 1 by the Method of Scheme 3

Activation and coupling of phenazine-1-carboxylic acid [Rewcastle, G. W., Denny, W. A., Baguley, B. C., J. Med. Chem., 1987, 30, 843–857] with N-1-{3-[N-methyl-N-(3-aminopropyl)]aminopropyl}-9-methylphenazine-1-carboxamide [see Example 76 for preparation] as above gave N-1-{3-[{3-[(phenazinyl-1-carbonyl)amino]propyl}(methyl)amino]-propyl}-9-methylphenazine-1-carboxamide (77) as a yellow solid, 77%, mp 120° C. (dec.) (CH$_2$Cl$_2$/n-hexane). $^1$H NMR (CDCl$_3$) δ 1.96–2.07 (m, 4 H, 2×CH$_2$CH$_2$CH$_2$), 2.36 (s, 3 H, NCH$_3$), 2.65–2.73 (m, 7 H, 2×CH$_2$NCH$_3$ and ArCH$_3$), 3.68–3.78 (m, 4 H, 2×CH$_2$NHCO), 7.47 (dt, J=6.9, 1.1 Hz, 1 H, ArH), 7.57 (ddd, J=8.7, 6.6, 1.2 Hz, 1 H, ArH), 7.63 (dd, J=8.7, 6.8 Hz, 1 H, ArH), 7.71 (ddd, J=8.7, 6.7, 1.5 Hz, 1 H, ArH), 7.87 (dd, J=8.7, 7.2 Hz, 1 H, ArH), 7.90 (dd, J=8.6, 7.1 Hz, 1 H, ArH), 7.94 (d, J=9.2 Hz, 1 H, ArH), 8.00 (d, J=8.6 Hz, 1 H, ArH), 8.08 (d, J=8.5 Hz, 1 H, ArH), 8.21 (dd, J=8.7, 1.5 Hz, 1 H, ArH), 8.31 (dd, J=8.7, 1.5 Hz, 1 H, ArH), 8.89 (dd, J=7.1, 1.5 Hz, 1 H, ArH), 8.92 (dd, J=7.2, 1.5 Hz, 1 H, ArH) and 10.87 (br s, 2 H, 2×NH). Analysis for N-1-{3-[{3-[(phenazinyl-1-carbonyl)amino]propyl}(methyl)amino]-propyl}-9-methylphenazine-1-carboxamide (77) Anal. (C$_{34}$H$_{33}$N$_7$O$_2$.H$_2$O) C, H, N.

EXAMPLE 78

Preparation of Compound 78 of Table 1 by the Method of Scheme 3

Triethylenetetramine was reacted with di-tert-butyldicarbonate according to the method of Blagbrough et al (Pharm. Sciences, 1997, in press; personal communication) to give, after purification by column chromatography (20% MeOH in CH$_2$Cl$_2$ as eluant), N-aminoethyl-N,N'-bis(tert-butoxycarbonyl)-N-[(N-tert-butoxycarbonyl)aminoethyl]ethylenediamine as a pale yellow viscous oil (59%). $^1$H NMR (CDCl$_3$) ? 1.39–1.50 [m, 29 H, 3×C(CH$_3$)$_3$, NH$_2$], 3.00–3.62 (m, 12 H, 6×CH$_2$), 4.45 (br s, 1 H, NHBOC).

5-Methylacridine-4-carboxylic acid (1.00 g, 4.23 mmol) was reacted with CDI (1.02 g, 6.33 mmol) to form the imidazolide as reported above. The imidazolide was suspended in THF (80 mL) at room temperature, and a solution of the above amine (2.04 g, 4.65 mmol) in THF (20 mL) slowly added. The reaction mixture was then stirred for 18 h. at 20° C. The THF was removed under reduced pressure and the resulting yellow solid was partitioned between CH$_2$Cl$_2$ (200 mL) and 1 M Na$_2$CO$_3$ (200 mL). The CH$_2$Cl$_2$ layer was dried with Na$_2$SO$_4$ and the solvent removed under reduced pressure to give a yellow oil which was purified by column chromatography on alumina (0.5% MeOH in CH$_2$Cl$_2$ as eluant) to give the triBOC analogue of N-1-[2-(N-{2-[N-(2-aminoethyl)]aminoethyl})aminoethyl]-5-methylacridine-4-carboxamide as a yellow foam (1.41 g, 51%). $^1$H NMR (CDCl$_3$) d 1.46 [m, 30 H, 3×C(CH$_3$)$_3$, ArCH$_3$], 3.13–3.65 (m, 12 H, 6×CH$_2$), 4.43 (br s, 1 H, NHBOC), 7.48–7.55 (m, 1 H, ArH), 7.64–7.74 (m, 2 H, ArH), 7.88–7.94 (m, 1 H, ArH), 8.12–8.19 (m, 1 H, ArH), 8.85–8.90 (m, 1 H, ArH), 8.93–9.00 (m, 1 H, ArH), 12.23 (br s, 1 H, NH).

Trifluoroacetic acid (10 mL) was added to a solution of the above tri-BOC amide (1.00 g, 1.52 mmol) in CH$_2$Cl$_2$ (10 mL). The mixture was stirred at 20° C. for 2 h, at which point the reaction was complete by TLC. All solvents were removed under reduced pressure and the oily residue was partitioned between CHCl$_3$ (100 mL) and saturated Na$_2$CO$_3$ (20 mL). The aqueous layer was further extracted with additional CHCl$_3$ (11×100 mL) and all CHCl$_3$ extracts were combined and dried with Na$_2$SO$_4$. The solvent was removed under reduced pressure to give N-1-[2-(N-{2-[N-(2-aminoethyl)]aminoethyl})aminoethyl]-5-methylacridine-4-carboxamide (533 mg, 98%) as a yellow oil. $^1$H NMR (CDCl$_3$) d 2.58–2.68 (m, 2 H, CH$_2$), 2.70–2.76 (m, 4 H, 2×CH$_2$), 2.82–2.86 (m, 2 H, CH$_2$), 2.93 (s, 3 H, ArCH$_3$), 3.03–3.07 (m, 2 H, CH$_2$), 3.82–3.88 (m, 2 H, CH$_2$), 7.49–7.55 (m, 1 H, ArH), 7.65–7.75 (m, 2 H, ArH), 7.89–7.94 (m, 1 H, ArH), 8.13–8.18 (m, 1 H, ArH), 8.88 (br d, J=5.3 Hz, 1 H, ArH), 8.98 (td, J=7.1, 1.5 Hz, 1 H, ArH), 12.04 (br s, 1 H, NH).

9-Methylphenazine-1-carboxylic acid (1.00 g, 4.20 mmol) was reacted with CDI (1.02 g, 6.30 mmol) to form the imidazolide which was isolated as above. This imidazolide was suspended in THF (20 mL), the suspension cooled to ) 0° C. (ice/water) then a solution of the above polyamine (529 mg, 1.48 mmol) in THF (20 mL) slowly added. The reaction mixture was stirred for 2 h. at 0° C., then 18 h. at room temperature. The solvent was removed under reduced pressure and the residue was partitioned between CH$_2$Cl$_2$ (100 mL) and 1 M Na$_2$CO$_3$ (100 mL). The CH$_2$Cl$_2$ layer was dried with Na$_2$SO$_4$ and the solvent removed under reduced pressure to give a yellow solid (553 mg, 61%) which was purified by column chromatography on alumina (2% MeOH in CH$_2$Cl$_2$ as eluant) to give N-1-(2-{[2-({2-[(5-methylacridinyl-4-carbonyl)amino]ethyl}amino)ethyl]amino}-ethyl)-9-methylphenazine-1-carboxamide (78) as a yellow solid. $^1$H NMR (CDCl$_3$) d 2.77 (s, 3 H, ArCH$_3$), 2.79 (s, 3 H, ArCH$_3$), 2.82–2.88 (m, 4 H, 2×CH$_2$), 2.97 (t, J=6.0 Hz, 2 H, CH$_2$), 3.02 (t, J=6.0 Hz, 2 H, CH$_2$), 3.70 (q, J=5.9 Hz, 2 H, CH$_2$), 3.79 (q, J=6.0 Hz, 2 H, CH$_2$), 7.31 (dd, J=8.4, 6.8 Hz, 1 H, ArH), 7.51–7.70 (m, 5 H ArH), 7.87 (dd, J=8.5, 7.1 Hz, 1 H, ArH), 7.91–7.96 (m, 2 H, ArH), 8.26 (dd, J=8.7, 1.5 Hz, 1 H, ArH), 8.57 [s, 1 H, H-9 (acridine)], 8.85–8.91 (m, 2 H, ArH), 10.83 [br t, J=5.1 Hz, 1 H, NH (phenazine)], 11.83 [br t, J=5.4 Hz, 1 H, NH (acridine)].

EXAMPLE 79

Preparation of Compound 79 of Table 1 by the Method of Scheme 3

Ethylenediamine was alkylated with an excess of chloroacetonitrile according to the method of Overman and Burk

[Bradshaw et al, Tetrahedron, 1992, 48, 4475], and the product was purified by filtration through a plug of flash silica (1% MEOH in $CH_2Cl_2$ as eluant) to give give N,N'-bis(cyanomethyl)ethylenediamine as a yellow oil which solidified upon cooling *88%), mp 41–42° C. $^1$H NMR ($CDCl_3$) d 1.58 (s, 2 H, 2×NH), 2.90 (s, 4 H, 2×$CH_2$), 3.63 (s, 4 H, 2×$CH_2$).

The above diamine (3.00 g, 21.7 mmol) in a mixture of THF (90 mL), water (10 mL) and triethylamine (10 mL) was treated with di-tert-butyldicarbonate (19.0 g, 87.0 mmol). All solvents were removed under reduced pressure and the resulting residue was partitioned between water (100 mL) and EtOAc (2×100 mL). The combined EtOAc layers were dried ($Na_2SO_4$), the solvent removed, and the resulting pale brown solid purified by flash chromatography on silica (50% EtOAc/PE as eluant) to give N,N'-bis(tert-butoxycarbonyl)-N,N'-bis(cyanomethyl)ethylenediamine as a white solid (6.59 g, 90%), mp 112–113° C. (EtOAc/peteroleum ether). $^1$H NMR ($CDCl_3$) d 1.50 [s, 18 H, 2×C($CH_3$)$_3$], 3.52 (s, 4 H, 2×$CH_2$), 4.13 (br s, 4 H, 2×$CH_2$).

Hydrogenation of the above with W-7 Raney nickel, according to a reported procedure [Ravikumar, Syn. Commun., 1994, 24, 1767] gave N,N'-bis(aminoethyl)-N,N'-bis(tert-butoxy carbonyl)ethylenediamine as a white solid (100%), mp 81–82° C. $^1$H NMR ($CDCl_3$) d 1.46 [s, 18 H, 2×C($CH_3$)$_3$], 1.57 (br s, 4 H, 2×$NH_2$), 2.83 (br s, 4 H, 2×$CH_2$), 3.30 (br m, 8 H, 4×$CH_2$).

The above diamine was reacted with ethyl trifluoroacetate according to the method of Blagbrough et al (Pharm. Sciences, 1997, in press; personal communication) to give N-aminoethyl-N,N'-bis(tert-butoxycarbonyl)-N'-[(N-trifluoroacetamido)aminoethyl]-ethylenediamine as a clear oil (39%). $^1$H NMR ($CDCl_3$) d 1.46 [s, 18 H, 2×C($CH_3$)$_3$], 1.95 (br s, 2 H, $NH_2$), 2.84–2.96 (m, 2 H, $CH_2$), 3.20–3.48 (m, 10 H, 5×$CH_2$), 7.99, 8.21, 8.51 (all br s, total 1 H, NH).

Phenazine-1-carboxylic acid (212 mg, 0.95 mmol) was reacted with CDI (230 mg, 1.42 mmol) to form the imidazolide, which was isolated as above. The imidazolide was then suspended in THF (10 mL) and a THF (10 mL) solution of the above monotrifluoroacetamide (416 mg, 0.95 mmol) slowly added to the solution. This mixture was allowed to stir at room temperature for 18 h., whereupon the solvent was removed under reduced pressure and the residue partitioned between $CH_2Cl_2$ (100 mL) and 1 M $Na_2CO_3$ (50 mL). The $CH_2Cl_2$ layer was then dried with $Na_2SO_4$ and the solvent removed under reduced pressure to give a residue that was purified by chromatography on alumina (0.5%. MeOH in $CH_2Cl_2$ as eluant) to give N-1-{2-[N'-tert-butoxycarbonyl-N'-(2-{N-tert-butoxycarbonyl-N-[2-(N-trifluoroacetamido)aminoethyl]aminoethyl})]-aminoethyl}phenazine-1-carboxamide as a yellow oil (558 mg, 91%). $^1$H NMR ($CDCl_3$) d 1.39 [br s, 9 H, C($CH_3$)$_3$] 1.43 [br s, 9 H, C($CH_3$)$_3$], 3.31–3.68 (m, 10 H, 5×$CH_2$), 3.82–3.89 (m, 2 H, $CH_2$), 7.90–8.44 [m, 7 H, 6×ArH, NHC(O)$CF_3$], 8.99 (br s, 1 H, ArH), 11.13 (br s, 1 H, CONH).

A solution of the above trifluoroacetamide (548 mg, 0.85 mmol) in a mixture of MeOH (30 mL) and $H_2O$ (20 mL) was treated with $K_2CO_3$ (584 mg, 4.23 mmol). This reaction was stirred and heated at reflux for 2 h., followed by room temperature for 18 h. Clean conversion of the trifluoroacetamide to the free amine was observed by TLC. The MeOH was removed under reduced pressure, then saturated $Na_2CO_3$ (20 mL) added to the residue and this aqueous portion extracted with $CHCl_3$ (2×50 mL). The combined $CHCl_3$ portions were dried with $Na_2SO_4$, then the solvent removed under reduced pressure to afford N-1-[2-(N'-tert-butoxycarbonyl-N'-{2-[N-(aminoethyl)-N-tert-butoxycarbonyl]-aminoethyl})aminoethyl]phenazine-1-carboxamide (470 mg, 100%) $^1$H NMR ($CDCl_3$) d 1.38 [br s, 9 H, C($CH_3$)$_3$], 1.43 [br s, 9 H, C($CH_3$)$_3$], 2.78 (t, J=6.5 Hz, 2 H, $NH_2$), 3.18–3.70 (m, 10 H, 5×$CH_2$), 3.81–3.90 (m, 2 H, $CH_2$), 7.89–8.00 (m, 3 H, ArH), 8.21–8.43 (m, 3 H, ArH), 9.00 (br s, 1 H, ArH), 11.08 (br s, 1 H, CONH).

Acridine-4-carboxylic acid (192 mg, 0.86 mmol) was reacted with CDI (210 mg, 1.29 mmol) to form the imidazolide which was isolated as above. The resulting imidazolide was then suspended in THF (20 mL) and a THF (10 mL) solution of the above amine (470 mg, 0.86 mmol) added slowly to the stirred solution. This mixture was allowed to stir at room temperature for 18 h., whereupon the solvent was removed under reduce pressure and the residue partitioned between $CH_2Cl_2$ (100 mL) and 1 M $Na_2CO_3$ (50 mL). The $CH_2Cl_2$ layer was dried with $Na_2SO_4$ and the solvent removed under reduced pressure to give a residue which was purified by column chromatography on alumina (0.5% MeOH in $CH_2Cl_2$ as eluant) to give N-1-(2-{[2-({2-[(acridinyl-4-carbonyl)amino]ethyl}N-tert-butoxycarbonyl amino)ethyl]N'-tert-butoxycarbonyl amino}ethyl) phenazine-1-carboxamide as a yellow oil (568 mg, 89%). $^1$H NMR ($CDCl_3$) d 1.42 [br s, 9 H, C($CH_3$)$_3$], 1.46 [br s, 9 H, C($CH_3$)$_3$], 3.37–3.69 (m, 10 H, 5×$CH_2$), 3.81–3.89 (m, 2 H, $CH_2$), 7.09–7.15 (m, 1 H, ArH), 7.25 (t, J=7.4 Hz, 1 H, ArH), 7.36 (d, J=8.3 Hz, 1 H, ArH), 7.64 (t, J=7.2 Hz, 1 H, ArH), 7.83–7.97 (m, 4 H, ArH), 8.11–8.27 (m, 3 H, ArH), 8.31–8.45 (m, 2 H, ArH), 8.53–8.61 (br s, 1 H, ArH), 8.89–8.99 (br s, 1 H, ArH), 11.10 [s, 1 H, CONH (phenazine)], 12.52 [s, 1 H, CONH (acridine)].

Gaseous HCl was bubbled through MeOH until the solution was strongly acidic to pH paper. The above protected amine was dissolved in this solution (20 mL) and stirred at room temperature for 18 h. The MeOH was removed under reduced pressure and the residue dissolved in saturated $Na_2CO_3$ (50 mL) which was then extracted with $CHCl_3$ (13×50 mL). The combined $CHCl_3$ extacts were dried with $Na_2SO_4$, then the solvent removed under reduced pressure to give N-1-(2-{[2-({2-[(acridinyl-4-carbonyl)amino]ethyl}amino)ethyl]amino}ethyl)phenazine-1-carboxamide (79) as a yellow solid (159 mg, 96%) mp 173–176° C. ($CH_2Cl_2$/MeOH). $^1$H NMR ($CDCl_3$) d 2.83–2.96 (m, 6 H, 3×$CH_2$), 3.07 (t, J=5.9 Hz, 2 H, $CH_2$), 3.46 (q, J=5.3 Hz, 2 H, $CH_2$), 3.80 (q, J=5.8 Hz, 2 H, $CH_2$), 7.01 (t, J=7.8 Hz, 1 H, ArH), 7.25 (ddd, J=8.1, 7.2, 0.9 Hz, 1 H, ArH), 7.32 (d, J=8.2 Hz, 1 H, ArH), 7.55 (br s, 1 H, ArH), 7.65 (ddd, J=8.3, 7.0, 1.5 Hz, 1 H, ArH), 7.79–7.90 (m, 4 H, ArH), 8.12–8.16 (m, 2 H, ArH), 8.26 (dd, J=8.7, 1.5 Hz, 1 H, ArH), 8.39 (dd, J=8.1, 1.3 Hz, 1 H, ArH), 8.43 (dd, J=8.1, 1.4 Hz, 1 H, ArH), 8.89 (dd, J=7.1, 1.5 Hz, 1 H, ArH), 11.11 [s, 1 H, CONH (phenazine)], 12.20 [s, 1 H, CONH (acridine)].

EXAMPLE 80

Biological Testing of Compounds of the Invention.
In vitro Testing

The in vitro cytotoxicity of the compounds of the present invention was evaluated by studies on murine P388 leukemia, the late-passage murine Lewis lung carcinoma line LLTC, and a wild-type human leukemia line (Jurkat; $JL_C$). Cells were grown as reported by Finlay et al. in Oncol. Res. 1994, 6, 33–37 and in Eur. J. Cancer 1996, 32A, 708–714, and growth inhibition assays were performed by culturing cells at 4×10$^3$ (P388), 10$^3$ (LLTC) and 3.75×10$^3$ (Jurkat lines) per well in microculture plates (150 µL per well) for 3 (P388) or 4 days in the presence of drug. Cell growth was determined by [$^3$H]TdR uptake (P388) as described by Marshall et al. in, *J. Natl. Cancer Inst.* 1992, 84, 340–345 or the sulforhodamine assay as described by Skehan et al. in, *J. Natl. Cancer Inst.* 1990, 82, 1107–1112. Independent assays were performed in duplicate, and coefficients of variation were 12% (P388), 12% (LLTC) and 6.3% ($JL_C$).

TABLE II

Biological activities of selected compounds of formula (I) listed in Table I.

| | IC$_{50}$ values (nM) | | |
|---|---|---|---|
| No | P388 | LLTC | JL$_c$ |
| 6 | | <6 | 11 |
| 7 | 170 | | |
| 8 | | 738 | 1540 |
| 9 | | 1086 | 2543 |
| 10 | 620 | 167 | 345 |
| 11 | | 32 | 87 |
| 12 | | 8 | 33 |
| 13 | 10 | 7 | 28 |
| 14 | 15 | 39 | 114 |
| 15 | 76 | 17 | 58 |
| 16 | 27 | 20 | 52 |
| 17 | 59 | 13 | 66 |
| 18 | 49 | 17 | 69 |
| 19 | | 165 | 380 |
| 20 | | 322 | 223 |
| 21 | 370 | 73 | 275 |
| 22 | 1370 | 795 | 1640 |
| 23 | 1500 | 2079 | 2079 |
| 24 | 1630 | 1620 | 1300 |
| 26 | | 20 | 147 |
| 27 | 138 | 36 | 99 |
| 28 | 190 | <24 | 137 |
| 29 | 220 | 36 | 226 |
| 31 | 1293 | 41 | 250 |
| 33 | 56 | 81 | 110 |
| 34 | 320 | 209 | 473 |
| 35 | 260 | 81 | 93 |
| 36 | 140 | 18 | 102 |
| 36 | 520 | 119 | 137 |
| 41 | | 151 | 209 |
| 42 | | 74 | 300 |
| 43 | 600 | 64 | 195 |
| 44 | | 83 | 274 |
| 45 | | 142 | 175 |
| 46 | | 24 | 30 |
| 47 | | 2.2 | 4.8 |
| 51 | 500 | 1310 | 1250 |
| 52 | | 120 | 172 |
| 53 | | 8.8 | 14 |
| 54 | 44 | 8.5 | 16 |
| 55 | 2130 | 671 | 1550 |
| 56 | 972 | 183 | 760 |
| 57 | 35 | 3.2 | 11 |
| 58 | * | 1.1 | 3.8 |
| 59 | 41 | 8.8 | 20.3 |
| 60 | * | 5.0 | 13 |
| 61 | 435 | 48 | 208 |
| 62 | 204 | 12 | 74 |
| 63 | 12,300 | 8370 | 2370 |
| 64 | 94 | 43.5 | 42.3 |
| 65 | 26 | 5.3 | 21.3 |
| 66 | 33 | 5.2 | 9.8 |
| 67 | * | 17 | 85 |
| 68 | * | 33.6 | 1.2 |
| 69 | * | 3.9 | 0.55 |
| 70 | * | 112 | 8.7 |
| 71 | 24 | 7.7 | 0.6 |
| 72 | 630 | >50 | 6.9 |
| 73 | <6.2 | 1.2 | 0.24 |
| 74 | 39 | 10.5 | 0.6 |

TABLE II-continued

Biological activities of selected compounds of formula (I) listed in Table I.

| | IC$_{50}$ values (nM) | | |
|---|---|---|---|
| No | P388 | LLTC | JL$_c$ |
| 75 | * | 78 | 272 |
| 76 | * | 1.8 | 8.8 |
| 77 | * | 19 | 31 |

In vivo testing

Selected compounds of general formula (I) also showed activity in vivo against sub-cutaneous colon 38 tumors in mice. These data are illustrated in the accompanying FIG. 1 for compounds 13 (at 60 mg/kg) and 17 (at 90 mg/kg). In this assay, colon 38 tumors were grown subcutaneously from 1 mm$^3$ fragments implanted sc in one flank of anaesthetised mice (pentobarbitone 90 mg/kg). Treatment began once they had reached a diameter of approximately 4 mm (normally after 7 days). Mice were divided into groups of 5 for control and drug treated groups, with average tumor volumes similar for each of the groups. Drugs were dissolved either in distilled water or 15% aqueous ethanol, and injected in a volume of 0.01 ml per gram of body weight in a split dose of two equal injections administered one hour apart. Mice were monitored closely, and weighed after 7 days to check for drug-induced weight loss. Mice were killed when the average tumor diameter exceeds 20 mm. Tumor diameters were measured with callipers three times weekly, and tumor volumes were calculated as 0.52'a$^2$'b, where a and b are the minor and major tumor axes. Data were plotted on a semilogarithmic plot (mean tumor volume versus time after treatment), and the time taken for tumors to reach a mean volume four-fold higher than their pre-treatment volume was calculated. From this, tumor growth delays relative to control mice were calculated.

What is claimed is:

1. A compound which is a bis(acridinecarboxamide) or bis(phenazinecarboxamide) of formula (I):

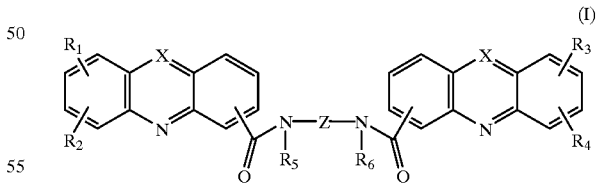

wherein each X, which may be the same or different in a given molecule, is —CH= or —N=, each of $R_1$ to $R_4$ which may be the same or different, is H, $C_1$–$C_4$ alkyl, OH, SH, NH$_2$, $C_1$–$C_4$alkoxy, phenyl, phenyloxy, CF$_3$, NO$_2$, halogen, NHR, N(R)$_2$, SR or SO$_2$R wherein R is $C_1$–$C_4$ alkyl, or $R_1$ and $R_2$ together form a methylenedioxy group; each of $R_5$ and $R_6$, which may the same or different, is H or $C_1$–$C_4$ alkyl; Z is (CH$_2$)$_n$, (CH$_2$)$_n$O(CH$_2$)$_n$, (CH$_2$)$_n$N(R$_7$) (CH$_2$)$_n$, (CH$_2$)$_n$N(R$_7$)(CH$_2$)$_m$N(R$_7$)(CH$_2$)$_n$ or

wherein $R_7$ is H or $C_1$–$C_4$ alkyl and n and m, which may be the same or different, are each an integer of 1 to 4; or a pharmaceutically acceptable acid addition salt or N-oxide thereof; with the exception of compounds wherein each X is N, each of $R_1$ to $R_6$ is H, the carboxamide moiety is attached to position 1 of each phenazine ring and Z is $(CH_2)_2NH(CH_2)_2$, $(CH_2)_3NH(CH_2)_3$,

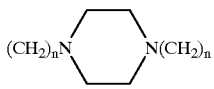

$(CH_2)_2NH(CH)_2NH(CH_2)_2$ or $(CH_2)_3NH(CH_2)_2NH(CH_2)_3$.

2. A compound which is a bis(acridinecarboxamide) or bis(phenazinecarboxamide) of formula (I):

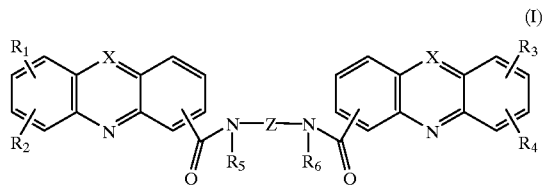

wherein each X, which may be the same or different in a given molecule, is —CH= or —N=, each of $R_1$ to $R_4$ which may be the same or different, is H, $C_1$–$C_4$ alkyl, OH, SH, $NH_2$, $C_1$–$C_4$ alkoxy, phenoxy, $CF_3$, $NO_2$, halogen, NHR, $N(R)_2$, SR, or $SO_2R$ wherein R is $C_1$–$C_4$ alkyl, or $R_1$ and $R_2$ together form a methylenedioxy group; each of $R_5$ and $R_6$, which may be the same or different, is H or $C_1$–$C_4$ alkyl; Z is $(CH_2)_n$, $(CH_2)_nO(CH_2)_n$, $(CH_2)_nN(R_7)(CH_2)_n$, $(CH_2)_nN(R_7)(CH_2)_mN(R_7)(CH_2)_n$ or

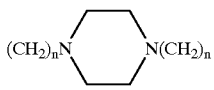

wherein $R_7$ is H or $C_1$–$C_4$ alkyl and n and m, which may be the same or different, are each an integer of 1 to 4; or a pharmaceutically acceptable acid addition salt or N-oxide thereof; with the exception of compounds wherein each X is N, each of $R_1$ to $R_6$ is H, the carboxamide moiety is attached to position 1 of each phenazine ring and Z is $(CH_2)_2NH(CH_2)_2$, $(CH_2)_3NH(CH_2)_3$,

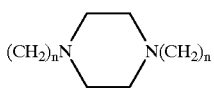

$(CH_2)_2NH(CH_2)_2NH(CH_2)_2$ or $(CH_2)_3NH(CH_2)_2NH(CH_2)_3$.

3. A compound according to claim 1 or 2 which is a bis(acridine carboxamide) of the formula (Ia):

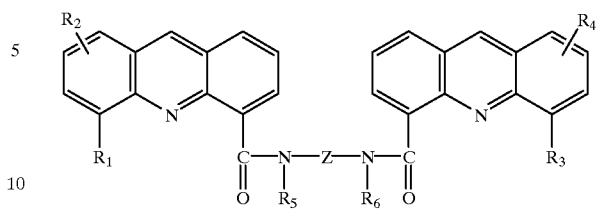

wherein each of $R_1$ and $R_3$, which are the same or different, is $C_1$–$C_4$ alkoxy, $C_1$–$C_4$ alkyl or halogen, each of $R_2$ and $R_4$, which are the same or different, is hydrogen, $C_1$–$C_4$ alkoxy, $C_1$–$C_4$ alkyl or halogen, and each of $R_5$ and $R_6$ is H; or a pharmaceutically acceptable salt or N-oxide thereof.

4. A compound according to claim 1 which is a bis(phenazinecarboxamide) of formula (Ib):

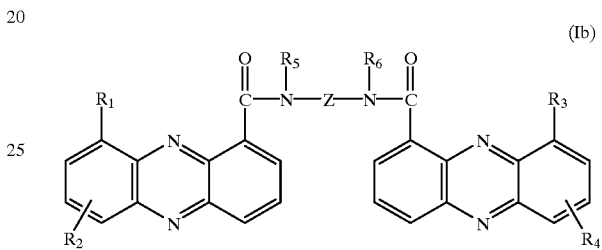

wherein each of $R_1$ and $R_3$, which are the same or different, is $C_1$–$C_4$ alkoxy, $C_1$–$C_4$ alkyl or halogen, each of $R_2$ and $R_4$, which are the same or different, is hydrogen, $C_1$–$C_4$ alkoxy, $C_1$–$C_4$ alkyl or halogen, and each of $R_5$ and $R_6$ is H; or a pharmaceutically acceptable salt or N-oxide thereof.

5. A process for producing a compound as defined in claim 1 or 2, which process comprises reacting two moles of an acridinecarboxylic acid or 9-azaacridine carboxylic acid of formula (II):

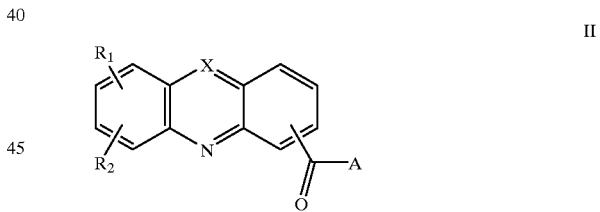

wherein $R_1$, $R_2$ and X are as defined in claim 1 and A is OH, Cl or N-imidazolyl, with one mole of a bis(amine) of formula (III):

wherein $R_5$, $R_6$, and Z are as defined in claim 1; and, if desired, converting the resulting compound into a pharmaceutically acceptable acid addition salt or N-oxide thereof.

6. A pharmaceutical composition which comprises a pharmaceutically acceptable carrier or diluent and, as an active ingredient, a compound as defined in claim 1 or 2.

7. A method of treating a human or animal patient harboring a tumor, which method comprises administering thereto a therapeutically effective amount of a compound as defined in claim 1.

8. A method according to claim 1 wherein the tumor is selected from the group consisting of lung and colon tumors, melanoma and central nervous system (CNS) tumors.

* * * * *